(12) United States Patent
Ahn et al.

(10) Patent No.: US 11,407,763 B2
(45) Date of Patent: Aug. 9, 2022

(54) TRYPTOPHAN HYDROXYLASE INHIBITOR AND PHARMACEUTICAL COMPOSITION INCLUDING SAME

(71) Applicants: GWANGJU INSTITUTE OF SCIENCE AND TECHNOLOGY, Gwangju (KR); KOREA ADVANCED INSTITUTE OF SCIENCE AND TECHNOLOGY, Daejeon (KR); KYUNGPOOK NATIONAL UNIVERSITY INDUSTRY-ACADEMIC COOPERATION FOUNDATION, Daegu (KR); CURACLE CO., LTD., Seongnam-si (KR)

(72) Inventors: Jin Hee Ahn, Gwangju (KR); Hail Kim, Daejeon (KR); Jaemyoung Suh, Daejeon (KR); In-Kyu Lee, Daegu (KR); Kwang-eun Kim, Yuseong-gu Daejeon (KR); Kun-Young Park, Daejeon (KR); Eun Jung Bae, Gwangju (KR); Ko Eun Shong, Daejeon (KR); Suvarna Haus-habhau Pagire, Gwangju (KR); Ajin Lim, Daejeon (KR); Jae-Han Jeon, Daegu (KR); Haushabhau Shivaji Pagire, Gwangju (KR); Haiying Zhang, Seongnam-si (KR); Myung-Hwa Kim, Seongnam-si (KR); Jung-In Pyo, Seongnam-si (KR)

(73) Assignees: Gwangju Institute of Science and Technolgy, Gwangju (KR); Korea Advanced Institute of Science and Technology, Daejeon (KR); KyungPook National University Industry-Academic Cooperation Foundation, Daegu (KR); Curacle Co., LTD., Gyeonggi-Do (KR)

(*) Notice: Subject to any disclaimer, the term of this patent is extended or adjusted under 35 U.S.C. 154(b) by 5 days.

(21) Appl. No.: 16/641,604
(22) PCT Filed: Aug. 24, 2018
(86) PCT No.: PCT/KR2018/009796
§ 371 (c)(1),
(2) Date: Feb. 24, 2020
(87) PCT Pub. No.: WO2019/039905
PCT Pub. Date: Feb. 28, 2019

(65) Prior Publication Data
US 2021/0155634 A1 May 27, 2021

(30) Foreign Application Priority Data
Aug. 24, 2017 (KR) .................. 10-2017-0106983

(51) Int. Cl.
| | |
|---|---|
| C07D 495/04 | (2006.01) |
| C07D 487/04 | (2006.01) |
| C07D 403/12 | (2006.01) |
| C07D 403/14 | (2006.01) |
| C07D 271/06 | (2006.01) |
| C07D 231/12 | (2006.01) |
| C07D 401/14 | (2006.01) |
| C07D 401/12 | (2006.01) |
| C07D 239/47 | (2006.01) |
| C07D 405/12 | (2006.01) |
| C07D 403/08 | (2006.01) |
| A61P 35/00 | (2006.01) |
| A61P 1/00 | (2006.01) |
| C07D 405/14 | (2006.01) |

(52) U.S. Cl.
CPC ............. *C07D 495/04* (2013.01); *A61P 1/00* (2018.01); *A61P 35/00* (2018.01); *C07D 231/12* (2013.01); *C07D 239/47* (2013.01); *C07D 271/06* (2013.01); *C07D 401/12* (2013.01); *C07D 401/14* (2013.01); *C07D 403/08* (2013.01); *C07D 403/12* (2013.01); *C07D 403/14* (2013.01); *C07D 405/12* (2013.01); *C07D 405/14* (2013.01); *C07D 487/04* (2013.01)

(58) Field of Classification Search
CPC .. C07D 495/04; C07D 231/12; C07D 239/47; C07D 271/06; C07D 401/12; C07D 401/14; C07D 403/08; C07D 403/12; C07D 403/14; C07D 405/12; C07D 405/14; C07D 487/04; A61P 1/00; A61P 35/00
USPC ........................................................ 514/250
See application file for complete search history.

(56) References Cited

FOREIGN PATENT DOCUMENTS

| | | |
|---|---|---|
| KR | 1020107002983 A | 7/2008 |
| KR | 10-2008-0081159 | 9/2008 |

(Continued)

OTHER PUBLICATIONS

Ayme-Dietrich et al., Cardiovascular remodeling and the peripheral serotonergic system Archives of Cardiovascular Disease (2017) 110, 51-59.

(Continued)

*Primary Examiner* — Kristin A Vajda
(74) *Attorney, Agent, or Firm* — Workman Nydegger

(57) ABSTRACT

The present invention relates to a novel tryptophan hydroxylase inhibitor and a pharmaceutical composition including same, wherein the novel tryptophan hydroxylase inhibitor has an excellent inhibitory effect on TPH1, and thus can be usefully used for the prevention or treatment of disorders, such as metabolic disorders, cancer, digestive or cardiovascular system disorders, related to TPH1 activity. In particular, the novel tryptophan hydroxylase inhibitor has an excellent treatment effect on inflammatory bowel disorders, and thus can be usefully used for the treatment of inflammatory bowel disorder.

20 Claims, 7 Drawing Sheets

(56) References Cited

FOREIGN PATENT DOCUMENTS

| KR | 10-2010-0041689 A | 4/2010 | | |
|---|---|---|---|---|
| KR | 10-2010-0046189 | 5/2010 | | |
| WO | 2011056916 A1 | 5/2011 | | |
| WO | 2012058598 A1 | 5/2012 | | |
| WO | 2014082034 A1 | 5/2014 | | |
| WO | 2014124523 A1 | 8/2014 | | |
| WO | WO-2018138293 A1 * | 8/2018 | ......... | A61K 31/4985 |

OTHER PUBLICATIONS

Kulke MH et al., Telotristat Etiprate, a Novel Serotonin Synthesis Inhibitor, in Patients with Carcinoid Syndrome and Diarrhea Not Adequately Controlled by Octreotide, Endocr Relat Cancer. Oct. 2014;21(5):705-14.; doi: 10.1530/ERC-14-0173.

Lamarca A et al., Telotristat ethyl: a new option for the management of carcinoid syndrome, Expert Opin Pharmacother. Dec. 2016;17(18):2487-2498.

Aiello R J et al., Tryptophan hydroxylase 1 Inhibition Impacts Pulmonary Vascular Remodeling in Two Rat Models of Pulmonary Hypertension, J Pharmacol Exp Ther. Feb. 2017;360(2):267-279.

Bai Y et al., 4-Chloro-DL-phenylalanine protects against monocrotaline-induced pulmonary vascular remodeling and lung inflammation, Int J Mol Med. Feb. 2014;33(2):373-82.; doi: 10.3892/ijmm.2013.159.

J. J. Kim, et al., Blocking peripheral serotonin synthesis by telotristat etiprate (LX1032/LX1606) reduces severity of both chemical- and infection-induced intestinal inflammation, Am. J. Physiol. Gastrointest. Liver Physiol., 309: G455-G465, 2015.

Manocha et al., Serotonin and GI Disorders: An Update on Clinical and Experimental Studies, Clin Transl Gastroenterol. Apr. 2012; 3(4): e13.

George, et al., SILYLA-N D Germanylmetalcloicm Pounds, J. Am. Chem. Soc. (1960) 82:5566.

Liang, et al. Combined Structure-Based Pharmacophore and 3D-QSAR Studies on Phenylalanine Series Compounds as TPH1 Inhibitors, int. J. Mol. Sci., 13, pp. 5348-5363(2012).

International Search report issue in KR2018009796 dated Nov. 6, 2018.

Goldberg, D.R., et al., "Optimization of spirocyclic proline tryptophan hydroxylase-I inhibitors", Bioorganic & Medicinal Chemistry Letters, Elsevier, vol. 27, No. 3, Dec. 23, 2016, pp. 413-419, XP029883841.

Goldberg, D.R., et al.,"Discovery of spirocyclic proline tryptophan hydroxylase-I inhibitors", Bioorganic & Medicinal Chemistry Letters, vol. 26, No. 4, Jan. 22, 2016, pp. 1124-1129, XP029409789.

Oh C et al., Regulation of systemic energy homeostasis by serotonin in adipose tissues, Nature Communication 6, 6794, 2015.

Vicaut et al., Impact of serotonin on tumour growth, Ann Med 2000; 32 187-194.

Pai et al., Altered serotonin physiology in human breast cancers favors paradoxical growth and cell survival, Breast Cancer Research 2009, 11:R81.

Soll et al., Serotonin Promotes Tumor Growth in Human Hepatocellular Cancer Hepatology 2010;51:1244-1254.

Emad et al., The effect of serotonin and serotonin antagonists on bladder cancer cell proliferationBJU Int. Mar. 2006;97(3):634-9.

* cited by examiner

TRYPTOPHAN HYDROXYLASE INHIBITOR AND PHARMACEUTICAL COMPOSITION INCLUDING SAME

CROSS-REFERENCE TO RELATED APPLICATIONS

This application claims priority to PCT Application No. PCT/KR2018/009796 filed Aug. 24, 2018, entitled "NOVEL TRYPTOPHAN HYDROXYLASE INHIBITOR AND PHARMACEUTICAL COMPOSITION INCLUDING SAME," which claims the benefit of and priority to Korean Patent Application No. 10-2017-0106983, filed on Aug. 24, 2017, all of which are incorporated herein by reference in their entirety.

BACKGROUND OF THE INVENTION

1. Field of the Invention

The present invention relates to a novel tryptophan hydroxylase inhibitor and a pharmaceutical composition comprising the same.

2. Description of the Related Art

Obesity means a condition of excessive accumulation of fat tissue in the body. Obesity is caused by excessive intake of nutrients relative to energy consumption over a long period of time. In modern society, obesity has been classified as a disease since 2013 due to westernization of diet, excessive food intake and lack of exercise. The number of obese patients has increased steadily every year, and more than 500 million adults in the world were found to be obese in 2014. In addition, obesity causes diseases such as type 2 diabetes, fatty liver, circulatory disease, high blood pressure, stroke, colorectal cancer, breast cancer, ovarian cancer and the like.

Treatment methods for obesity include diet, exercise, drug treatment and surgical operation. Particularly, the drug can be classified into an obesity agent acting on the central nerve and an obesity agent acting on the peripheral nerve. The conventional anti-obesity agents are the therapeutic agents that suppress appetite by inhibiting serotonin present in the central nervous system. However, the serotonin present in the central nervous system affects mood, sleep and memory in addition to appetite. The conventional anti-obesity drugs acting on the central nervous system have been reported side effects such as headache, nervousness, tension and depression.

On the other hand, serotonin is a monoamine that acts on the central and peripheral nervous systems. Serotonin does not pass through the blood brain barrier, and is synthesized in the central and peripheral nervous systems, respectively. In the peripheral nervous system, serotonin plays an important role in controlling metabolism of the peripheral tissue. Specifically, if serotonin is over-secreted in the peripheral tissue, it hinders the activity of brown fat cells that burn energy (Oh C et al., Nature Communication 6, 6794, 2015). Thus, it is possible to activate the metabolism of the peripheral tissue by inhibiting the synthesis of the serotonin present in the peripheral nervous system.

The following diseases are known as serotonin-related diseases.

First, it is known that serotonin acts as a tumor growth factor and is associated with various cancers (*Ann Med* 2000; 32: 187-194). Particularly, studies have been reported that serotonin is directly involved in human breast cancer, and cancer progression can be prevented by suppressing the synthesis of serotonin by down-regulation TPH1 in tumor cells since the increase of serotonin can cause malignant progression of breast cancer cells (*Breast Cancer Research* 2009, 11:R81). Furthermore, it is known that serotonin promotes the growth and survival of tumor cells in hepatocellular carcinoma (HEPATOLOGY 2010; 51:1244-1254). It has been also reported that activating or inhibiting serotonin can be a target of bladder cancer treatment by confirming that serotonin promotes the proliferation of bladder cancer cells and that an antagonist to serotonin inhibits the proliferation of bladder cancer cells (BJU Int. 2006 March; 97(3):634-9).

Serotonin is released from platelets and affects the human circulatory system. It is known that the increase of serotonin can cause circulatory diseases such as neointimal hyperplasia, carcinoid tumor, valve thrombosis, ventricular fibrosis, ventricular hypertrophy, arrhythmia, coronary artery spasm, increased occlusion pressure and increased blood pressure (Archives of Circulatory Disease (2017) 110, 51-59). Particularly, carcinoid tumor (carcinoid syndrome) is a disease characterized by the occurrence of watery diarrhea, temporary flushing, bronchial contraction, and eventually causing right valve heart disease. Symptoms of carcinoid syndrome are caused by the elevated level of serotonin secreted by some tumors. Serotonin plays a particularly important role in the onset of carcinoid-related diarrhea and is also known to be associated with the development of carcinoid heart disease. In this regard, studies have shown that telotristat etiprate, a well-known TPH inhibitor, is effective in treating diarrheal patients caused by carcinoids (Kulke M H et al., Endocr Relat Cancer. 2014 October; 21(5):705-14; doi: 10.1530/ERC-14-0173, Lamarca A et al., Expert Opin Pharmacother. 2016 December; 17(18):2487-2498). In addition, the serotonin level in plasma is increased in patients with pulmonary hypertension, one of the circulatory diseases with significantly higher morbidity and mortality than other circulatory diseases (Aiello R J et al., J Pharmacol Exp Ther. 2017 February; 360(2):267-279). It has been known that the use of serotoninergic appetite suppressant drugs (e.g. aminorex and dexfenfluramine) causes pulmonary hypertension, and the serotonin system (serotonin (5-HT) system) is involved in the development of pulmonary hypertension (Bai Y et al., Int J Mol Med. 2014 February; 33(2):373-82; doi: 10.3892/ijmm.2013.159).

Furthermore, mucosal inflammation in the intestine is accompanied by changes in serotonin, and the intestinal serotonin synthesis is catalyzed by tryptophan hydroxylase 1 (TPH1). Therefore, it has been found that the onset and severity of acute and chronic colitis can be delayed by inhibiting TPH1 since the increase in the serotonin synthesis accompanying the development of intestinal inflammation can be prevented through the inhibition of TPH1 (J. J. Kim, et al., Am. J. Physiol. Gastrointest. Liver Physiol., 309: G455-G465, 2015). The increased serotonin content was observed in inflammatory bowel disorder, irritable bowel syndrome and colitis. It is known that celiac disease caused by an immune response to prolamin (gluten protein) and gliadin, causing chronic diarrhea and fatigue is associated with an increase in the number of serotonin-expressing EC cells. It has been also found that the expression of serotonin transporters (SERT) has been reduced in patients with acute polycycliculosis (Clin Transl Gastroenterol. 2012 April; 3(4): e13). These findings suggest that the inflammatory response in the digestive system is deeply related to serotonin signaling.

On the other hand, serotonin is synthesized when tryptophan is hydroxylated by tryptophan hydroxylase. Then, serotonin is produced when the hydroxylated tryptophan is decarboxylated. Therefore, the synthesis of serotonin can be suppressed by inhibiting tryptophan hydroxylase.

Tryptophan hydroxylase has two subtypes: tryptophan hydroxylase 1 (TPH1) and tryptophan hydroxylase 2 (TPH2). TPH1 is mainly expressed in the peripheral tissues including the pineal gland. TPH2, on the other hand, is expressed in the brain and the intestinal nervous system.

Inhibition of tryptophan hydroxylase can be a therapeutic target for various cancers, circulatory and digestive system diseases associated with the changes in serotonin as described above.

SUMMARY OF THE INVENTION

It is an object of the present invention to provide a novel tryptophan hydroxylase inhibitor.

It is another object of the present invention to provide a pharmaceutical composition comprising the novel tryptophan hydroxylase inhibitor as an active ingredient for the prevention or treatment of metabolic disorder.

It is another object of the present invention to provide a pharmaceutical composition comprising the novel tryptophan hydroxylase inhibitor as an active ingredient for the prevention or treatment of cancer.

It is another object of the present invention to provide a pharmaceutical composition comprising the novel tryptophan hydroxylase inhibitor as an active ingredient for the prevention or treatment of digestive or circulatory system disorders.

To achieve the above objects, in an aspect of the present invention, the present invention provides a compound represented by formula 1 below, an isomer thereof, a solvate thereof, a hydrate thereof or a pharmaceutically acceptable salt thereof:

[Formula 1]

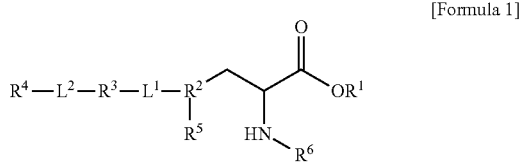

(In formula 1,
$L^1$, $L^2$, $R^1$, $R^2$, $R^3$, $R^4$, $R^5$ and $R^6$ are as defined in this specification).

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of metabolic disorder.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of cancer.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of digestive or circulatory system disorders.

In another aspect of the present invention, the present invention provides a health functional food comprising a compound represented by formula 1, an isomer thereof, a solvate thereof, a hydrate thereof or a pharmaceutically acceptable salt thereof as an active ingredient for the prevention or amelioration of metabolic disorder, cancer, digestive or circulatory system disorders.

In another aspect of the present invention, the present invention provides a method for preventing or treating metabolic disorder, cancer, digestive or circulatory system disorders, which comprises the step of administering a pharmaceutical composition or a health functional food comprising a compound represented by formula 1, an isomer thereof, a solvate thereof, a hydrate thereof or a pharmaceutically acceptable salt thereof as an active ingredient to a subject in need.

In another aspect of the present invention, the present invention provides a use of the pharmaceutical composition or the health functional food comprising a compound represented by formula 1 or a pharmaceutically acceptable salt thereof as an active ingredient for preventing or treating metabolic disorder, cancer, digestive or circulatory system disorders.

Advantageous Effect

The novel tryptophan hydroxylase inhibitor of the present invention has an excellent inhibitory effect on TPH1, and thus can be usefully used for the prevention or treatment of disorders, such as metabolic disorder, cancer, digestive or circulatory system disorders, related to TPH1 activity. In particular, the novel tryptophan hydroxylase inhibitor of the present invention has an excellent treatment effect on inflammatory bowel disorder, and thus can be usefully used for the treatment of inflammatory bowel disorder.

BRIEF DESCRIPTION OF THE DRAWINGS

FIG. 1 is a set of images showing the colons extracted from mice in Experimental Example 3. FIG. 5 is a set of images showing the results of H & E staining performed in Experimental Example 3.

DESCRIPTION OF THE PREFERRED EMBODIMENTS

Figure 1A:
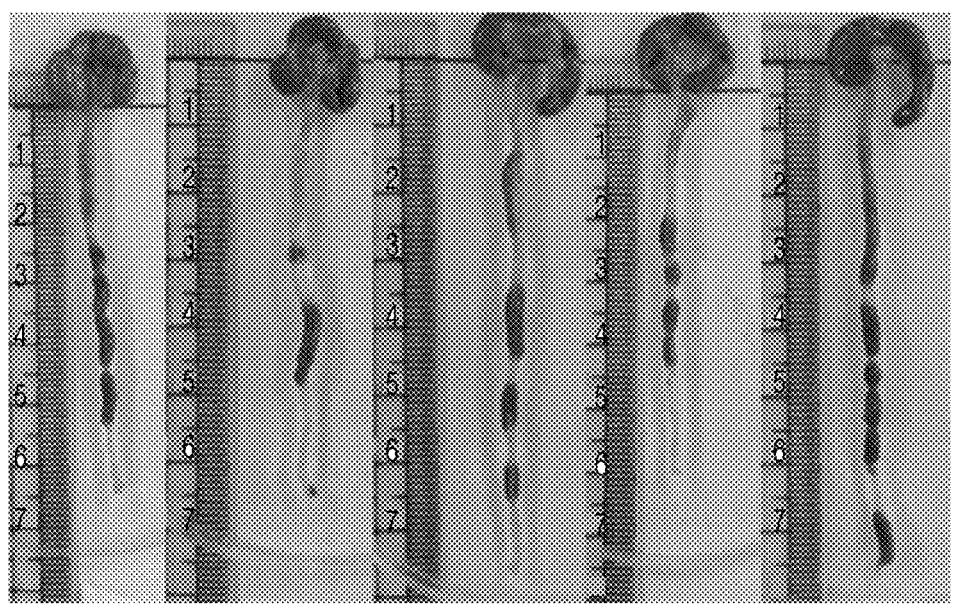
FIG. 1*a*: mouse colon treated with water.
Figure 1B:
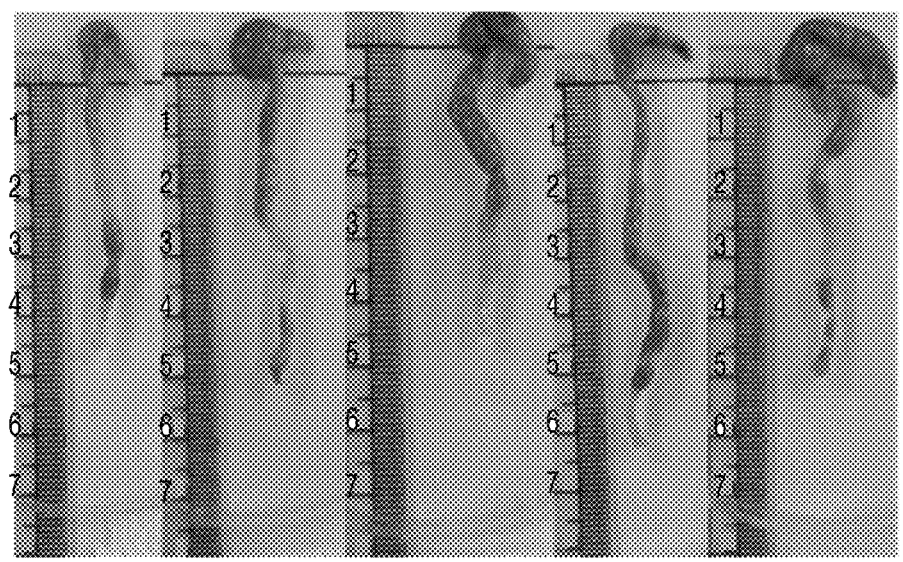
FIG. 1*b*: mouse colon treated with vehicle.
Figure 1C:
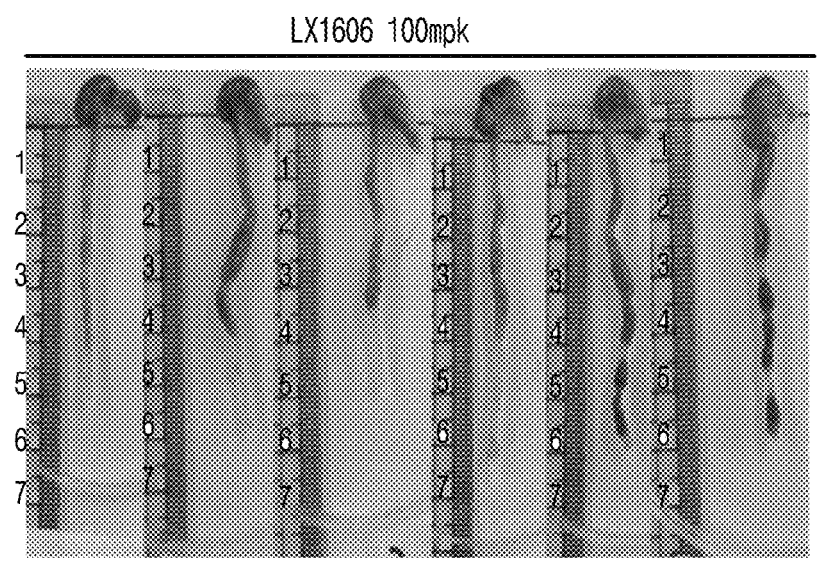
FIG. 1*c*: mouse colon treated with 100 mpk of LX1606.
Figure 1D:
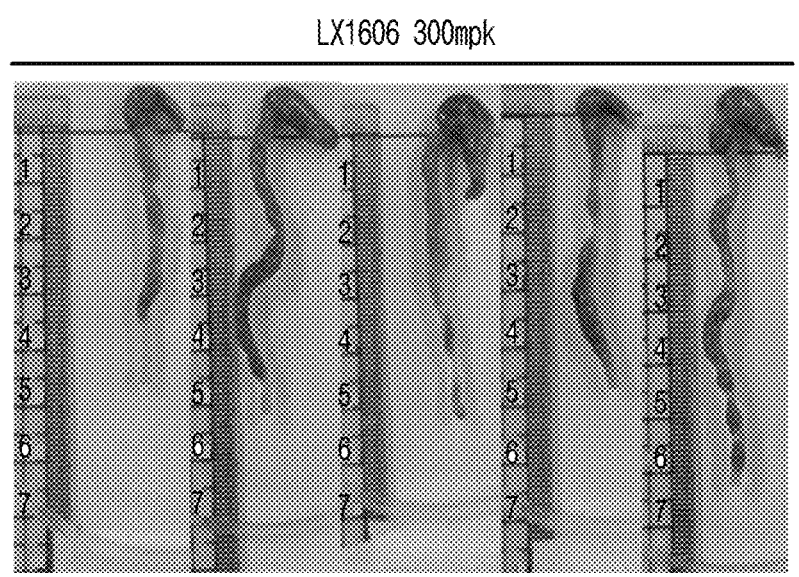
FIG. 1*d*: mouse colon treated with 300 mpk of LX1606.
Figure 1E:
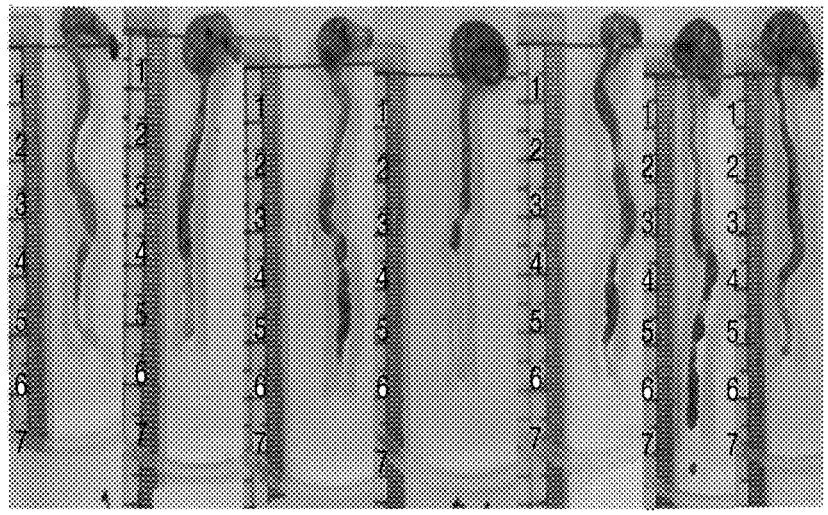
FIG. 1*e*: mouse colon treated with 100 mpk of the compound of Example 53.
Figure 1F:
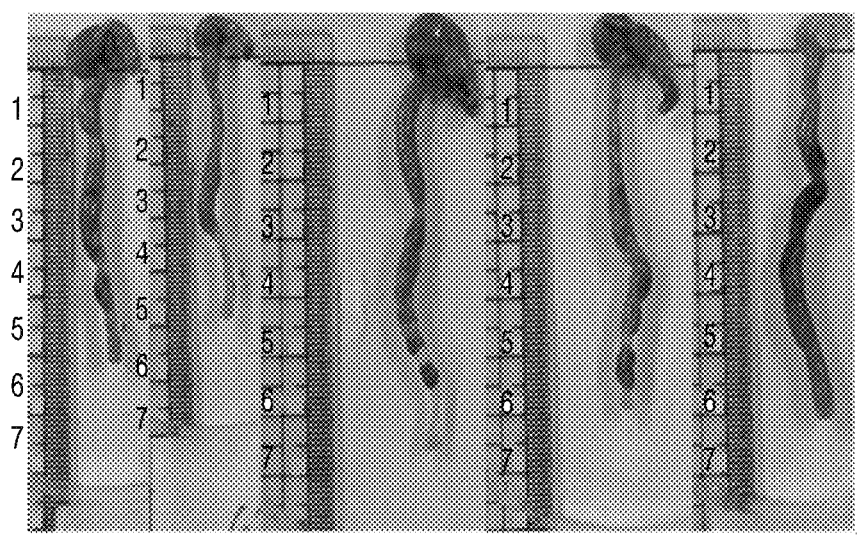
FIG. 1*f*: mouse colon treated with 300 mpk of the compound of Example 53, *mpk=mg/kg

Hereinafter, the present invention is described in detail.
The terms used in this specification can be defined as follows.
"Alkyl" is a hydrocarbon having normal, secondary, tertiary or cyclic carbon atoms. For example, an alkyl group can contain 1 to 20 carbon atoms (i.e., $C_{1-20}$ alkyl), 1 to 10 carbon atoms (i.e., $C_{1-10}$ alkyl), or 1 to 6 carbon atoms (i.e., $C_{1-6}$ alkyl). Examples of the suitable alkyl group include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH$(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2CH_2$ $CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)$ $(CH_2CH_3)_2$), 2-methyl-3-pentyl (—$CH(CH_2CH_3)$ $CH(CH_3)_2$), 2,3-dimethyl-2-butyl (—$C(CH_3)_2CH(CH_3)_2$), 3,3-dimethyl-2-butyl (—$CH(CH_3)$ $C(CH_3)_3$ and octyl (—$(CH_2)_7CH_3$), but not always limited thereto.

"Alkylene" means a branched, straight or cyclic saturated hydrocarbon radical having two monovalent radical centers induced by the removal of two hydrogen atoms from the same or different two carbon atoms of the parent alkane. For example, an alkylene group can contain 1 to 20 carbon atoms, 1 to 10 carbon atoms, or 1 to 6 carbon atoms. The typical alkylene radical includes methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH$ $(CH_3)$—), 1,3-propyl (—$CH_2CH_2CH_2$—), 1,4-butyl (—$CH_2CH_2CH_2CH_2$—), and the like, but not always limited thereto.

"Alkenyl" is a hydrocarbon having normal, secondary, tertiary or cyclic carbon atoms with one or more unsaturated regions, i.e. carbon-carbon and sp2 double bonds. For example, an alkenyl group can contain 2 to 20 carbon atoms (i.e., $C_{2-20}$ alkenyl), 2 to 12 carbon atoms (i.e., $C_{2-12}$ alkenyl), or 2 to 6 carbon atoms (i.e., $C_{2-6}$ alkenyl). Examples of the suitable alkenyl group include ethylene or vinyl (—CH=$CH_2$), allyl (—$CH_2CH$=$CH_2$), cyclopentenyl (—$C_5H_7$) and 5-hexenyl (—$CH_2CH_2CH_2CH_2CH$=$CH_2$), but not always limited thereto.

"Alkenylene" means a branched, straight or cyclic unsaturated hydrocarbon radical having two monovalent radical centers induced by the removal of two hydrogen atoms from the same or different two carbon atoms of the parent alkene. For example, an alkenylene group can contain 1 to 20 carbon atoms, 1 to 10 carbon atoms, or 1 to 6 carbon atoms. The typical alkenylene radical includes 1,2-ethylene (—CH=CH—), but not always limited thereto.

"Alkoxy" means a group having the chemical formula —O-alkyl, wherein the alkyl group defined above is attached to the parent compound through an oxygen atom. The alkyl portion of the alkoxy group can contain 1 to 20 carbon atoms (i.e., $C_{1-20}$ alkoxy), 1 to 12 carbon atoms (i.e., $C_{1-12}$ alkoxy), or 1 to 6 carbon atoms (i.e., $C_{1-6}$ alkoxy). Examples of the suitable alkoxy group include methoxy (—O—$CH_3$ or —OMe), ethoxy (—$OCH_2CH_3$ or —OEt), t-butoxy (—O—$C(CH_3)_3$ or —O-tBu), etc., but not always limited thereto.

"Haloalkyl" is an alkyl group wherein one or more hydrogen atoms of the alkyl group defined above are substituted with halogen atoms. The alkyl portion of the haloalkyl group can contain 1 to 20 carbon atoms (i.e., $C_{1-20}$ haloalkyl), 1 to 12 carbon atoms (i.e., $C_{1-12}$ haloalkyl), or 1 to 6 carbon atoms (i.e., $C_{1-6}$ haloalkyl). Examples of the suitable haloalkyl group include —$CF_3$, —$CHF_2$, —$CFH_2$, —$CH_2CF_3$, etc., but not always limited thereto.

"Amino" refers to —$NR_2$, wherein "R" is independently selected from H, alkyl, substituted alkyl, aryl, substituted aryl, arylalkyl, substituted arylalkyl, etc. The terms alkyl, substituted alkyl, aryl, substituted aryl, arylalkyl and substituted arylalkyl are as defined and described above. The typical amino group includes —$NH_2$, —$N(CH_3)_2$, —NH $(CH_3)$, —$N(CH_2CH_3)_2$, —$NH(CH_2CH_3)$, —NH (substituted or nonsubstituted benzyl), —NH (substituted or non-substituted phenyl), etc., but not always limited thereto.

"Cycloalkyl" refers to a saturated monocycle or polycycle containing only carbon atoms in the ring. Cycloalkyl can have 3 to 7 carbon atoms as a monocycle, 7 to 12 carbon atoms as a bicycle cycloalkyl and up to about 20 carbon atoms as a poly-cycle. The monocyclic cycloalkyl contains 3 to 6 ring atoms, and more typically 5 or 6 ring atoms. The bicyclic cycloalkyl contains 7 to 12 ring atoms arranged in [4,5], [5,5], [5,6] or [6,6] system, or 9 to 10 ring atoms arranged in [5,6] or [6,6] system or spiro-bonded ring. Non-restrictive examples of the monocyclic cycloalkyl include cyclopropyl, cyclobutyl, cyclopentyl and cyclohexyl (They can be substituted or nonsubstituted, respectively).

"Aryl" means an aromatic hydrocarbon radical induced by the removal of one hydrogen atom from six carbon atoms of the parent aromatic ring system. For example, an aryl group can contain 6 to 20 carbon atoms, 6 to 14 carbon atoms, or 6 to 12 carbon atoms. The typical aryl group includes radicals derived from benzene (for example, phenyl), substituted benzene, substituted or nonsubstituted naphthalene, substituted or nonsubstituted anthracene, substituted or nonsubstituted biphenyl, etc., but not always limited thereto.

"Arylalkyl" means a non-cyclic alkyl radical in which one hydrogen atom bound to a carbon atom, typically a terminal or sp3 carbon atom, is substituted with an aryl radical. The typical arylalkyl group includes benzyl, 2-phenylethane-1-yl, naphthylmethyl, 2-naphthylethane-1-yl, naphthobenzyl, 2-naphthophenylethane-1-yl, etc., but not always limited thereto. An arylalkyl group can contain 7 to carbon atoms, for example an alkyl moiety can contain 1 to 6 carbon atoms and an aryl moiety can contain 6 to 14 carbon atoms.

The term "substituted" with respect to alkyl, alkylene, aryl, arylalkyl, heterocyclyl and the like, for example, "substituted alkyl", "substituted alkylene", "substituted aryl", "substituted arylalkyl", "substituted" heterocyclyl and "substituted carbocyclyl (for example, substituted cycloalkyl)" are each alkyl, alkylene, aryl, arylalkyl, heterocyclyl and carbocyclyl (for example, cycloalkyl) in which one or more hydrogen atoms are independently substituted with a non-hydrogen substituent. The typical substituent includes —X, —R, —$O^-$, =O, —OR, —SR, —$S^-$, —$NR_2$, —$N^+R_3$, =NR, —$CX_3$, —CN, —OCN, —SCN, —N=C=O, —NCS, —NO, —$NO_2$, =$N_2$, —$N_3$, —NHC(=O)R, —C(=O)R, —C(=O)NRR —$S(=O)_2O^-$, —$S(=O)_2OH$, —$S(=O)_2R$, —$OS(=O)_2OR$, —$S(=O)_2$ NR, —S(=O)R, —OP(=O) $(OR)_2$, —N(=O) $(OR)_2$, —N(=O) $(O^-)_2$, —N(=O) $(OH)_2$, —N(O) (OR) ($O^-$), —C(=O)R, alkylene-C(=O)R, —C(=O)X, alkylene-C (=O)X, —C(S)R, —C(O)OR, alkylene-C(O)OR, —C(O) $O^-$, alkylene-C(O)$O^-$, —C(S)OR, —C(O)SR, —C(S)SR, —C(O)NRR, alkylene-C(O)NRR, —C(S)NRR, and —C(=NR)NRR (Wherein, each X is independently halogen: F, Cl, Br, or I, and R is independently H, alkyl, aryl, arylalkyl, heterocycle, or a protecting group or a precursor moiety), but not always limited thereto. Alkylene, alkenylene and alkynylene groups can also be similarly substituted.

Those skilled in the art can recognize that when the residues such as "alkyl", "aryl", "heterocyclyl" and the like are substituted with one or more substituents, these can selectively be referred to as the residues such as "alkylene", "arylene", "heterocyclylene", etc. (i.e., one or more hydrogen atoms of the parent "alkyl", "aryl" and "heterocyclyl" residues are substituted with the substituents mentioned above). The residues such as "alkyl", "aryl", "heterocyclyl", etc., are referred to herein as "substituted" or substituted in the figures (or optionally substituted, for example, the number of substituents is zero to positive), the terms "alkyl", "aryl", "heterocyclyl" and the like should be understood to be interchangeable with "alkylene", "arylene", "heterocyclylene" and the like.

Those skilled in the art can recognize that the substituents and other residues of the compound of formula 1 should be selected to provide a compound that is stable enough to provide a pharmaceutically useful compound that can be formulated into an acceptably stable pharmaceutical composition. The compound of formula 1 having such stability is considered to be within the scope of the present invention.

"Heterocycle" or "heterocyclyl" used herein includes those described in the literatures [Paquette, Leo A; Principles of Modern Heterocyclic Chemistry (W.A. Benjamin, N.Y., 1968), particularly, Chapters 1, 3, 4, 6, 7 and 9; The Chemistry of Heterocyclic Compounds, A Series of Monographs" (John Wiley & Sons, New York, 1950 to present), specifically, Volumes 13, 14, 16, 19 and 28; and J. Am. Chem. Soc. (1960) 82:5566], but not always limited thereto. In one specific embodiment of the present invention, "heterocycle" includes "carbocycle" in which one or more (for example, 1, 2, 3 or 4) carbon atoms are substituted with a hetero atom (for example, O, N or S) as defined herein. "Heterocycle" or "heterocyclyl" includes saturated rings, partially unsaturated rings, and aromatic rings (i.e., heteroaromatic rings). Substituted heterocycle includes a heterocyclic ring substituted with any substituents disclosed herein, including, for example, a carbonyl group.

Examples of heterocycle include pyridyl, dihydropyridyl, tetrahydropyri (piperidyl), thiazolyl, tetrahydrothiophenyl, sulfur oxide tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azosinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxatinyl, 2H-pyrrolyl, isothiazolyl, isoxazolyl, pyrazinyl, pyridazinyl, indolinyl, isoindoleyl, 3H-indolyl, 1H-indazoly, purinyl, 4H-quinolinyl, phthalazinyl, naphthyridinyl, quinoxalinyl, quinazolinyl, cynolinyl, pterridinyl, 4H-carbazolyl, carbazolyl, β-carbolinyl, phenantridinyl, acridinyl, pyrimidinyl, phenanthrolinyl, phenazinyl, phenothiazinyl, furazanyl, phenoxazinyl, isochromenyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxolindolyl, benzoxazolinyl, isatinoyl, bis-tetrahydrofuranyl, etc. (Each of them can be substituted or nonsubstituted), but not always limited thereto.

For example, carbon-bound heterocycle can be bound to position 2, 3, 4, 5 or 6 of pyrazine, position 3, 4, 5 or 6 of pyridazine, position 2, 4, 5 or 6 of pyrimidine, position 2, 3, 5 or 6 of pyrazine, position 2, 3, 4 or 5 of furan, tetrahydrofuran, thiofuran, thiophene, pyrrole or tetrahydropyrrole, 2, 4 or 5 position of oxazole, imidazole or thiazole, position 3, 4 or 5 of isoxazole, pyrazole or isothiazole, position 2 or 3 of aziridine, position 2, 3 or 4 of azetidine, position 2, 3, 4, 5, 6, 7 or 8 of quinoline, or position 1, 3, 4, 5, 6, 7 or 8 of isoquinoline, but not always limited thereto. More typically, the carbon-bound heterocycle includes 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl (Each of them can be substituted or nonsubstituted).

For example, nitrogen-bound heterocycle can be bound to position 1 of aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline and 1H-indazole, position 2 of isoindole or isoindolin, position 4 of morpholine, and position 9 of carbazole or β-carboline (Each of them can be substituted or nonsubstituted), but not always limited thereto. More typically, the nitrogen-bound heterocycle includes 1-aziridinyl, 1-azetidyl, 1-pyrrolyl, 1-imidazolyl, 1-pyrazolyl and 1-piperidinyl (Each of them can be substituted or nonsubstituted).

"Heterocyclyl alkyl" refers to a non-cyclic alkyl radical in which one of the hydrogen atoms bound to a carbon atom, typically a terminal or sp3 carbon atom, is substituted with a heterocyclyl radical (i.e., heterocyclyl-alkylene-residue). The typical heterocyclyl alkyl group includes heterocyclyl-$CH_2$—, 2-(heterocyclyl)ethane-1-yl, etc., but not always limited thereto. At this time, the "heterocyclyl" moiety includes any of the heterocyclyl groups described above, including those described in the literature [Principles of Modern Heterocyclic Chemistry]. Those skilled in the art can also understand that the heterocyclyl group can be attached to the alkyl portion of the heterocyclyl alkyl by carbon-carbon bonds or carbon-hetero atom bonds as long as the resulting group is chemically stable. A heterocyclyl alkyl group can contain 2 to 20 carbon atoms, for example an alkyl moiety can contain 1 to 6 carbon atoms and a heterocyclyl moiety can contain 1 to 14 carbon atoms. Examples of heterocyclyl alkyl include heterocycles containing 5-membered sulfur, oxygen and/or nitrogen such as thiazolylmethyl, 2-thiazolylethane-1-yl, imidazolylmethyl, oxazolylmethyl and thiadiazolylmethyl, etc., and heterocycles containing 6-membered sulfur, oxygen and/or nitrogen such as piperidinylmethyl, piperazinylmethyl, morpholinylmethyl, pyridinylmethyl, pyrizinylmethyl, pyrimidylmethyl and pyrazinylmethyl, etc. (The heterocyclyl alkyl can be substituted or nonsubstituted), but not always limited thereto.

"Heteroaryl" refers to an aromatic heterocyclyl having one or more hetero atoms in the ring. Non-restricted examples of the suitable hetero atom that can be included in the aromatic ring include oxygen, sulfur and nitrogen. Non-restricted examples of the heteroaryl ring include everything listed in the definition of "heterocyclyl," including pyridinyl, pyrrolyl, oxazolyl, indolyl, isoindolyl, furinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc (They can be substituted or nonsubstituted).

"Carbocycle" or "carbocyclyl" means a saturated ring, partially unsaturated ring or aromatic ring having 3 to 7 carbon atoms as a monocycle, 7 to 12 carbon atoms as a bicycle, and up to about 20 carbon atoms as a polycycle. The monocyclic carbocycle contains 3 to 6 ring atoms, and more typically 5 or 6 ring atoms. The bicyclic carbocycle contains 7 to 12 ring atoms arranged in [4,5], [5,5], [5,6] or [6,6] system, or 9 to 10 ring atoms arranged in [5,6] or [6,6] system. Examples of the monocyclic or bicyclic carbocycle include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl (They can be substituted or nonsubstituted, respectively).

"Optionally substituted" refers to a specific portion of a compound of formula 1 having one, two, or more substituents (for example, an optionally substituted aryl group).

A "salt thereof" means any acid addition salt and/or base addition salt of the compound according to the present invention, preferably a pharmaceutically acceptable salt thereof.

The "pharmaceutically acceptable salt" means a salt of a compound and is suitable for use in contact with the tissues of humans or lower animals without excessive toxicity, irritation or allergic reactions within the scope of sound medical judgment, A compound having a reasonable gain/risk ratio balance, generally soluble or dispersible in water or oil, and effective for the intended use. The pharmaceutically acceptable salt has a reasonable benefit/risk ratio balance, is generally soluble or dispersible in water or oil, and is effective for the intended use.

In this specification, the term "isomer" is used to mean the stereoisomer commonly used by those skilled in the art without limitation. The stereoisomer collectively refers to the isomer generated by changing the spatial arrangement of atoms in a molecule. Examples of the stereoisomer include an enantiomer and a diastereomer, but not always limited thereto. Definitions of the enantiomer and diastereomer are apparent to those skilled in the art. The enantiomer refers to an isomer that does not overlap with the mirror image, such as the relationship between the right hand and the left hand, and is also called an optical isomer. The diastereomer is a generic term for stereoisomers that are not enantiomeric. Diastereomer can be divided into the diastereomers with different spatial arrangements of the constituent atoms and the cis-trans isomers with different spatial arrangements of atoms due to the unfree rotation of carbon-carbon bonds in cycloalkaine and alkene compounds.

In an aspect of the present invention, the present invention provides a compound represented by formula 1 below, an isomer thereof, a solvate thereof, a hydrate thereof or a pharmaceutically acceptable salt thereof.

[Formula 1]

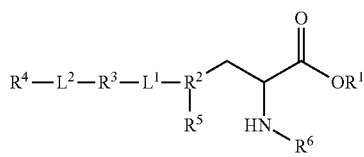

(In formula 1,
$R^1$ is hydrogen or $C_{1-10}$ alkyl;
$R^2$ is $C_{6-10}$ arylene or $C_{6-10}$ cycloalkenylene, at this time, $R^5$ is absent when $R^2$ is $C_{6-10}$ arylene and H when $R^2$ is $C_{6-10}$ cycloalkenylene, $R^6$ is hydrogen or straight or branched $C_{1-6}$ alkoxy, or, $R^5$ and $R^6$ can form 3-10 membered heterocycloalkyl containing one or more hetero atoms along with the carbon and nitrogen atoms to which they are attached;
$R^3$ is 5-13 membered heteroarylene;
$R^4$ is hydrogen, $C_{3-10}$ cycloalkyl, $C_{6-10}$ aryl or 3-10 membered heterocycloalkyl or 5-13 membered heteroaryl;
$L^1$ and $L^2$ are independently —(CH$_2$)x- (x is an integer of 0 to 4), —(CH$_2$)y-O— (y is an integer of 0 to 4), —(CH$_2$)z-N(R$_a$)— (z is an integer of 0 to 4, and R$_a$ is hydrogen or $C_{1-6}$ alkyl), or —CH(C(R$_b$)$_3$)—O— (R$_b$ is hydrogen or halogen);

the said alkyl, aryl, arylene cycloalkenylene, heteroarylene, cycloalkyl, heterocycloalkyl and heteroaryl can be independently substituted with one or more substituents selected form the group consisting of halogen; NH$_2$; hydroxy; $C_{1-6}$ alkyl; $C_{1-6}$ alkoxy; $C_{6-10}$ aryl; hydroxyl $C_{1-6}$ alkyl; hydroxyl $C_{1-6}$ alkoxy; hydroxyl $C_{6-10}$ aryl; halo $C_{1-6}$ alkyl; halo $C_{1-6}$ alkyl; halo $C_{1-6}$ alkoxy; halo $C_{6-10}$ aryl; halo $C_{1-6}$ alkyl; halo $C_{1-6}$ alkoxy; halo $C_{6-10}$ aryl; $C_{1-6}$ alkyl $C_{6-10}$ aryl; $C_{1-6}$, alkoxy $C_{6-10}$ aryl; $C_{1-6}$ alkylcarbonyl; $C_{1-6}$ alkoxycarbonyl; halo $C_{3-10}$ cycloalkenyl; halo $C_{1-6}$ alkoxy $C_{6-10}$ aryl; $C_{3-10}$ cycloalkyl $C_{1-6}$ alkoxy $C_{6-10}$ aryl; hydroxyl $C_{1-6}$ alkyl $C_{6-10}$ aryl; 5-13 membered heteroaryl; fused rings containing halophenyl, pyridine and $C_{5-7}$ cycloalkyl; $C_{1-6}$ alkyl 5-13 membered heteroaryl; 3-10 membered heterpcycloalkenyl; and $C_{1-6}$ alkyl 3-10 membered heterocycloalkenyl, and the substituent can be bound to alkyl, aryl, arylene cycloalkenylene, heteroarylene, cycloalkyl, heterocycloalkyl or heteroaryl by single bonds or double bonds; at this time, the said heteroaryl, heterocycloalkyl, heterocycloalkenyl and heteroarylene independently include one or more hetero atoms selected from the group consisting of N, O and S; and alkyl or alkoxy can have a straight or branched form).

Preferably, $R^1$ is hydrogen or $C_{1-6}$ alkyl;
$R^2$ is phenylene or cyclohexenylene, at this time, $R^3$ is absent when $R^2$ is phenylene and H when $R^2$ is $C_{6-10}$ cycloalkenylene, $R^6$ is hydrogen or straight or branched $C_{1-4}$ alkoxycarbonyl, or, $R^5$ and $R^6$ can form 3-7 membered heterocycloalkyl containing one or more hetero atoms along with the carbon and nitrogen atoms to which they are attached;
$R^3$ is 5-9 membered heteroarylene;
$R^4$ is hydrogen, $C_{6-10}$ aryl or 5-6 membered heterocycloalkyl or 5-6 membered heteroaryl;
$L^1$ and $L^2$ are independently —(CH$_2$)x- (x is 0 or 1), —(CH$_2$)y-O— (y is 0 or 1), —(CH$_2$)z-N(R$_a$)— (z is 0 or 1, and R$_a$ is hydrogen or $C_{1-6}$ alkyl), or —CH(C(R$_b$) $_3$)—O— (R$_b$ is hydrogen or halogen);

the said alkyl, aryl, arylene cycloalkenylene, heteroarylene, cycloalkyl, heterocycloalkyl and heteroaryl can be independently substituted with one or more substituents selected form the group consisting of halogen; NH$_2$; hydroxy; $C_{1-4}$ alkyl; $C_{1-4}$ alkoxy; phenyl; hydroxyl $C_{1-4}$ alkyl; hydroxyl $C_{1-4}$ alkoxy; hydroxyphenyl; halo $C_{1-4}$ alkyl; halo $C_{1-4}$ alkoxy; halophenyl; $C_{1-4}$ alkylphenyl; $C_{1-4}$ alkoxyphenyl; $C_{1-4}$ alkylcarbonyl; $C_{1-4}$ alkoxycarbonyl; halo $C_{5-6}$ cycloalkenyl; halo $C_{1-4}$ alkoxyphenyl; $C_{3-6}$ cycloalkyl $C_1$-4 alkoxyphenyl; hydroxyl $C_{1-4}$ alkylphenyl; 5-9 membered heteroaryl; fused rings containing halophenyl, pyridine and cycloheptyl; $C_{1-4}$ alkyl 5-9 membered heteroaryl; 5-6 membered heterocycloalkenyl; and $C_{1-6}$ alkyl 5-9 membered heterocycloalkenyl, and the substituent can be bound to alkyl, aryl, arylene cycloalkenylene, heteroarylene, cycloalkyl, heterocycloalkyl or heteroaryl by single bonds or double bonds; at this time, the said heteroaryl, heterocycloalkyl, heterocycloalkenyl and heteroarylene independently include one or more hetero atoms selected from the group consisting of N, O and S; and
alkyl or alkoxy can have a straight or branched form.

In addition, $R^1$ is hydrogen or $C_{1-5}$ alkyl;
$R^2$ is

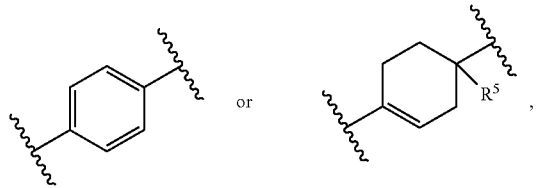

at this time, $R^5$ is H, $R^6$ is hydrogen or tert-butoxycarbonyl, or, $R^5$ and $R^6$ can form

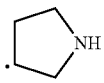

along with the carbon and nitrogen atoms to which they are attached;
$R^3$ is

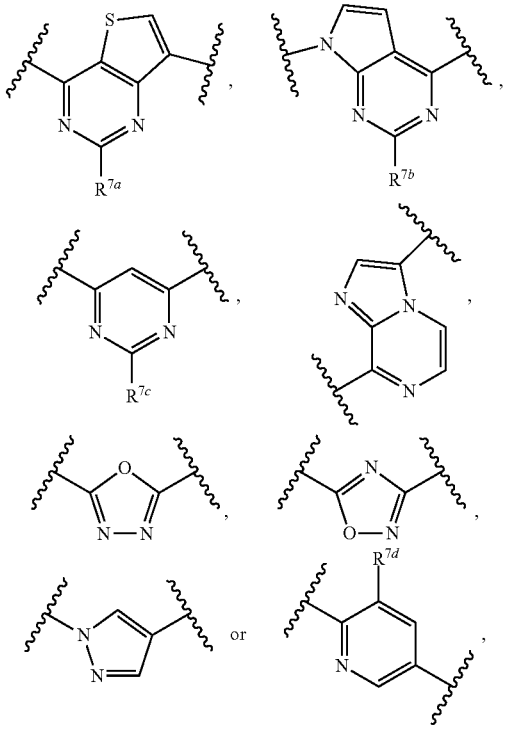

$R^{7a}$, $R^{7b}$, $R^{7c}$ and $R^{7d}$ are independently hydrogen, $NH_2$ or methyl;
$R^4$ is hydrogen,

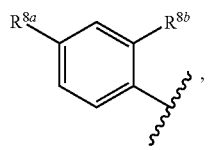, 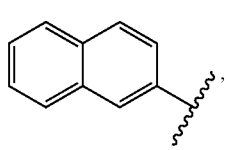,

-continued

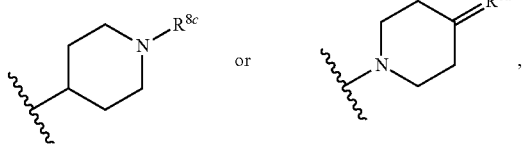

$R^{8a}$ and $R^{8b}$ are independently hydrogen, halogen, $C_{1-4}$ alkoxy, phenyl, furan, benzofuran, methyl-substituted pyrazole, dihydropyran, tetramethyldihydropyran, cyclohexenyl, or difluorocyclohexenyl, and the phenyl can be substituted with a substituent selected from the group consisting of halogen, hydroxy, $C_{1-4}$ alkoxy, halo $C_{1-4}$ alkoxy, $C_{3-6}$ cycloalkyl $C_{1-4}$ alkoxy and hydroxyl $C_{1-4}$ alkyl,
$R^{8c}$ is $C_{1-4}$alkoxycarbonyl,
$R^{8d}$ is

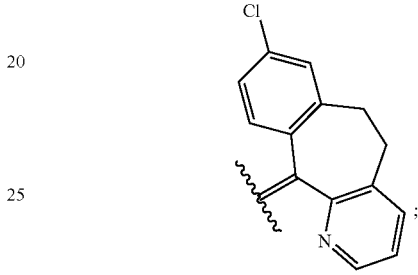

$L^1$ and $L^2$ are independently

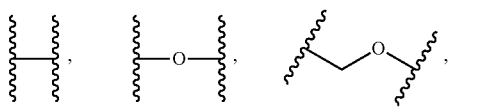

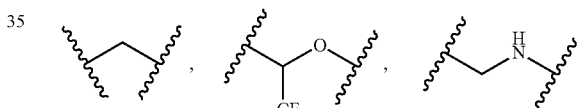

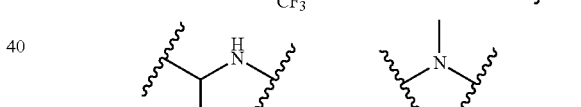

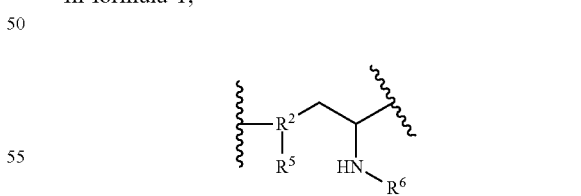

and
alkyl or alkoxy can have a straight or branched form.
In formula 1,
$R^1$ can be hydrogen, methyl, ethyl, n-butyl, t-butyl, i-butyl, n-pentyl, t-pentyl, i-pentyl or neo-pentyl.
In formula 1,

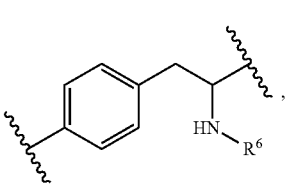

containing $R^2$ can form

-continued
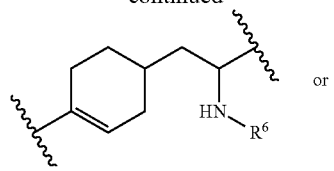 or
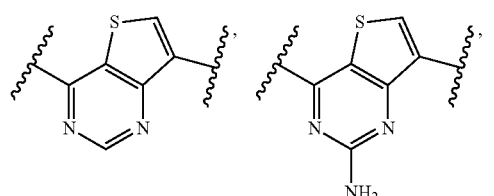,
at this time, R⁶ is hydrogen or tert-butoxycarbonyl.
In formula,
R³ can be
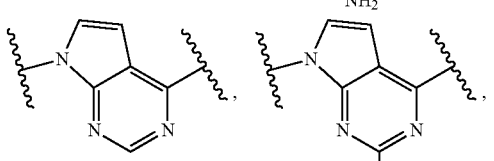
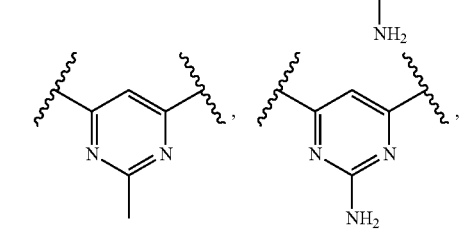
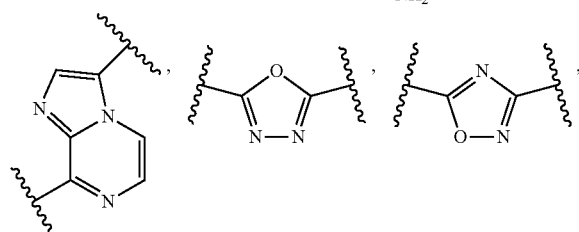
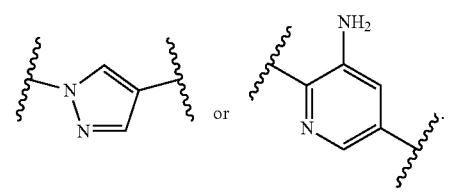 or 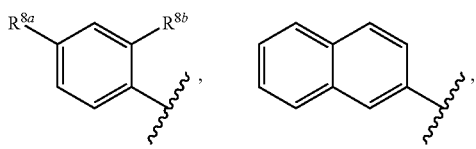.
In formula 1,
R⁴ is hydrogen,
-continued
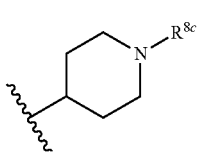 or 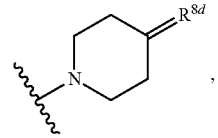,
at this time, $R^{8a}$ is hydrogen, halogen, $C_{1-4}$ alkoxy,
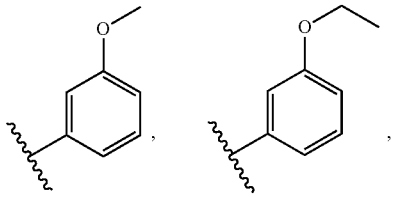
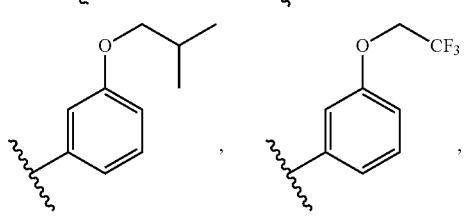
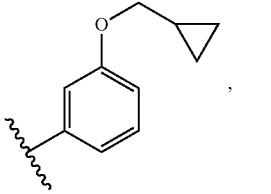, 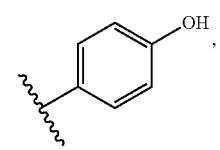
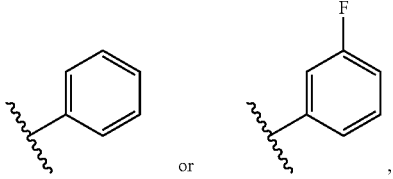 or
$R^{8b}$ is hydrogen, halogen,
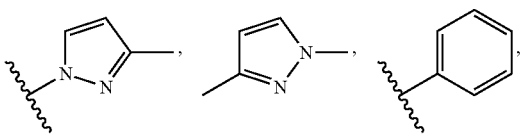
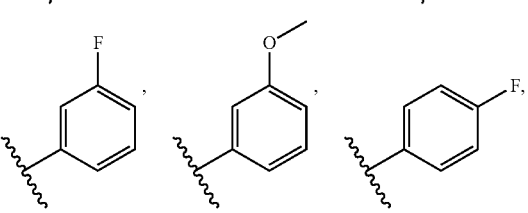
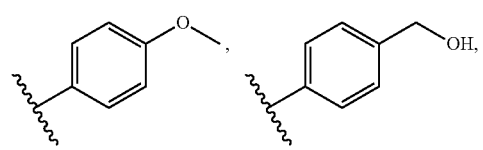

-continued
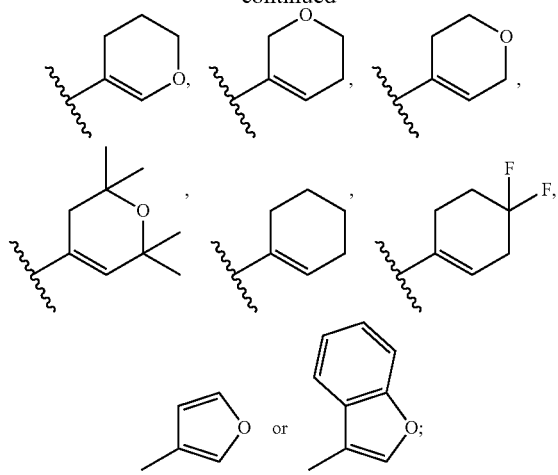
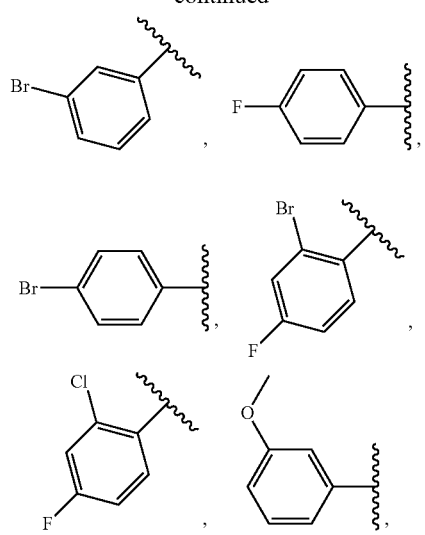
$R^{8c}$ is isopropoxycarbonyl, and
$R^{8d}$ can be
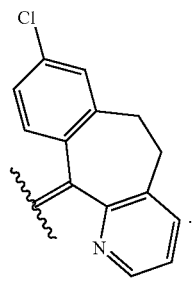 [SMILES: *=C1c2ccc(Cl)cc2CCc2cccnc21]
In formula 1,
$L^1$ is
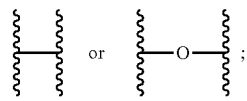
$L^2$ can be
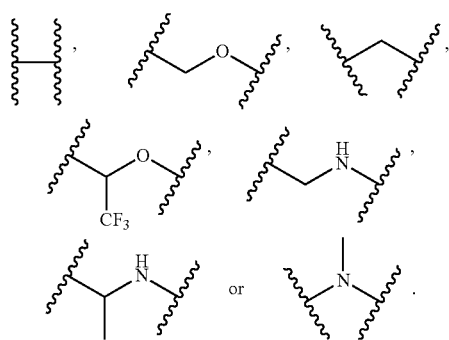
In formula 1,
$R^4$ can be hydrogen,
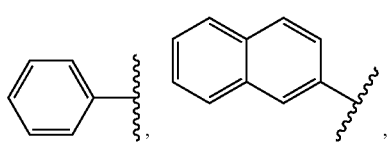
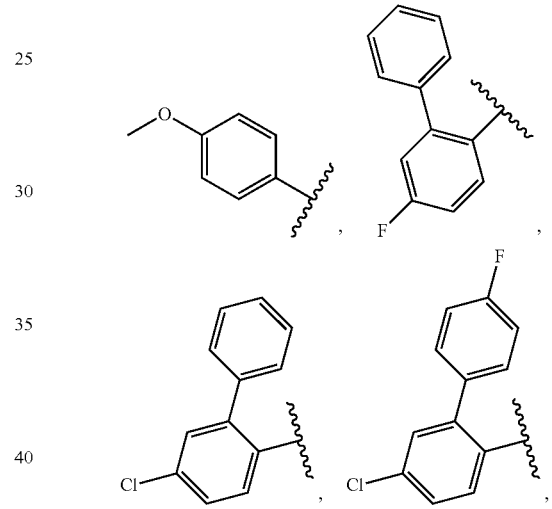
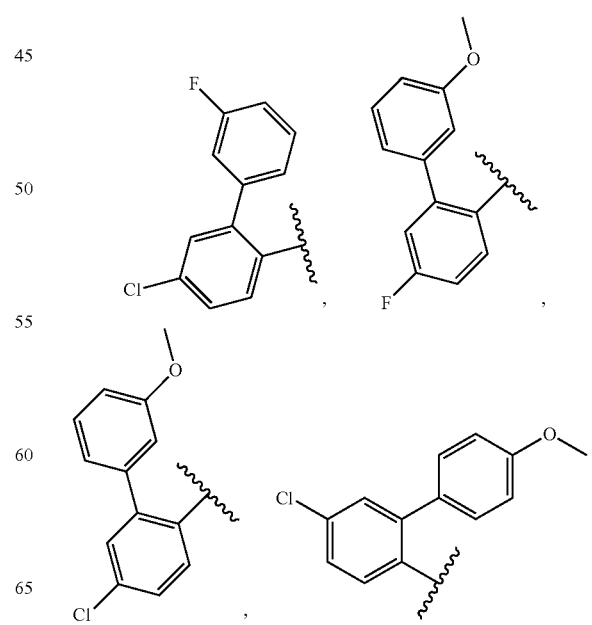

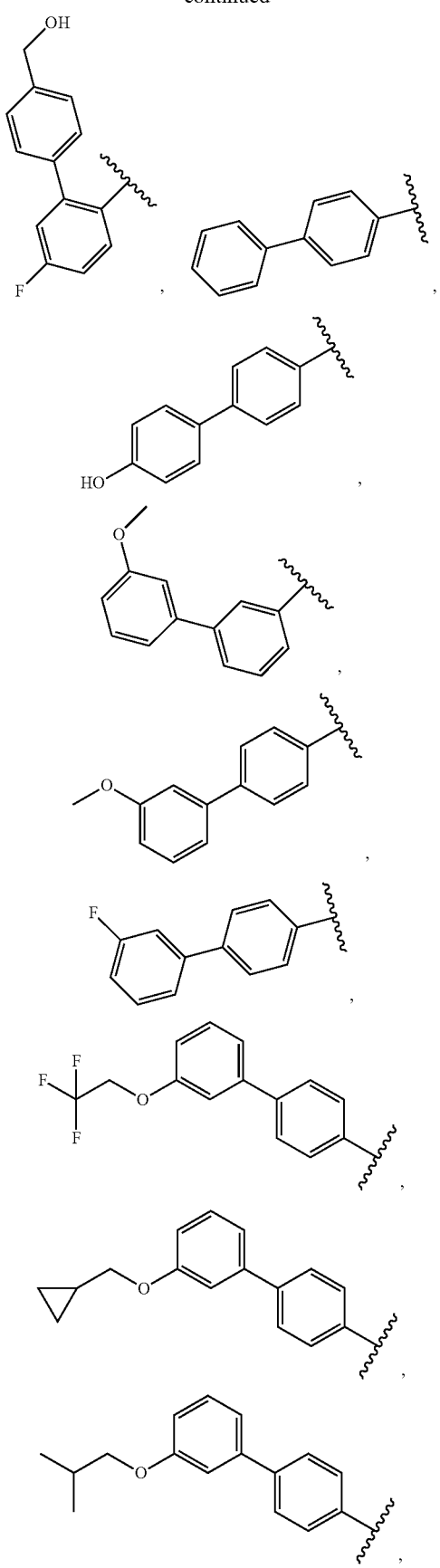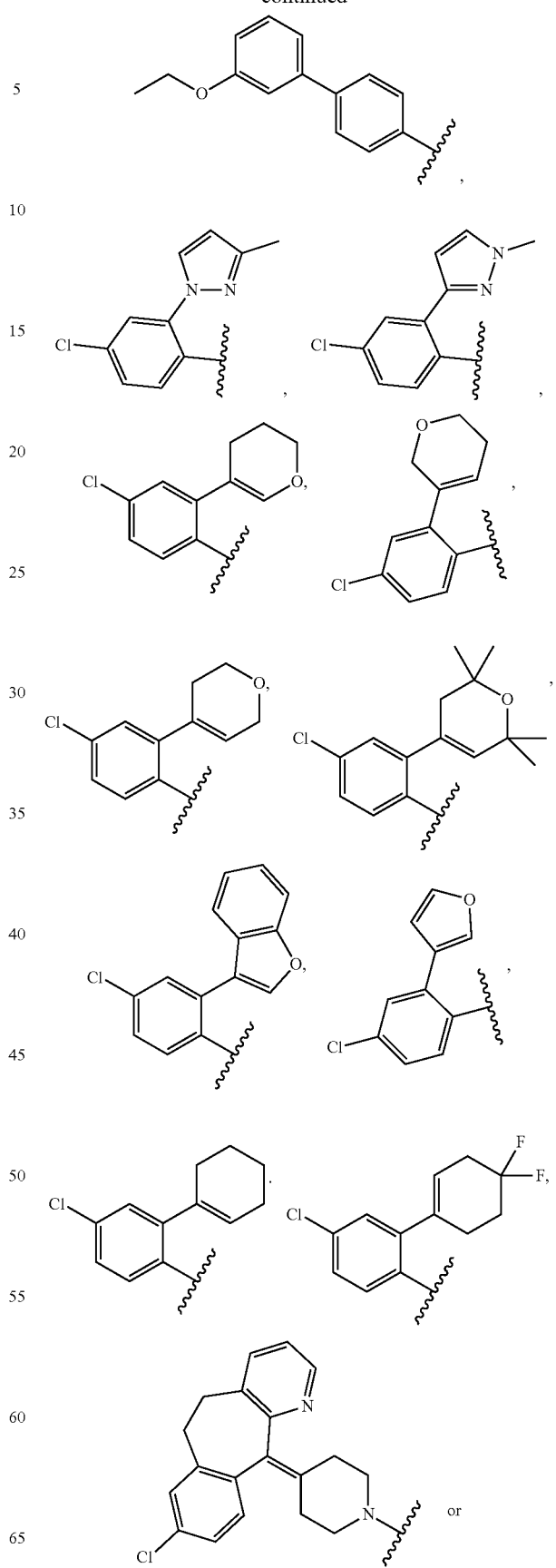

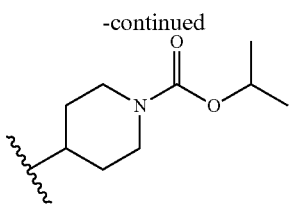

Examples of the compound represented by formula 1 according to the present invention include the following compounds:

<1> (S)-2-amino-3-(4-((7-((5-fluoro-[1,1'-biphenyl]-2-yl)methyl)-7H-pyrrolo[2,3-d]pyrimidine-4-yl)oxy)phenyl)propionic acid hydrochloride;
<2> (S)-2-amino-3-(4-((7-(3-bromobenzyl)-7H-pyrrolo[2,3-d]pyrimidine-4-yl)oxy)phenyl)propionic acid hydrochloride;
<3> (S)-2-amino-3-(4-((2-amino-7-(2-bromo-4-fluorobenzyl)-7H-pyrrolo[2,3-d]pyrimidine-4-yl)oxy)phenyl)propionic acid hydrochloride;
<4> (S)-2-amino-3-(4-((2-amino-7-((5-fluoro-3'-methoxy-[1,1'-biphenyl]-2-yl)methyl)-7H-pyrrolo[2,3-d]pyrimidine-4-yl)oxy)phenyl)propionic acid hydrochloride;
<5> (S)-2-amino-3-(4-((2-amino-7-((5-fluoro-4'-(hydroxymethyl)-[1,1'-biphenyl]-2-yl)methyl)-7H-pyrrolo[2,3-d]pyrimidine-4-yl)oxy)phenyl)propionic acid hydrochloride;
<6> (S)-2-amino-3-(4-((2-amino-7-(2-chloro-4-fluorobenzyl)-7H-pyrrolo[2,3-d]pyrimidine-4-yl)oxy)phenyl)propionic acid hydrochloride;
<7> (S)-2-amino-3-(4-((7-((3'-methoxy-[1,1'-biphenyl]-3-yl)methyl)-7H-pyrrolo[2,3-d]pyrimidine-4-yl)oxy)phenyl)propionic acid hydrochloride;
<8> (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride;
<9> (2S)-2-amino-3-(4-(4-(2,2,2-trifluoro-1-(3'-fluoro-[1,1'-biphenyl]-4-yl)ethoxy)thieno[3,2-d]pyrimidine-7-yl)phenyl)propionic acid hydrochloride;
<10> (2S)-2-amino-3-(4-(4-(2,2,2-trifluoro-1-(3'-methoxy-[1,1'-biphenyl]-4-yl)ethoxy)thieno[3,2-d]pyrimidine-7-yl)phenyl)propionic acid hydrochloride;
<11> (S)-2-amino-3-(4-(2-amino-7-(4-bromobenzyl)-7H-pyrrolo[2,3-d]pyrimidine-4-yl)phenyl)propionic acid hydrochloride;
<12> (S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride;
<13> (S)-2-amino-3-(4-(4-((5-chloro-3'-methoxy-[1,1'-biphenyl]-2-yl)methoxy)thieno[3,2-d]pyrimidine-7-yl)phenyl)propionic acid hydrochloride;
<14> (S)-2-amino-3-(4-(4-((5-chloro-[1,1'-biphenyl]-2-yl)methoxy)thieno[3,2-d]pyrimidine-7-yl)phenyl)propionic acid hydrochloride;
<15> (S)-2-amino-3-(4-(4-((5-chloro-3'-fluoro-[1,1'-biphenyl]-2-yl)methoxy)thieno[3,2-d]pyrimidine-7-yl)phenyl)propionic acid hydrochloride;
<16> (S)-2-amino-3-(4-(4-(benzyloxy)thieno[3,2-d]pyrimidine-7-yl)phenyl)propionic acid hydrochloride;
<17> (S)-2-amino-3-(4-(4-((3'-methoxy-[1,1'-biphenyl]-4-yl)methoxy)thieno[3,2-d]pyrimidine-7-yl)phenyl)propionic acid hydrochloride;
<18> (S)-3-(4-(4-(([1,1'-biphenyl]-4-ylmethyl)amino)thieno[3,2-d]pyrimidine-7-yl)phenyl)-2-aminopropionic acid hydrochloride;
<19> (S)-2-amino-3-(4-(4-(((R)-1-(naphthalene-2-yl)ethyl)amino)thieno[3,2-d]pyrimidine-7-yl)phenyl)propionic acid hydrochloride;
<20> (S)-2-amino-3-(4-(4-((1-(isopropoxycarbonyl)piperidine-4-yl)(methyl)amino)thieno[3,2-d]pyrimidine-7-yl)phenyl)propionic acid hydrochloride;
<21> (S)-2-amino-3-(4-(2-amino-7H-pyrrolo[2,3-d]pyrimidine-4-yl)phenyl)propionic acid;
<22> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hydrochloride;
<23> (S)-2-amino-3-(4-(7-((3'-methoxy-[1,1'-biphenyl]-4-yl)methyl)-7H-pyrrolo[2,3-d]pyrimidine-4-yl)phenyl)propionic acid hydrochloride;
<24> (S)-2-amino-3-(4-(4-((R)-1-(5-chloro-3'-fluoro-[1,1'-biphenyl]-2-yl)-2,2,2-trifluoroethoxy)thieno[3,2-d]pyrimidine-7-yl)phenyl)propionic acid hydrochloride;
<25> (2S)-2-amino-3-(4-(4-(1-(5-chloro-3'-methoxy-[1,1'-biphenyl]-2-yl)-2,2,2-trifluoroethoxy)thieno[3,2-d]pyrimidine-7-yl)phenyl)propionic acid hydrochloride;
<26> (2S)-2-amino-3-(4-(4-(1-(5-chloro-[1,1'-biphenyl]-2-yl)-2,2,2-trifluoroethoxy)thieno[3,2-d]pyrimidine-7-yl)phenyl)propionic acid hydrochloride;
<27> (S)-2-amino-3-(4-(4-((R)-2,2,2-trifluoro-1-(3'-methoxy-[1,1'-biphenyl]-4-yl)ethoxy)thieno[3,2-d]pyrimidine-7-yl)phenyl)propionic acid hydrochloride;
<28> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate;
<29> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate;
<30> (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid hydrochloride;
<31> (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;
<32> (2S)-2-amino-3-(4-(6-((R)-1-(4-chloro-2-(3-methyl-1H-pyrazole-1-yl)phenyl)-2,2,2-trifluoroethoxy)-2-methylpyrimidine-4-yl)cyclohex-3-ene-1-yl)propionic acid hydrochloride;
<33> (2S)-2-amino-3-(4-(7-((3'-methoxy-[1,1'-biphenyl]-4-yl)methyl)-7H-pyrrolo[2,3-d]pyrimidine-4-yl)cyclohex-3-ene-1-yl)propionic acid hydrochloride;
<34> (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid hydrochloride;
<35> (2S)-2-amino-3-(4-(4-((R)-2,2,2-trifluoro-1-(3'-methoxy-[1,1'-biphenyl]-4-yl)ethoxy)thieno[3,2-d]pyrimidine-7-yl)cyclohex-3-ene-1-yl)propionic acid hydrochloride;
<36> ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate;
<37> (S)-2-amino-3-(4-(5-(4-methoxyphenyl)-1,2,4-oxadiazole-3-yl)phenyl)propionic acid hydrochloride;
<38> (S)-2-amino-3-(4-(5-phenyl-1,2,4-oxadiazole-3-yl)phenyl)propionic acid hydrochloride;
<39> (S)-2-amino-3-(4-(5-(4-fluorophenyl)-1,2,4-oxadiazole-3-yl)phenyl)propionic acid hydrochloride;
<40> (S)-2-amino-3-(4-(5-(4-bromophenyl)-1,3,4-oxadiazole-2-yl)phenyl)propionic acid hydrochloride;

<41> (S)-2-amino-3-(4-(5-phenyl-1,3,4-oxadiazole-2-yl)phenyl)propionic acid hydrochloride;

<42> (S)-3-(4-(5-([1,1'-biphenyl]-4-yl)-1,3,4-oxadiazole-2-yl)phenyl)-2-aminopropionic acid hydrochloride;

<43> (S)-2-amino-3-(4-(5-(4'-hydroxy-[1,1'-biphenyl]-4-yl)-1,3,4-oxadiazole-2-yl)phenyl)propionic acid hydrochloride;

<44> (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionic acid;

<45> (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid;

<46> (2S)-2-amino-3-(4-(4-(1-(5-chloro-4'-fluoro-[1,1'-biphenyl]-2-yl)-2,2,2-trifluoroethoxy)thieno[3,2-d]pyrimidine-7-yl)phenyl)propionic acid hydrochloride;

<47> (2S)-2-amino-3-(4-(2-amino-6-(1-(5-chloro-4'-fluoro-[1,1'-biphenyl]-2-yl)-2,2,2-trifluoroethoxy)pyrimidine-4-yl)cyclohex-3-ene-1-yl)propionic acid hydrochloride;

<48> (2S)-2-amino-3-(4-(2-amino-6-(1-(5-chloro-[1,1'-biphenyl]-2-yl)-2,2,2-trifluoroethoxy)pyrimidine-4-yl)cyclohex-3-ene-1-yl)propionic acid hydrochloride;

<49> (2S)-2-amino-3-(4-(1-((3'-methoxy-[1,1'-biphenyl]-4-yl)methyl)-1H-pyrazole-4-yl)cyclohex-3-ene-1-yl)propionic acid hydrochloride;

<50> (2S)-2-amino-3-(4-(4-(1-(5-chloro-4'-fluoro-[1,1'-biphenyl]-2-yl)-2,2,2-trifluoroethoxy)thieno[3,2-d]pyrimidine-7-yl)cyclohex-3-ene-1-yl)propionic acid hydrochloride;

<51> (2S)-2-amino-3-(4-(4-(1-(5-chloro-[1,1'-biphenyl]-2-yl)-2,2,2-trifluoroethoxy)thieno[3,2-d]pyrimidine-7-yl)cyclohex-3-ene-1-yl)propionic acid hydrochloride;

<52> (2S)-2-amino-3-(4-(2-amino-6-(4-(8-chloro-5,6-dihydro-11H-benzo[5,6]cyclohepta[1,2-b]pyridine-11-ylidene)piperidine-1-yl)pyrimidine-4-yl)cyclohex-3-ene-1-yl)propionic acid dihydrochloride;

<53> ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate;

<54> (2S)-2-amino-3-(4-(5-amino-6-((R)-1-(4-chloro-2-(3-methyl-1H-pyrazole-1-yl)phenyl)-2,2,2-trifluoroethoxy)pyridine-3-yl)cyclohex-3-ene-1-yl)propionic acid dihydrochloride;

<55> (2S)-2-amino-3-(4-(8-((R)-1-(4-chloro-2-(3-methyl-1H-pyrazole-1-yl)phenyl)-2,2,2-trifluoroethoxy)imidazo[1,2-a]pyrazine-3-yl)cyclohex-3-ene-1-yl)propionic acid hydrochloride;

<56> (S)-2-amino-3-(4-(8-((R)-1-(4-chloro-2-(3-methyl-1H-pyrazole-1-yl)phenyl)-2,2,2-trifluoroethoxy)imidazo[1,2-a]pyrazine-3-yl)phenyl)propionic acid hydrochloride;

<57> (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid;

<58> (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid;

<59> methyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate;

<60> (2S)-2-amino-3-(4-(2-amino-6-((R)-2,2,2-trifluoro-1-(3'-(2,2,2-trifluoroethoxy)-[1,1'-biphenyl]-4-yl)ethoxy)pyrimidine-4-yl)cyclohex-3-ene-1-yl)propionic acid hydrochloride;

<61> (2S)-2-amino-3-(4-(2-amino-6-((R)-1-(3'-(cyclopropylmethoxy)-[1,1'-biphenyl]-4-yl)-2,2,2-trifluoroethoxy)pyrimidine-4-yl)cyclohex-3-ene-1-yl)propionic acid hydrochloride;

<62> (2S)-2-amino-3-(4-(2-amino-6-((R)-2,2,2-trifluoro-1-(3'-술butoxy-[1,1'-biphenyl]-4-yl)ethoxy)pyrimidine-4-yl)cyclohex-3-ene-1-yl)propionic acid hydrochloride;

<63> (2S)-2-amino-3-(4-(2-amino-6-((R)-1-(3'-ethoxy-[1,1'-biphenyl]-4-yl)-2,2,2-trifluoroethoxy)pyrimidine-4-yl)cyclohex-3-ene-1-yl)propionic acid hydrochloride;

<64> (2S)-2-amino-3-(4-(2-amino-6-((R)-1-(4-chloro-2-(1-methyl-1H-pyrazole-3-yl)phenyl)-2,2,2-trifluoroethoxy)pyrimidine-4-yl)cyclohex-3-ene-1-yl)propionic acid hydrochloride;

<65> ethyl (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionate;

<66> (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride;

<67> (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid;

<68> (2S)-2-amino-3-(4-(2-amino-6-((R)-1-(4-chloro-2-(1-methyl-1H-pyrazole-3-yl)phenyl)-2,2,2-trifluoroethoxy)pyrimidine-4-yl)cyclohex-3-ene-1-yl)propionic acid;

<69> (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid hydrochloride;

<70> (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid;

<71> (2S)-2-amino-3-(4-(2-amino-6-((R)-1-(2-(benzofuran-3-yl)-4-chlorophenyl)-2,2,2-trifluoroethoxy)pyrimidine-4-yl)cyclohex-3-ene-1-yl)propionic acid hydrochloride;

<72> (S)-2-amino-3-(4-(4-((R)-1-(2-(benzofuran-3-yl)-4-chlorophenyl)-2,2,2-trifluoroethoxy)thieno[3,2-d]pyrimidine-7-yl)phenyl)propionic acid hydrochloride;

<73> (S)-2-amino-3-(4-(4-((R)-1-(4-chloro-2-(furan-3-yl)phenyl)-2,2,2-trifluoroethoxy)thieno[3,2-d]pyrimidine-7-yl)phenyl)propionic acid hydrochloride;

<74> (2S)-2-amino-3-(4-(2-amino-6-((R)-1-(4-chloro-2-(furan-3-yl)phenyl)-2,2,2-trifluoroethoxy)pyrimidine-4-yl)cyclohex-3-ene-1-yl)propionic acid hydrochloride;

<75> (2S)-2-amino-3-(4-(2-amino-6-((R)-1-(5-chloro-4',4'difluoro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride;

<76> (2S)-2-amino-3-(4-(2-amino-6-((R)-1-(5-chloro-4'-methoxy-[1,1'-biphenyl]-2-yl)-2,2,2-trifluoroethoxy)pyrimidine-4-yl)cyclohex-3-ene-1-yl)propionic acid hydrochloride;

<77> (2S)-2-amino-3-(4-(2-amino-6-((R)-1-(4-chloro-2-(2,2,6,6-tetramethyl-3,6-dihydro-2H-pyran-4-yl)phenyl)-2,2,2-trifluoroethoxy)pyrimidine-4-yl)cyclohex-3-ene-1-yl)propionic acid hydrochloride;

<78> (S)-2-amino-3-(4-(4-((R)-1-(4-chloro-2-(2,2,6,6-tetramethyl-3,6-dihydro-2H-pyran-4-yl)phenyl)-2,2,2-trifluoroethoxy)thieno[3,2-d]pyrimidine-7-yl)phenyl)propionic acid hydrochloride;

<79> 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<80> 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid;

<81> (S)-2-amino-3-(4-(4-((R)-1-(4-chloro-2-(3,6-dihydro-2H-pyran-4-yl)phenyl)-2,2,2-trifluoroethoxy)thieno[3,2-d]pyrimidine-7-yl)phenyl)propionic acid hydrochloride;

<82> (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid hydrochloride;

<83> 8-(2-amino-6-((R)-1-(4-chloro-2-(3,6-dihydro-2H-pyran-4-yl)phenyl)-2,2,2-trifluoroethoxy)pyrimidine-4-yl)-2-azaspiro[4.5]dec-7-ene-3-carboxylic acid hydrochloride;

<84> 8-(4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride;

<85> (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid;

<86> ethyl (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionate hippurate;

<87> 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid hydrochloride;

<88> 8-(2-amino-6-((R)-2,2,2-trifluoro-1-(3'-fluoro-[1,1'-biphenyl]-4-yl)ethoxy)pyrimidine-4-yl)-2-azaspiro[4.5]dec-7-ene-3-carboxylic acid hydrochloride;

<89> 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid;

<90> (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid hydrochloride;

<91> (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride;

<92> (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid;

<93> 8-(4-((R)-1-(4-chloro-2-(5,6-dihydro-2H-pyran-3-yl)phenyl)-2,2,2-trifluoroethoxy)thieno[3,2-d]pyrimidine-7-yl)-2-azaspiro[4.5]dec-7-ene-3-carboxylic acid hydrochloride;

<94> 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride; fluoro-[1,1'-biphenyl]-4-yl)ethoxy)pyrimidine-4-yl)-2-azaspiro[4.5]dec-7-ene-3-carboxylic acid;

<96> neopentyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate;

<97> (2S)-2-amino-3-(4-(2-amino-6-((R)-1-(4-chloro-2-(3,4-dihydro-2H-pyran-5-yl)phenyl)-2,2,2-trifluoroethoxy)pyrimidine-4-yl)cyclohex-3-ene-1-yl)propionic acid hydrochloride;

<98> (2S)-2-amino-3-(4-(2-amino-6-((R)-1-(5-chloro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride;

<99> (S)-2-amino-3-((R)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;

<100> (S)-2-amino-3-((S)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;

<101> (S)-2-amino-3-((R)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride;

<102> (S)-2-amino-3-((S)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride;

<103> (S)-2-amino-3-(4-(4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride;

<104> (S)-2-amino-3-(4-(4-((R)-1-(5-chloro-2',3',4',5'-tetrahydro-[1,1'-biphenyl]-2-yl)-2,2,2-trifluoroethoxy)thieno[3,2-d]pyrimidine-7-yl)phenyl)propionic acid hydrochloride;

<105> (S)-2-amino-3-(4-(2-amino-4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid hydrochloride;

<106> (S)-2-amino-3-(4-(2-amino-4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride;

<107> 8-(2-amino-4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride;

<108> 8-(2-amino-6-((R)-1-(4-chloro-2-(3,4-dihydro-2H-pyran-5-yl)phenyl)-2,2,2-trifluoroethoxy)pyrimidine-4-yl)-2-azaspiro[4.5]dec-7-ene-3-carboxylic acid hydrochloride;

<109> 8-(2-amino-6-((R)-1-(5-chloro-2',3',4',5'-tetrahydro-[1,1'-biphenyl]-2-yl)-2,2,2-trifluoroethoxy)pyrimidine-4-yl)-2-azaspiro[4.5]dec-7-ene-3-carboxylic acid hydrochloride;

<110> (3S,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<111> (3S,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<112> (3R,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<113> (3R,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<114> (3S,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;

<115> (3S,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;
<116> (3R,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;
<117> (3R,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;
<118> ethyl 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylate hippurate;
<119> ethyl 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylate hippurate;
<120> ethyl (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate.

The compound represented by formula 1 above can be a compound represented by formula 2 below.

[Formula 2]

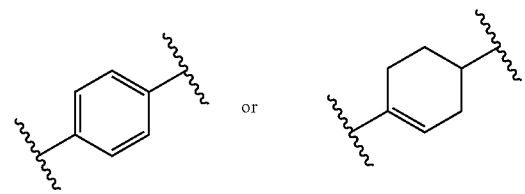 [SMILES: *c1ccc(*)cc1 ; *C1=CCC(*)CC1]

In formula 2,
$R^1$ is hydrogen or $C_{1-6}$ alkyl;
$R^2$ is $C_{6-10}$ arylene or $C_{6-10}$ cycloalkenylene;
$R^3$ is 5-13 membered heteroarylene;
$R^4$ is hydrogen, $C_{3-10}$ cycloalkyl, $C_{6-10}$ aryl, 3-10 membered heterocycloalkyl, or 5-13 membered heteroaryl;
the said alkyl, arylene, cycloalkenylene, heteroarylene, cycloalkyl, heterocycloalkyl and heteroaryl can be independently substituted with one or more substituents selected form the group consisting of hydrogen, halogen, amino, hydroxy, $C_{1-6}$ alkyl, $C_{1-6}$ alkoxy, $C_{6-10}$ aryl, hydroxyl $C_{1-6}$ alkyl, hydroxyl $C_{1-6}$ alkoxy, hydroxyl $C_{6-10}$ aryl, halo $C_{1-6}$ alkyl, halo $C_{1-6}$ alkoxy, halo $C_{6-10}$ aryl, $C_{1-6}$ alkyl $C_{6-10}$ aryl, $C_{1-6}$ alkoxy $C_{6-10}$ aryl, $C_{1-6}$ alkylcarbonyl, $C_{1-6}$ alkoxycarbonyl, 5-13 membered heteroaryl and $C_{1-6}$ alkyl 5-13 membered heteroaryl, at this time, the said heteroaryl, heterocycloalkyl and heteroarylene independently include one or more hetero atoms selected from the group consisting of N, O and S;
$L^1$ and $L^2$ are independently —(CH$_2$)x- (x is an integer of 0 to 4), —(CH$_2$)y-O— (y is an integer of 0 to 4), —(CH$_2$)z-N(R$_a$)— (z is an integer of 0 to 4, and R$_a$ is hydrogen or $C_{1-6}$ alkyl), or —CH(C(R$_b$)$_3$)—O— (R$_b$ is hydrogen or halogen).

R can be or

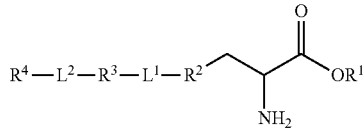

$R^3$ can be

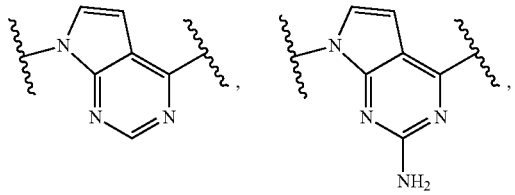

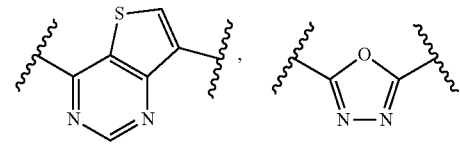

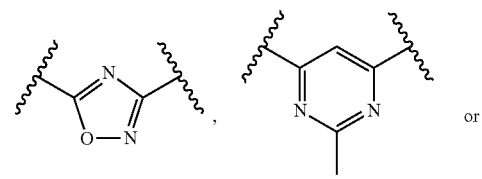

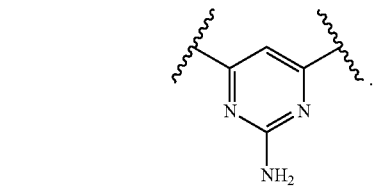

or $R^4$ can be hydrogen,

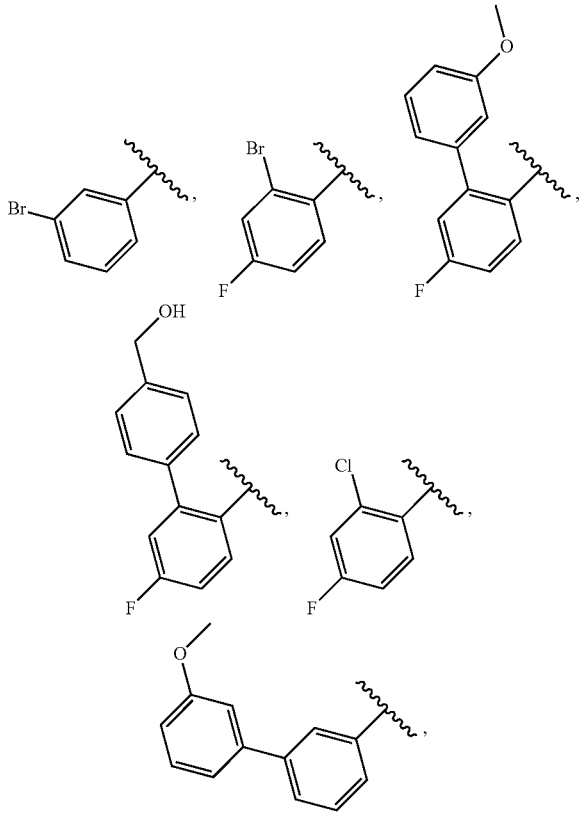

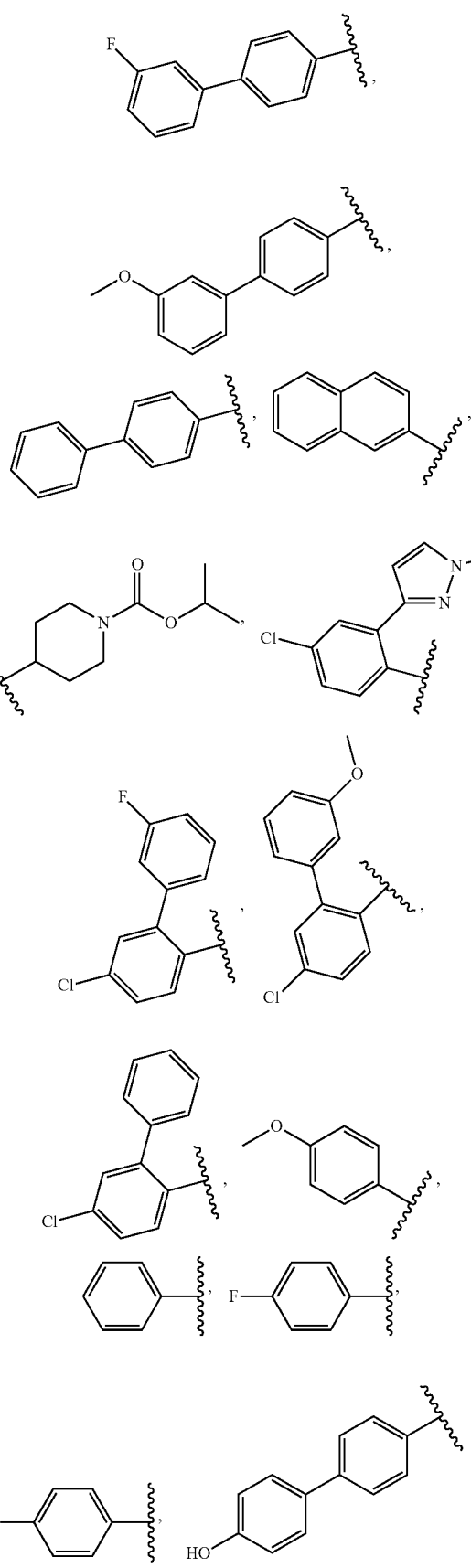

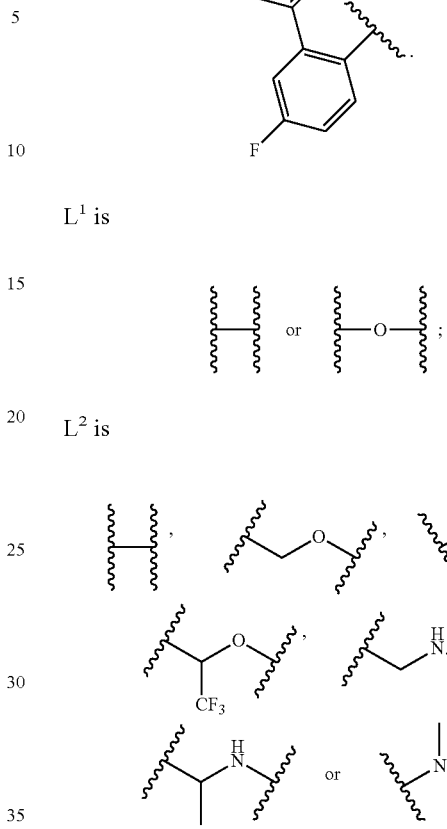

L¹ is or ;

L² is

, , ,

, , or .

Examples of the compound represented by formula 2 according to the present invention include the following compounds:

<1> (S)-2-amino-3-(4-((7-((5-fluoro-[1,1'-biphenyl]-2-yl)methyl)-7H-pyrrolo[2,3-d]pyrimidine-4-yl)oxy)phenyl) propionic acid hydrochloride;

<2> (S)-2-amino-3-(4-((7-(3-bromobenzyl)-7H-pyrrolo[2,3-d]pyrimidine-4-yl)oxy)phenyl)propionic acid hydrochloride;

<3> (S)-2-amino-3-(4-((2-amino-7-(2-bromo-4-fluorobenzyl)-7H-pyrrolo[2,3-d]pyrimidine-4-yl)oxy)phenyl)propionic acid hydrochloride;

<4> (S)-2-amino-3-(4-((2-amino-7-((5-fluoro-3'-methoxy-[1,1'-biphenyl]-2-yl)methyl)-7H-pyrrolo[2,3-d]pyrimidine-4-yl)oxy)phenyl)propionic acid hydrochloride; (hydroxymethyl)-[1,1'-biphenyl]-2-yl)methyl)-7H-pyrrolo[2,3-d]pyrimidine-4-yl)oxy)phenyl)propionic acid hydrochloride;

<6> (S)-2-amino-3-(4-((2-amino-7-(2-chloro-4-fluorobenzyl)-7H-pyrrolo[2,3-d]pyrimidine-4-yl)oxy)phenyl)propionic acid hydrochloride;

<7> (S)-2-amino-3-(4-((7-((3'-methoxy-[1,1'-biphenyl]-3-yl)methyl)-7H-pyrrolo[2,3-d]pyrimidine-4-yl)oxy)phenyl)propionic acid hydrochloride;

<8> (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride;

<9> (2S)-2-amino-3-(4-(4-(2,2,2-trifluoro-1-(3'-fluoro-[1,1'-biphenyl]-4-yl)ethoxy)thieno[3,2-d]pyrimidine-7-yl)phenyl)propionic acid hydrochloride;

<10> (2S)-2-amino-3-(4-(4-(2,2,2-trifluoro-1-(3'-methoxy-[1,1'-biphenyl]-4-yl)ethoxy)thieno[3,2-d]pyrimidine-7-yl)phenyl)propionic acid hydrochloride;

<11> (S)-2-amino-3-(4-(2-amino-7-(4-bromobenzyl)-7H-pyrrolo[2,3-d]pyrimidine-4-yl)phenyl)propionic acid hydrochloride;

<12> (S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride;

<13> (S)-2-amino-3-(4-(4-((5-chloro-3'-methoxy-[1,1'-biphenyl]-2-yl)methoxy)thieno[3,2-d]pyrimidine-7-yl)phenyl)propionic acid hydrochloride;

<14> (S)-2-amino-3-(4-(4-((5-chloro-[1,1'-biphenyl]-2-yl)methoxy)thieno[3,2-d]pyrimidine-7-yl)phenyl)propionic acid hydrochloride;

<15> (S)-2-amino-3-(4-(4-((5-chloro-3'-fluoro-[1,1'-biphenyl]-2-yl)methoxy)thieno[3,2-d]pyrimidine-7-yl)phenyl)propionic acid hydrochloride;

<16> (S)-2-amino-3-(4-(4-(benzyloxy)thieno[3,2-d]pyrimidine-7-yl)phenyl)propionic acid hydrochloride;

<17> (S)-2-amino-3-(4-(4-((3'-methoxy-[1,1'-biphenyl]-4-yl)methoxy)thieno[3,2-d]pyrimidine-7-yl)phenyl)propionic acid hydrochloride;

<18> (S)-3-(4-(4-(([1,1'-biphenyl]-4-ylmethyl)amino)thieno[3,2-d]pyrimidine-7-yl)phenyl)-2-aminopropionic acid hydrochloride;

<19> (S)-2-amino-3-(4-(4-(((R)-1-(naphthalene-2-yl)ethyl)amino)thieno[3,2-d]pyrimidine-7-yl)phenyl)propionic acid hydrochloride;

<20> (S)-2-amino-3-(4-(4-((1-(isopropoxycarbonyl)piperidine-4-yl)(methyl)amino)thieno[3,2-d]pyrimidine-7-yl)phenyl)propionic acid hydrochloride;

<21> (S)-2-amino-3-(4-(2-amino-7H-pyrrolo[2,3-d]pyrimidine-4-yl)phenyl)propionic acid;

<22> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hydrochloride;

<23> (S)-2-amino-3-(4-(7-((3'-methoxy-[1,1'-biphenyl]-4-yl)methyl)-7H-pyrrolo[2,3-d]pyrimidine-4-yl)phenyl)propionic acid hydrochloride;

<24> (S)-2-amino-3-(4-(4-((R)-1-(5-chloro-3'-fluoro-[1,1'-biphenyl]-2-yl)-2,2,2-trifluoroethoxy)thieno[3,2-d]pyrimidine-7-yl)phenyl)propionic acid hydrochloride;

<25> (2S)-2-amino-3-(4-(4-(1-(5-chloro-3'-methoxy-[1,1'-biphenyl]-2-yl)-2,2,2-trifluoroethoxy)thieno[3,2-d]pyrimidine-7-yl)phenyl)propionic acid hydrochloride;

<26> (2S)-2-amino-3-(4-(4-(1-(5-chloro-[1,1'-biphenyl]-2-yl)-2,2,2-trifluoroethoxy)thieno[3,2-d]pyrimidine-7-yl)phenyl)propionic acid hydrochloride;

<27> (S)-2-amino-3-(4-(4-((R)-2,2,2-trifluoro-1-(3'-methoxy-[1,1'-biphenyl]-4-yl)ethoxy)thieno[3,2-d]pyrimidine-7-yl)phenyl)propionic acid hydrochloride;

<28> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate;

<29> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate;

<30> (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid hydrochloride;

<31> (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;

<32> (2S)-2-amino-3-(4-(6-((R)-1-(4-chloro-2-(3-methyl-1H-pyrazole-1-yl)phenyl)-2,2,2-trifluoroethoxy)-2-methylpyrimidine-4-yl)cyclohex-3-ene-1-yl)propionic acid hydrochloride;

<33> (2S)-2-amino-3-(4-(7-((3'-methoxy-[1,1'-biphenyl]-4-yl)methyl)-7H-pyrrolo[2,3-d]pyrimidine-4-yl)cyclohex-3-ene-1-yl)propionic acid hydrochloride;

<34> (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid hydrochloride;

<35> (2S)-2-amino-3-(4-(4-((R)-2,2,2-trifluoro-1-(3'-methoxy-[1,1'-biphenyl]-4-yl)ethoxy)thieno[3,2-d]pyrimidine-7-yl)cyclohex-3-ene-1-yl)propionic acid hydrochloride;

<36> ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate;

<37> (S)-2-amino-3-(4-(5-(4-methoxyphenyl)-1,2,4-oxadiazole-3-yl)phenyl)propionic acid hydrochloride;

<38> (S)-2-amino-3-(4-(5-phenyl-1,2,4-oxadiazole-3-yl)phenyl)propionic acid hydrochloride;

<39> (S)-2-amino-3-(4-(5-(4-fluorophenyl)-1,2,4-oxadiazole-3-yl)phenyl)propionic acid hydrochloride;

<40> (S)-2-amino-3-(4-(5-(4-bromophenyl)-1,3,4-oxadiazole-2-yl)phenyl)propionic acid hydrochloride;

<41> (S)-2-amino-3-(4-(5-phenyl-1,3,4-oxadiazole-2-yl)phenyl)propionic acid hydrochloride;

<42> (S)-3-(4-(5-([1,1'-biphenyl]-4-yl)-1,3,4-oxadiazole-2-yl)phenyl)-2-aminopropionic acid hydrochloride;

<43> (S)-2-amino-3-(4-(5-(4'-hydroxy-[1,1'-biphenyl]-4-yl)-1,3,4-oxadiazole-2-yl)phenyl)propionic acid hydrochloride;

In the present invention, the compound represented by formula 1 or formula 2 can be an L-type or D-type optical isomer. Preferably, the compound can be an L type optical isomer.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 and the pharmaceutically acceptable salt thereof, but also solvates, optical isomers, hydrates, and the like that can be prepared therefrom.

The term "hydrate" refers to a compound of the present invention or a salt thereof comprising a stoichiometric or non-stoichiometric amount of water bound by non-covalent intermolecular force. The hydrate of the compound represented by formula 1 of the present invention can include a stoichiometric or non-stoichiometric amount of water bound by non-covalent intermolecular force. The hydrate can contain 1 equivalent or more, preferably 1 to 5 equivalents of water. Such hydrates can be prepared by crystallizing the compound represented by formula 1 of the present invention, the isomer thereof or the pharmaceutically acceptable salt thereof from water or a solvent containing water.

The term "solvate" refers to a compound of the present invention or a salt thereof comprising a stoichiometric or non-stoichiometric amount of solvent bound by non-covalent intermolecular force. Examples of the preferred solvent include volatile, non-toxic, and/or suitable solvents for human administration.

The term "isomer" means a compound of the present invention or a salt thereof that has the same chemical or molecular formula, but which is structurally or sterically different. Such isomers include structural isomers such as tautomers, R or S isomers having asymmetric carbon centers, stereoisomers such as geometric isomers (trans and cis), and optical isomers (enantiomers). All these isomers and the mixtures thereof are also within the scope of the present invention.

The compound represented by formula 1 or 2 can be prepared according to the preparation methods shown in reaction formulas 1 to 5 below, or can be prepared by the preparation methods of the following examples.

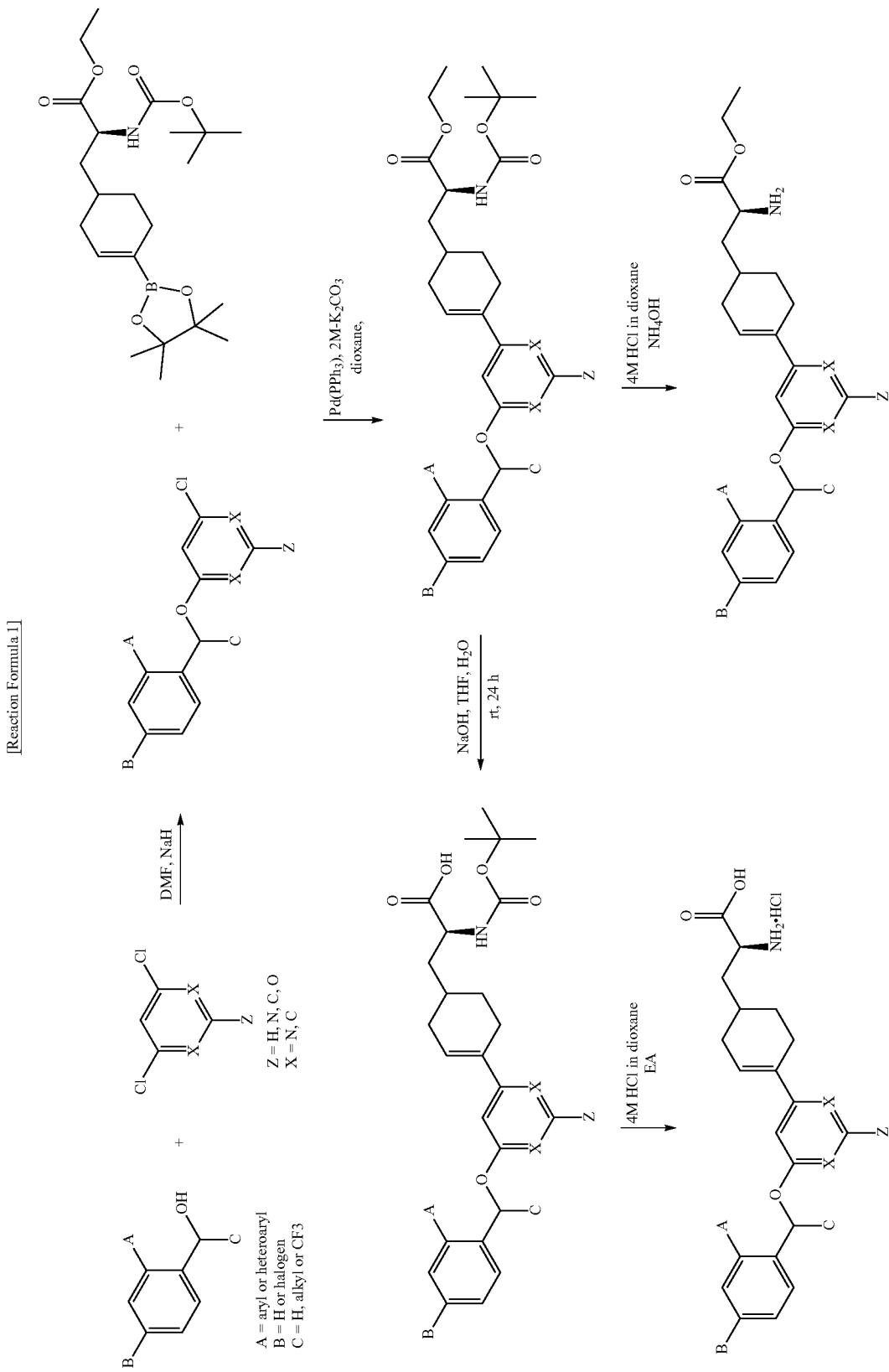

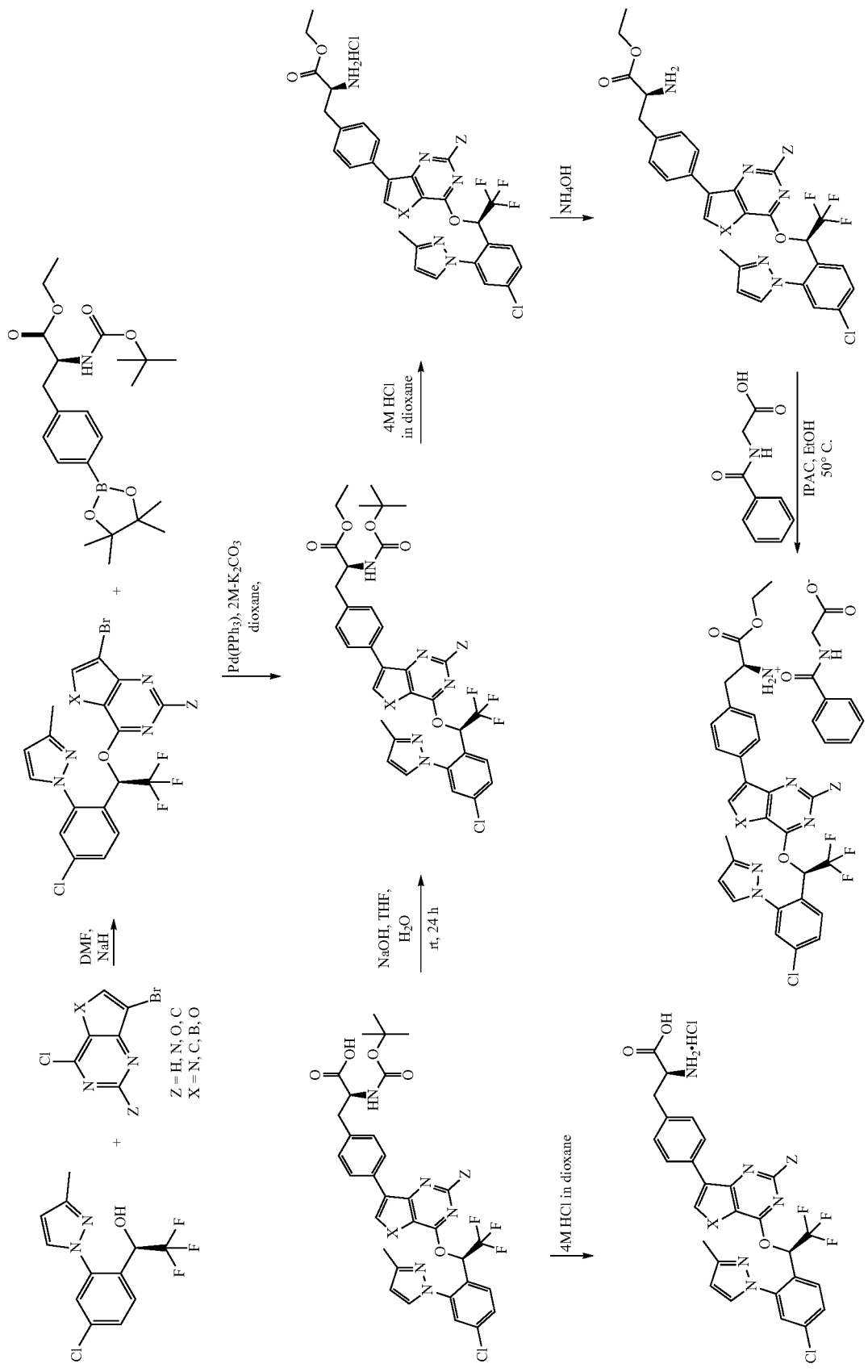

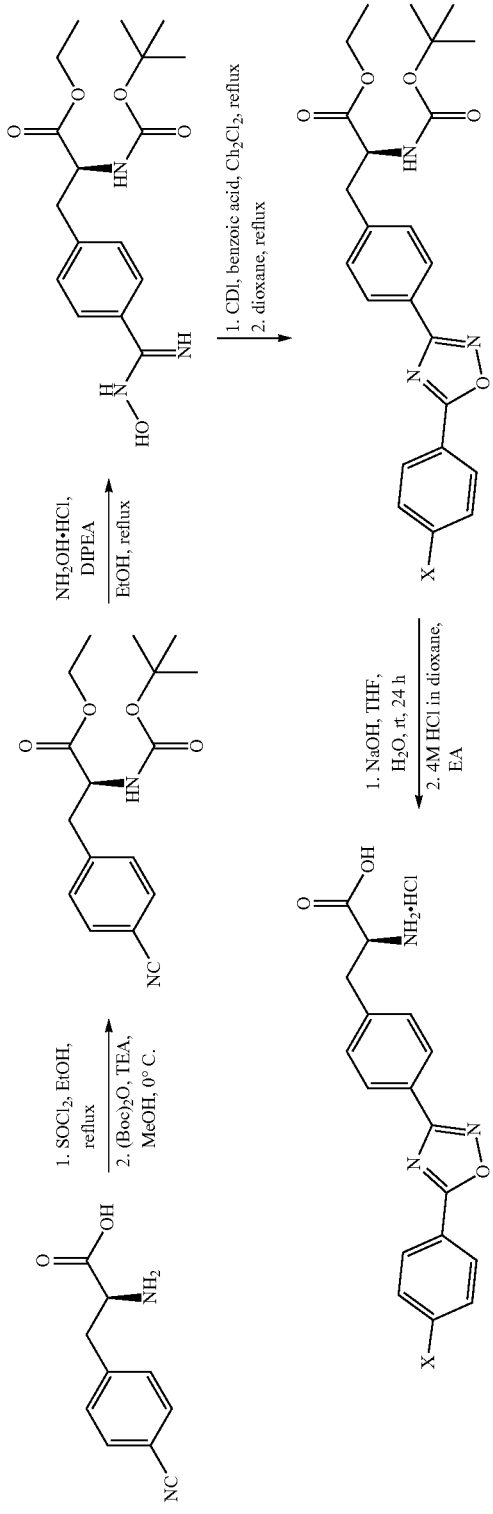
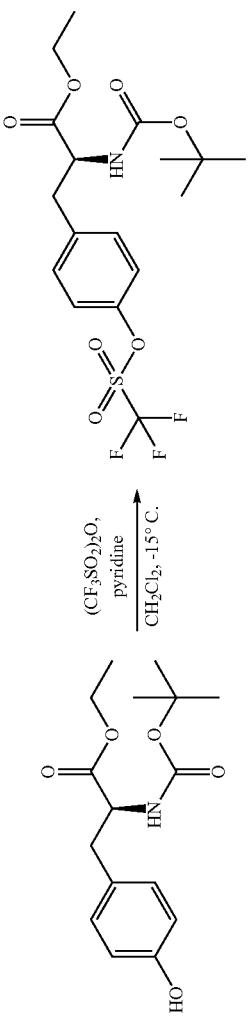
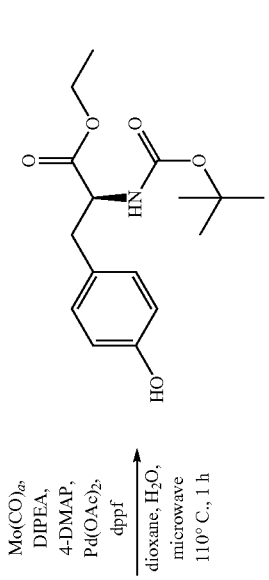
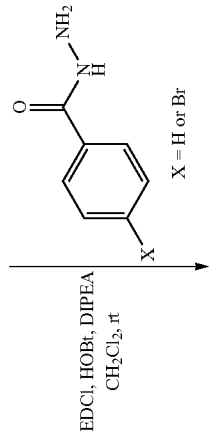

-continued
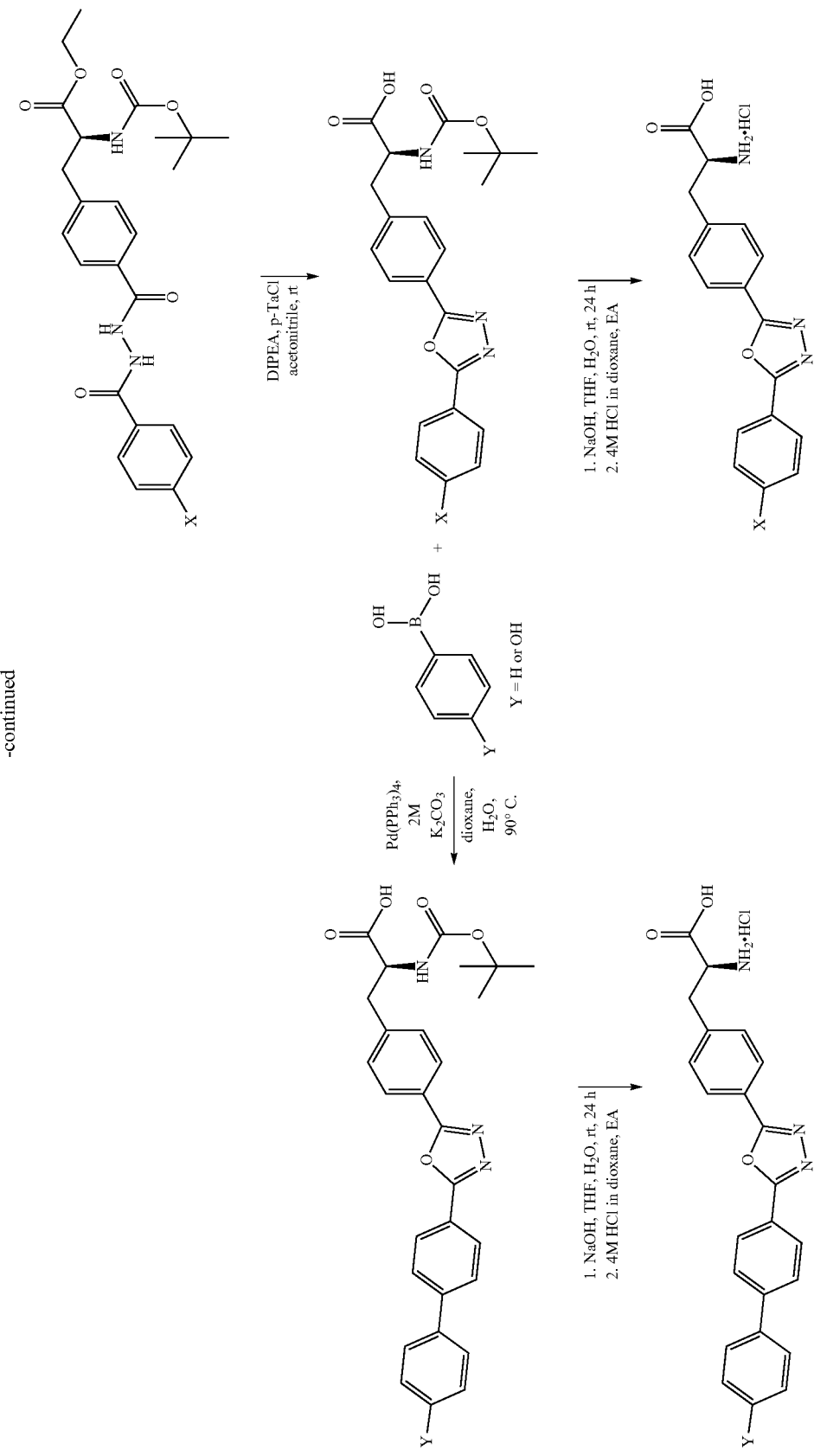

-continued
[Reaction Formula 5]
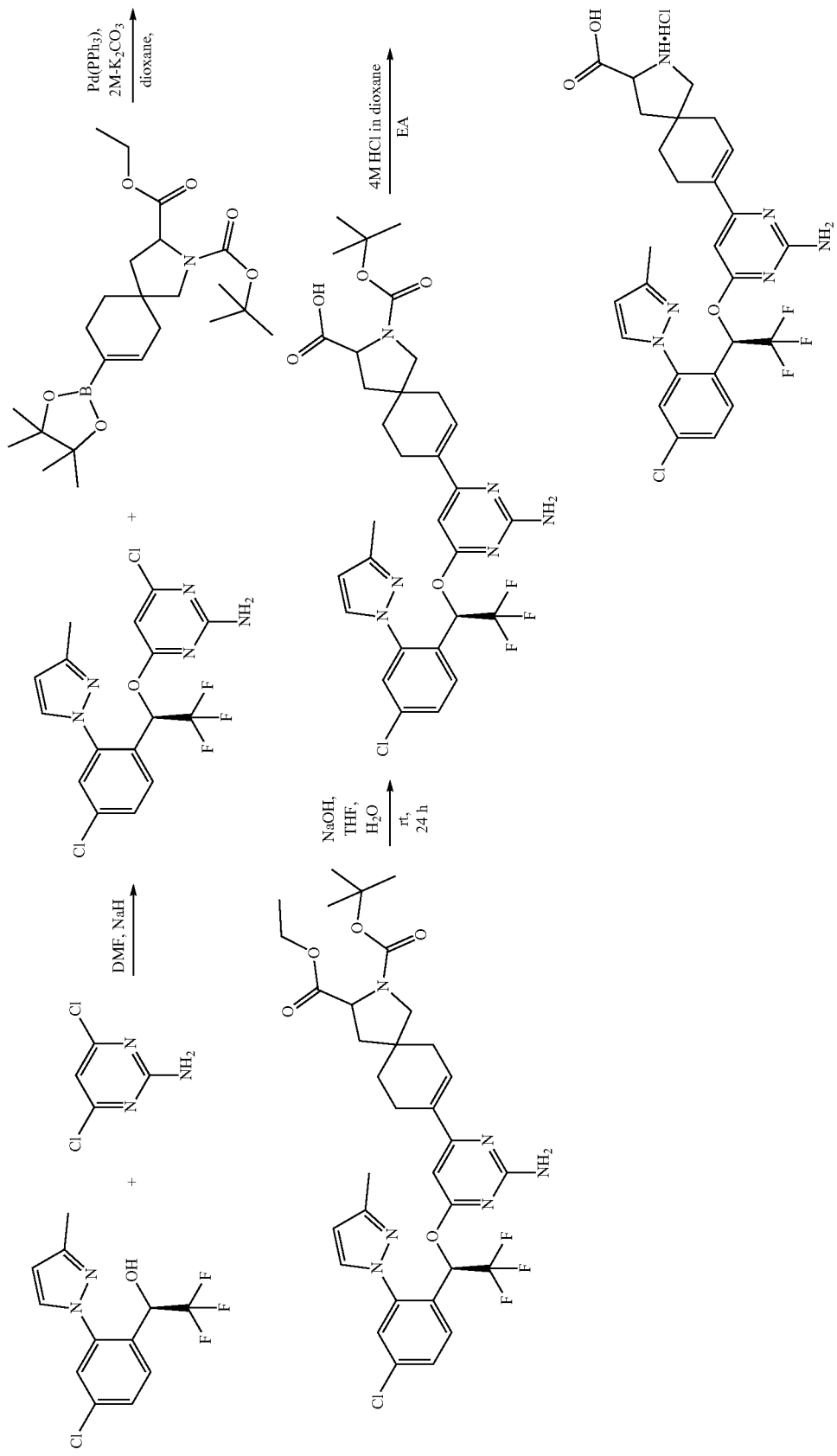

The preparation methods of reaction formulas 1 to can be performed according to the conditions in the reaction formulas, but not always limited thereto. The conditions can be used without limitation as long as they can derive the compound of the next step.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of metabolic disorder.

The metabolic disorder can be any one selected from the group consisting of obesity, diabetes mellitus, hyperlipidemia, arteriosclerosis, fatty liver, (nonalcoholic) fatty liver cirrhosis, (nonalcoholic) steatohepatitis, liver cirrhosis, celiac disease and hypertension.

The composition can further comprise a pharmaceutically acceptable carrier, an additive or an excipient.

The compound represented by formula 1 can inhibit tryptophan hydroxylase.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of cancer.

The cancer can be any one selected from the group consisting of colorectal cancer, breast cancer, ovarian cancer, carcinoid tumor and hepatocellular carcinoma.

The composition can further comprise a pharmaceutically acceptable carrier, an additive or an excipient.

The compound represented by formula 1 can inhibit tryptophan hydroxylase.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of digestive or circulatory system disorder.

The digestive or circulatory system disorder can be any one selected from the group consisting of hepatitis, enteritis, colitis, ulcerative enteritis, Crohn's disease, pheochromocytoma, irritable bowel syndrome, gastrointestinal bleeding, peptic ulcer, gastritis, inflammatory bowel disorder, pulmonary syndrome and pulmonary hypertension.

The composition can further comprise a pharmaceutically acceptable carrier, an additive or an excipient.

The compound represented by formula 1 can inhibit tryptophan hydroxylase.

Since the compound represented by formula 1 of the present invention, the novel tryptophan hydroxylase inhibitor, has an excellent inhibitory effect on TPH1 (Experimental Example 2), it can be effectively used for the prevention or treatment of metabolic disorders, cancers, and digestive or circulatory system disorders, which are the diseases related to TPH1 activity. In particular, since the compound has an excellent therapeutic effect on inflammatory bowel disorder (Experimental Example 3), it can be effectively used for the treatment of inflammatory bowel disorder.

At this time, the inflammatory bowel disorder can be any one selected from the group consisting of enteritis, colitis, ulcerative enteritis, Crohn's disease, pheochromocytoma, irritable bowel syndrome, gastrointestinal bleeding, peptic ulcer and gastritis.

The compound represented by formula 1 or the pharmaceutically acceptable salt thereof can be administered orally or parenterally and be used in general forms of pharmaceutical formulation. That is, the compound represented by formula 1 or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered parenterally and the parenteral administration includes subcutaneous injection, intravenous injection, intramuscular injection or intrathoracic injection.

To prepare the composition as a formulation for parenteral administration, the compound represented by formula 1 or the pharmaceutically acceptable salt thereof is mixed with a stabilizer or a buffering agent to produce a solution or a suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

In another aspect of the present invention, the present invention provides a health functional food comprising a compound represented by formula 1, an isomer thereof, a solvate thereof, a hydrate thereof or a pharmaceutically acceptable salt thereof as an active ingredient for the prevention or amelioration of metabolic disorder, cancer, digestive or circulatory system disorders.

The metabolic disorder can be any one selected from the group consisting of obesity, diabetes mellitus, hyperlipidemia, arteriosclerosis, fatty liver, (nonalcoholic) fatty liver cirrhosis, (nonalcoholic) steatohepatitis, liver cirrhosis, celiac disease and hypertension.

The cancer can be any one selected from the group consisting of colorectal cancer, breast cancer, ovarian cancer, carcinoid tumor and hepatocellular carcinoma.

The digestive or circulatory system disorder can be any one selected from the group consisting of hepatitis, enteritis, colitis, ulcerative enteritis, Crohn's disease, pheochromocytoma, irritable bowel syndrome, gastrointestinal bleeding, peptic ulcer, gastritis, inflammatory bowel disorder, pulmonary syndrome and pulmonary hypertension.

The compound represented by formula 1 according to the present invention can be used as a food additive. In that case, the compound can be added as it is or as mixed with other food components according to the conventional method. The mixing ratio of active ingredients can be regulated according to the purpose of use (prevention or amelioration). In general, to produce a health functional food, the compound is added preferably by 0.1-90 weight part. However, if long term administration is required for health and hygiene or regulating health condition, the content can be lower than the above but higher content can be accepted as well since the compound has been proved to be very safe.

The health beverages containing the composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. The composition for health beverages of the present invention can additionally include various flavors or natural carbohydrates, etc, like other beverages in addition to the compound. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g in 100 g of the composition of the present invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

In another aspect of the present invention, the present invention provides a method for preventing or treating metabolic disorder, cancer, digestive or circulatory system disorders, which comprises the step of administering a pharmaceutical composition or a health functional food comprising a compound represented by formula 1, an isomer thereof, a solvate thereof, a hydrate thereof or a pharmaceutically acceptable salt thereof as an active ingredient to a subject in need.

In another aspect of the present invention, the present invention provides a use of the pharmaceutical composition or the health functional food comprising a compound represented by formula 1 or a pharmaceutically acceptable salt thereof as an active ingredient for preventing or treating metabolic disorder, cancer, digestive or circulatory system disorders.

The term "tryptophan hydroxylase" used in the present invention means an enzyme involved in the synthesis of serotonin. The tryptophan hydroxylase hydroxylates tryptophan to produce 5-hydroxytryptophan.

Hereinafter, the present invention will be described in detail by the following examples and experimental examples.

However, the following examples and experimental examples are only for illustrating the present invention, and the contents of the present invention are not limited thereto.

<Preparative Example 1> Preparation of ethyl (tert-butoxycarbonyl)-L-tyrosinate

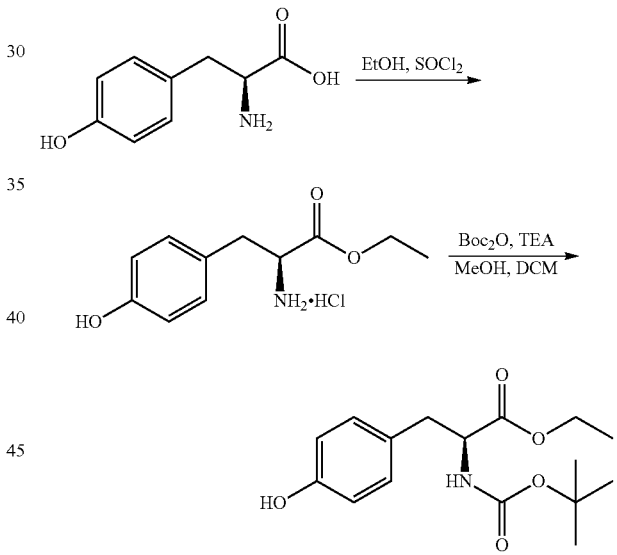

Step 1:
Thionyl chloride (100.1 mℓ, 1.38 mol) was added dropwise to a mixture of ethanol (800 mℓ) and L-tyrosine (100 g, 0.552 mol) at 0° C. The mixture was stirred at 0° C. for 60 minutes and then allowed to reach room temperature. The mixture was then heated to reflux overnight. The volatiles were removed in vacuo to give ethyl L-tyrosinate hydrochloride.

Step 2:
The obtained ethyl L-tyrosinate hydrochloride was dissolved in 100 mℓ of methanol and 800 mℓ of DCM with vigorous stirring. A solution of triethylamine (154 mℓ, 1.1 mol) and di-tert-butyl dicarbonate (120.5 g, 0.552 mol) in 200 mℓ of DCM was added sequentially at 0° C. The resulting suspension was stirred overnight at room temperature. Then, the suspension was filtered to remove solids and the filtrate was washed with water. The organic phase was dried over Na₂SO₄ and concentrated in vacuo to give ethyl (tert-butoxycarbonyl)-L-tyrosinate (136 g, 80%) as a white solid.

<Preparative Example 2> Preparation of ethyl (S)-2-((tert-butoxycarbonyl)amino)-3-(4-(4,4,5,5-tetramethyl-1,3,2-dioxaborolan-2-yl)phenyl)propanoate Step 1:

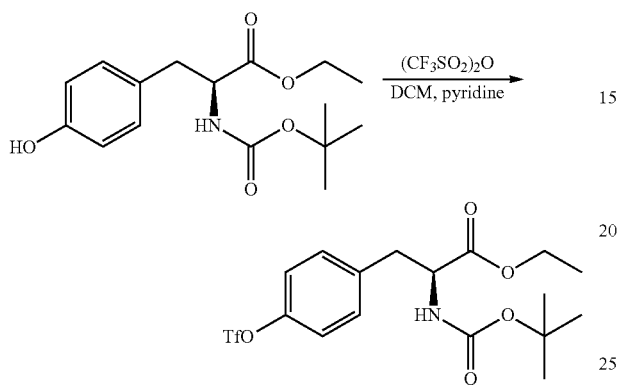

Triflic anhydride (25.1 mℓ, 0.149 mol) was added dropwise to 500 mℓ of DCM containing the ethyl (tert-butoxycarbonyl)-L-tyrosinate (44 g, 0.142 mol) prepared in Preparative Example 1 and pyridine (44.8 mℓ, 0.569 mol) at 0° C. The temperature of the mixture was warmed to ambient temperature and then the mixture was stirred for 1 hour. The mixture was poured into a saturated bicarbonate solution and extracted with DCM. The organic phase of the extract was washed with brine and then dried over anhydrous Na₂SO₄. The solvent was removed under reduced pressure, and the concentrate was purified with silica gel. As a result, (S)-2-((tert-butoxycarbonyl)amino)-3-(4-(((trifluoromethyl)sulfonyl)oxy)phenyl)propanoate (60 g, 95%) was obtained as a white solid.

Step 2:

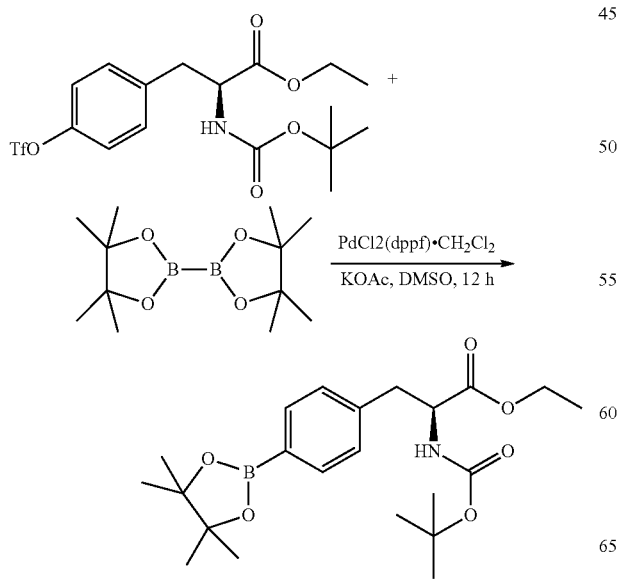

Bis(pinacolato)diboron (5.75 g, 22.67 mmol) and potassium acetate (6.675 g, 68.01 mmol) were added to 40 mℓ of DMSO containing the (S)-2-((tert-butoxycarbonyl)amino)-3-(4-(((trifluoromethyl)sulfonyl)oxy)phenyl)propanoate (10 g, 22.67 mmol). The temperature of the mixture was warmed to 40° C. and degassed. The mixture was then charged with PdCl₂(dppf).CH₂Cl₂ (331.75 mg, 0.453 mmol) and degassed. The mixture was heated at 100° C. for 12 hours and then left at room temperature overnight. The mixture was extracted with diethyl ether (4×200 mℓ). The combined organic materials were washed with water and brine, dried over anhydrous Na₂SO₄, filtered and concentrated. The concentrate was purified with silica gel. As a result, (S)-2-((tert-butoxycarbonyl)amino)-3-(4-(4,4,5,5-tetramethyl-1,3,2-dioxaborolan-2-yl)phenyl)propanoate (8 g, 84%) was obtained as a white solid.

<Preparative Example 3> Preparation of ethyl (2S)-2-((tert-butoxycarbonyl)amino)-3-(4-(4,4,5,5-tetramethyl-1,3,2-dioxaborolan-2-yl)cyclohex-3-ene-1-yl)propanoate Step 1:

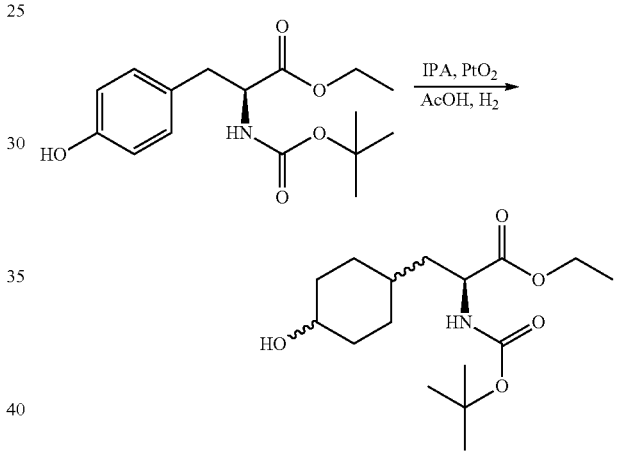

The ethyl (tert-butoxycarbonyl)-L-tyrosinate (30 g, 96.97 mmol) prepared in Preparative Example 1 was dissolved in 500 mℓ, of isopropanol and 38 mℓ of acetic acid, to which PtO₂ Adam's catalyst (595 mg, 2.6 mmol) was added. The mixture was stirred for 3 days under hydrogen atmosphere. The mixture was filtered through celite and washed with isopropanol. The solvent was removed in vacuo and the concentrate was purified by silica gel chromatography. As a result, (S)-2-((tert-butoxycarbonyl)amino)-3-(4-hydroxycyclohexyl)propanoate (18 g, 62%) was obtained as a white solid.

Step 2:

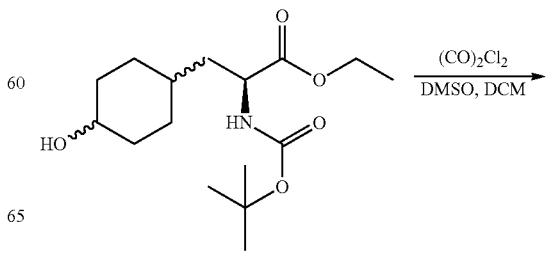

-continued

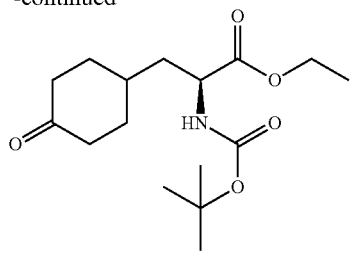

A solution of oxalyl dichloride (16 g, 50.7 mmol) in 150 ㎖ of anhydrous CH₂Cl₂ was cooled at −70° C. under nitrogen atmosphere. Then, a solution of dimethyl sulfoxide (15.13 ㎖, 0.213 mol) in 100 ㎖ of anhydrous DCM was added dropwise to the cooled mixture. The mixture was stirred at −70° C. for 1 hour. A solution containing ethyl (S)-2-((tert-butoxycarbonyl)amino)-3-(4-hydroxycyclohexyl)propanoate (16 g, 50.73 mmol) in 150 ㎖ of DCM was then added dropwise to the mixture. The mixture was stirred at −70° C. for 2 hours. Triethylamine (42.8 ㎖, 0.31 mol) was then added to the mixture. The mixture was gradually warmed to room temperature and stirred overnight. Upon completion of the reaction, concentrated NaHCO₃ was added to the mixture, which was then extracted with EtOAc. The extract was washed with water and brine, dried over anhydrous Na₂SO₄, filtered and concentrated. The concentrate was purified by silica gel chromatography. As a result, (S)-2-((tert-butoxycarbonyl)amino)-3-(4-oxocyclohexyl)propanoate (14 g, 88%) was obtained as an oil.

Step 3:

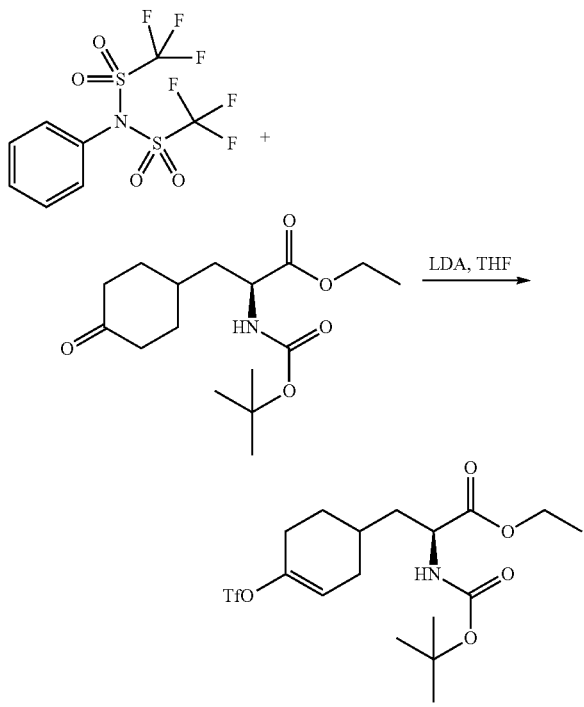

A solution containing Lithium diisopropylamide solution 2.0 M in THF/heptane/ethylbenzene (23.7 ㎖, 47.5 mmol) in 100 ㎖ of THF was cooled at −78° C. under dry nitrogen atmosphere. While maintaining the temperature at −78° C., a solution containing ethyl (S)-2-((tert-butoxycarbonyl)amino)-3-(4-oxocyclohexyl)propanoate (11.45 g, 36.54 mmol) in 110 ㎖ of anhydrous THF was added dropwise to the cooled solution. The mixture was stirred for 1 hour. Upon completion of the reaction, a solution containing 1,1,1-trifluoro-N-phenyl-N-((trifluoromethyl)sulfonyl)methanesulfonamide (13.7 g, 38.4 mmol) in 140 ㎖ of anhydrous THF was added dropwise to the mixture. The mixture was stirred at −78° C. for 4 hours and at room temperature for 24 hours. Upon completion of the reaction, saturated NaHCO₃ solution was added to the mixture, and the aqueous layer was extracted with EtOAc (3×200 ㎖). The organic phase of the extract was washed with brine, dried over anhydrous Na₂SO₄, filtered and concentrated. The concentrated crude material was purified by silica gel chromatography. As a result, ethyl (2S)-2-((tert-butoxycarbonyl)amino)-3-(4-(((trifluoromethyl)sulfonyl)oxy)cyclohex-3-ene-1-yl)propanoate (12.6 g, 77%) was obtained as an oil.

Step 4:

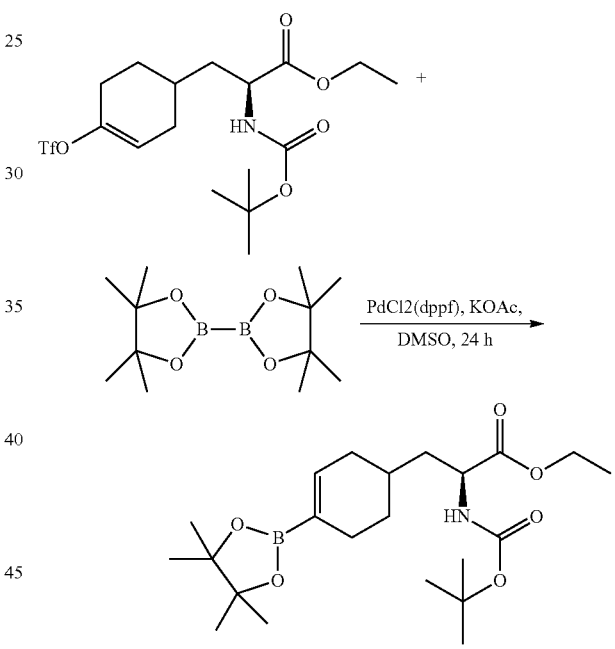

Bis(pinacolato)diboron (7.13 g, 28.06 mmol) and potassium acetate (8.3 g, 84.185 mmol) were added to a solution containing ethyl (2S)-2-((tert-butoxycarbonyl)amino)-3-(4-(((trifluoromethyl)sulfonyl)oxy)cyclohex-3-ene-1-㎖ yl) propanoate (12.5 g, 28.06 mmol) stirred in 490 ㎖ of DMSO. The temperature of the mixture was warmed to 40° C. and gas was removed. The mixture was then charged with PdCl₂ (dppf).CH₂Cl₂ (410.65 mg, 0.56 mmol) and degassed. The mixture was heated at 100° C. for 12 hours and then left at room temperature overnight. On the next day, the mixture was extracted with diethyl ether (4×200 ㎖). The combined organic materials were washed with water and brine, dried over anhydrous Na₂SO₄, filtered and concentrated. The concentrate was purified by silica gel chromatography. As a result, ethyl (2S)-2-((tert-butoxycarbonyl)amino)-3-(4-(4,4,5,5-tetramethyl-1,3,2-dioxaborolan-2-yl)cyclohex-3-ene-1-yl)propanoate (9.5 g, 80%) was obtained as an oil.

<Preparative Example 4> Preparation of di-tert-butyl (4-chloro-7H-pyrrolo[2,3-d]pyrimidine-2-yl)-imidodicarbonate

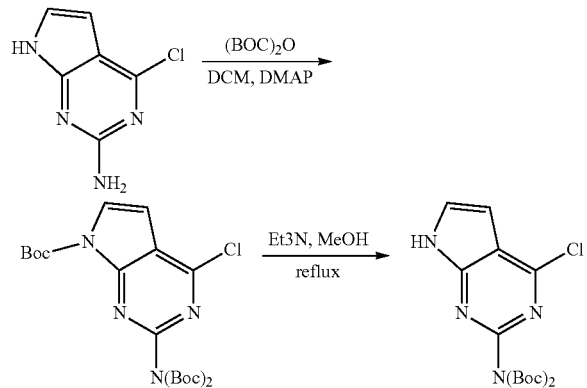

Step 1:
Di-tert-butyl dicarbonate (6.84 g, 31.32 mmol) and 4-dimethylaminopyridine (220 mg, 1.8 mmol) were added to a solution containing 4-chloro-7H-pyrrolo [2,3-d] pyrimidine-2-amine (1320 mg, 7.83 mmol) in 60 ㎖ of acetonitrile/DCM (1:1). The mixture was stirred at room temperature for 18 hours and concentrated. Then, the concentrated mixture was purified by column chromatography. As a result, tert-butyl 2-[bis(tert-butoxycarbonyl)amino]-4-chloro-7H-pyrrolo[2,3-d]pyrimidine-7-carboxylate (1.9 g, 52%) was obtained as a white solid.

Step 2:
Triethyl amine (4.5 g, 44.57 mmol) was added to a solution containing the tert-butyl 2-[bis(tert-butoxycarbonyl)amino]-4-chloro-7H-pyrrolo[2,3-d]pyrimidine-7-carboxylate (1.9 g, 4.05 mmol) obtained above in 14 ㎖ of methanol at room temperature. The mixture was stirred at 60° C. for 5 hours and concentrated. Then, the concentrated mixture was purified by column chromatography. As a result, di-tert-butyl (4-chloro-7H-pyrrolo[2,3-d]pyrimidine-2-yl)-imidodicarbonate (1.3 g, 87%) was obtained as a white solid.

<Preparative Example 5> Preparation of 2-(tert-butyl) 3-ethyl 8-(4,4,5,5-tetramethyl-1,3,2-dioxaborolan-2-yl)-2-azaspiro[4.5]dec-7-ene-2,3-dicarboxylate

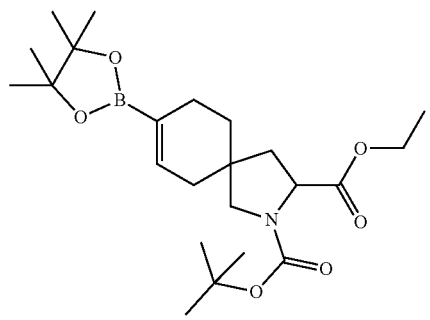 [SMILES: CCOC(=O)C1CC2(CC=C(B3OC(C)(C)C(C)(C)O3)CC2)CN1C(=O)OC(C)(C)C]

Step 1:
Ethyl 8-((tert-butyldimethylsilyl) oxy)-2-azaspiro [4.5] decane-3-carboxylate (4 g, 11.71 mol) in dichloromethane (80 mL) was stirred vigorously at room temperature. DCM (80 mL) containing triethylamine (2.37 g, 23.42 mmol) and di-tert-butyl dicarbonate (3.07 g, 14.05 mmol) was added thereto sequentially at 0° C. The reaction suspension was stirred at room temperature overnight. The concentrate obtained by evaporating the reaction mixture was purified by silica gel column chromatography. As a result, 2-(tert-butyl) 3-ethyl 8-((tert-butyldimethylsilyl)oxy)-2-azaspiro[4.5]decane-2,3-dicarboxylate was obtained as a colorless oil.

Step 2:
1.0 M THF (40 mL) containing tetrabutylammonium fluoride was added to a solution containing 2-(tert-butyl) 3-ethyl 8-((tert-butyldimethylsilyl) oxy)-2-azaspiro [4.5] decane-2,3-dicarboxylate in tetrahydrofuran (100 mL). The reaction mixture was stirred at room temperature for 24 hours. The concentrate obtained by evaporating the reaction mixture was purified by silica gel column chromatography. As a result, 2-(tert-butyl) 3-ethyl 8-hydroxy-2-azaspiro [4.5] decane-2,3-dicarboxylate (3.8 g, 99%, two-step yield) was obtained as a yellow oil.

Step 3:
A solution of oxalyl dichloride (2.05 mL, 23.91 mmol) in dry $CH_2Cl_2$ (150 mL) was cooled to −70° C. under nitrogen atmosphere. A dry DCM (100 mL) solution containing dimethyl sulfoxide (3.46 mL, 48.75 mmol) was added dropwise to the cooled solution, and the mixture was stirred at −70° C. for 2 hours. 2-(Tert-butyl) 3-ethyl 8-hydroxy-2-azaspiro [4.5] decane-2,3-dicarboxylate (3.8 g, 11.61 mmol) in dry DCM (150 mL) was added dropwise to the mixture above, and the mixture was stirred at −70° C. for 6 hours. Sequentially, triethylamine (9.8 mL, 70.22 mmol) was added to the mixture above. The mixture was slowly heated to room temperature and stirred overnight. Saturated $NaHCO_3$ was added to the solution, which was extracted with EtOAc. The extract was washed with $H_2O$ and brine, dried over anhydrous $Na_2SO_4$, filtered, and concentrated. The concentrate was purified by silica gel column chromatography. As a result, 2-(tert-butyl) 3-ethyl 8-oxo-2-azaspiro[4.5]decane-2,3-dicarboxylate (3.2 g, 84%) was obtained as a yellow oil.

Step 4:
2-(Tert-butyl) 3-ethyl 8-(((trifluoromethyl)sulfonyl)oxy)-2-azaspiro[4.5]dec-7-ene-2,3-dicarboxylate (2.6 g, 58%) was obtained as an oil by performing the similar method described in step 3 of Preparative Example 3.

Step 5:
2-(Tert-butyl) 3-ethyl 8-(4,4,5,5-tetramethyl-1,3,2-dioxaborolan-2-yl)-2-azaspiro[4.5]dec-7-ene-2,3-dicarboxylate (2.0 g, 88%) was obtained as a colorless oil by performing the similar method described in step 4 of Preparative Example 3.

<Preparative Example 6> Preparation of (R)-1-(4-chloro-2-(5,6-dihydro-2H-pyran-3-yl)phenyl)-2,2,2-trifluoroethane-1-ol

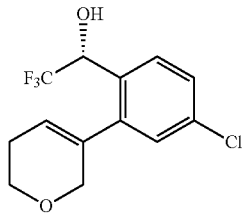 [SMILES: O[C@H](c1ccc(Cl)cc1C1=CCCOC1)C(F)(F)F]

A mixture of (R)-1-(2-bromo-4-chlorophenyl)-2,2,2-trifluoroethane-1-ol (500 mg, 1.727 mmol), 2-(5,6-dihydro-2H-pyran-3-yl)-4,4,5,5-tetramethyl-1,3,2-dioxaborolan (399.14 mg, 4.28 mmol), 2 M potassium carbonate solution (954.85 mg, 6.91 mmol) and Pd(PPh₃)₄ (99.80 mg, 0.086 mmol) in dioxane (10 mL) was reacted in a single-mode microwave instrument (Biotage Initiator 2.5) at 80° C. for 30 minutes. The reaction mixture was poured into brine and extracted with ethyl acetate. The combined organic layers were dried over anhydrous sodium sulfate and concentrated in vacuo. The concentrate was purified by silica gel column chromatography. As a result, (R)-1-(4-chloro-2-(5,6-dihydro-2H-pyran-3-yl)phenyl)-2,2,2-trifluoroethane-1-ol (390 mg, 77%) was obtained as a yellow solid.

Hereinafter, the preparation methods of the example compounds of the present invention are explained.

<Example 8> Preparation of (S)-2-amino-3-(4-(4-((R)-1-(4-chloro-2-(3-methyl-1H-pyrazol-1-yl)phenyl)-2,2,2-trifluoroethoxy)thieno[3,2-d]pyrimidine-7-yl)phenyl)propionic acid hydrochloride Step 1:

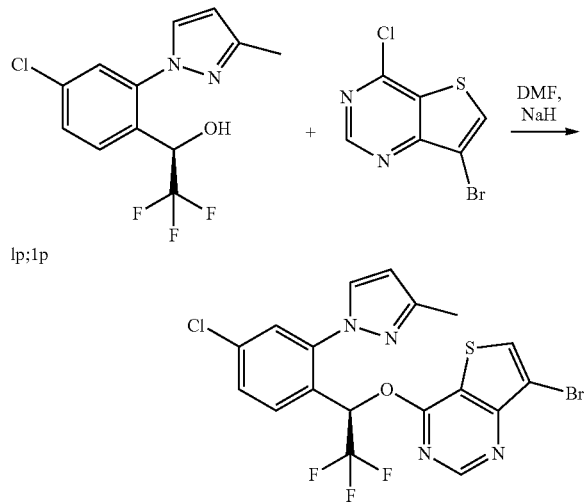

(R)-1-(4-chloro-2-(3-methyl-1H-pyrazol-1-yl)phenyl)-2,2,2-trifluoroethane-1-ol (900 mg, 3.096 mmol) was dissolved in 4 ㎖ of N,N-dimethylformamide and then cooled to 0° C. Oil containing 60% sodium hydride (v/v) was added to the mixture, which was stirred for 60 minutes. Then, 7-bromo-4-chloro-thieno [3,2-d] pyrimidine (811.18 mg, 3.25 mmol) was added to the mixture, followed by warming to room temperature, which was stirred for 12 hours. Upon completion of the reaction, the mixture was cooled rapidly with aqueous ammonium chloride and extracted twice with ethyl acetate. The organic layer of the extract was washed with water and brine, dried over anhydrous sodium sulfate, and then concentrated under reduced pressure to obtain a foam concentrate. The concentrate was purified by column chromatography. As a result, (R)-7-bromo-4-(1-(4-chloro-2-(3-methyl-1H-pyrazol-1-yl)phenyl)-2,2,2-trifluoroethoxy) thieno[3,2-d]pyrimidine (1.5 g, 96%) was obtained.

Step 2:

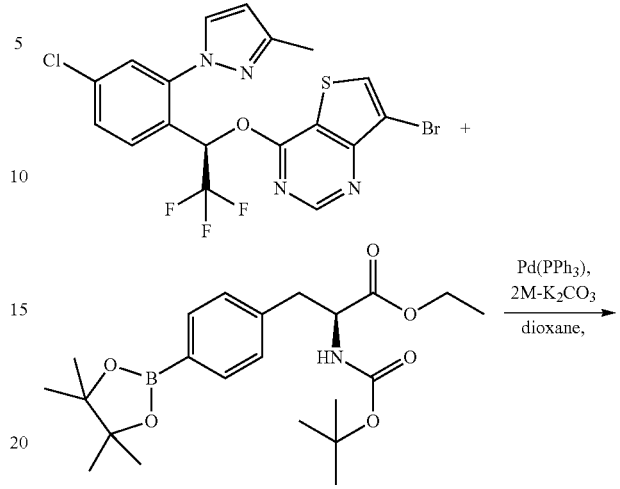

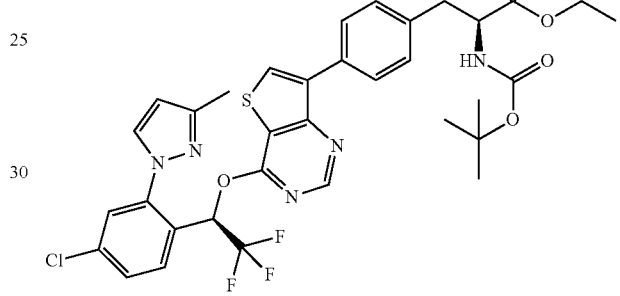

(R)-7-bromo-4-(1-(4-chloro-2-(3-methyl-1H-pyrazol-1-yl)phenyl)-2,2,2-trifluoroethoxy)thieno[3,2-d]pyrimidine (1.5 g, 2.978 mmol) was added to 25 ㎖ of 1,4-dioxane. Then, ethyl ㎖ (S)-2-((tert-butoxycarbonyl)amino)-3-(4-(4,4,5,5-tetramethyl-1,3,2-dioxaborolan-2-yl)phenyl)propanoate (1.37 g, 3.26 mmol), tetrakis (triphenylphosphine) palladium (172.06 mg, 0.149 mmol), potassium carbonate (823.11 mg, 5.96 mmol) and water (8 ㎖ ) were added ㎖ sequentially to the mixture with stirring. The mixture was heated to 90° C., followed by stirring at 90° C. for 3 hours. After the reaction was terminated using brine, the mixture was extracted twice with ethyl acetate. The organic layer collected from the extract was dried over anhydrous sodium sulfate, and then concentrated under reduced pressure. The concentrate was purified by column chromatography. As a result, ethyl (S)-2-((tert-butoxycarbonyl)amino)-3-(4-(4-((R)-1-(4-chloro-2-(3-methyl-1H-pyrazol-1-yl)phenyl)-2,2,2-trifluoroethoxy)thieno[3,2-d]pyrimidine-7-yl)phenyl)propanoate (1.5 g, 70%) was obtained.

Step 3:

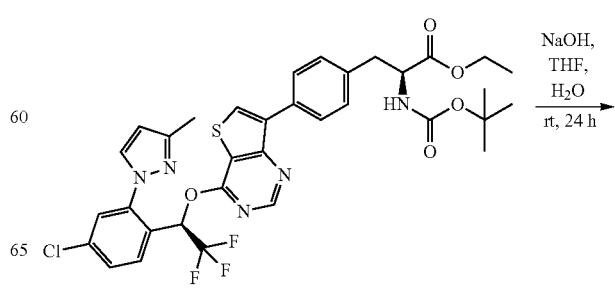

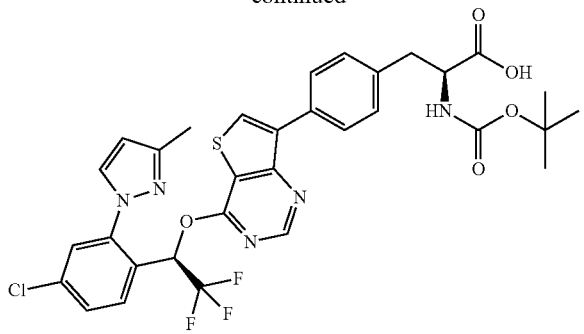

NaOH (50.27 mg, 1.26 mmol) was added to a solution of (S)-2-((tert-butoxycarbonyl)amino)-3-(4-(4-((R)-1-(4-chloro-2-(3-methyl-1H-pyrazole-1-yl)phenyl)-2,2,2-trifluoroethoxy)thieno[3,2-d]pyrimidine-7-ml yl)phenyl)propanoate (180 mg, 0.251 mmol) in 50 ml of THF/water (3:1). The mixture was stirred at ambient temperature for 24 hours. Upon completion of the reaction, THF was removed from the mixture in vacuo. The mixture was acidified to pH 4 with 1 N hydrochloric acid. 50 ml of water was additionally added to the mixture, which was extracted three times with EtOAc (50 ml). The mixed organic layer of the extract was washed with brine, dried over sodium sulfate and concentrated. The concentrate was purified by column chromatography. As a result, (S)-2-((tert-butoxycarbonyl)amino)-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid was obtained.

Step 4:

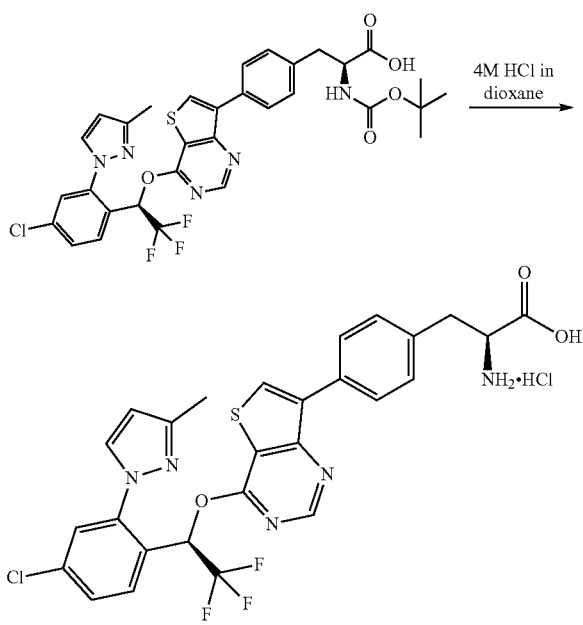

A solution of 4.0 M HCl in 1,4 dioxane (5 ml) was added to a solution containing (S)-2-((tert-butoxycarbonyl)amino)-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid in 10 ml of ethyl acetate. The mixture was then stirred for 12 hours. Upon completion of the reaction, the mixture was concentrated to the minimum volume and the concentrate was collected by filtration. As a result, (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride (121 mg, 77%) was obtained as a light gray solid.

The compounds of Examples 9, 10, 13-20, 22, 24-27, 30, 35, 46, 50, 51, 69, 72, 73, 78, 81, 103 and 104 were prepared by performing the method similar to the preparation method of Example 8.

<Example 12> Preparation of (S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride Step 1:

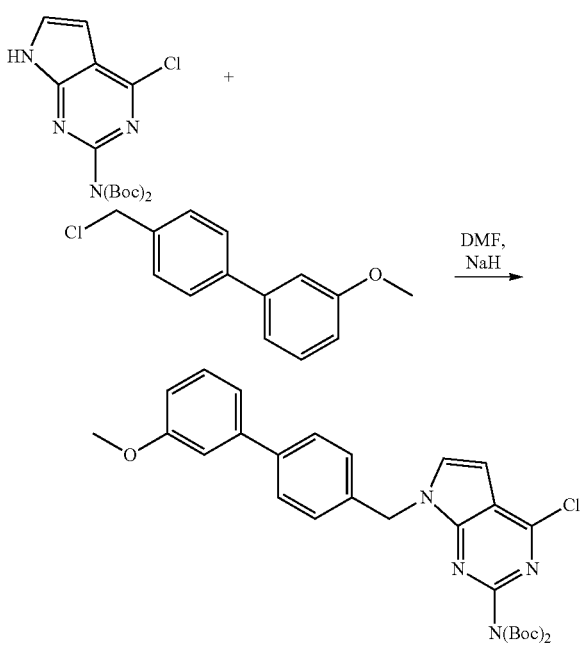

Di-tert-butyl (4-chloro-7H-pyrrolo[2,3-d]pyrimidine-2-yl)-imidodicarbonate (300 mg, 0.913 mmol) was dissolved in 2 ml of N,N-dimethylformamide, which was cooled to 0° C. Oil containing 60% sodium hydride (v/v) (48.8 mg, 1.22 mmol) was added to the mixture, followed by stirring for 30 minutes. 4'-(Chloromethyl)-3-methoxy-1,1'-biphenyl (208.22 g, 0.895 mmol) was added to the mixture, followed by stirring for 20 minutes. Upon completion of the reaction, the mixture was cooled rapidly with aqueous ammonium chloride and extracted twice with ethyl acetate. The organic layer of the extract was washed with water and brine, dried over anhydrous sodium sulfate, and then concentrated under reduced pressure. As a result, di-tert-butyl (4-chloro-7-((3'-methoxy-[1,1'-biphenyl]-4-yl)methyl)-7H-pyrrolo[2,3-d]pyrimidine-2-yl)-imidodicarbonate (381 mg, 83%) was obtained.

Step 2:

(S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride (150 mg, 78%) was obtained as a yellow solid by performing the similar method described in steps 2 to 4 of Example 8.

The compounds of Examples 1-7, 11, 21, 23, 33, 55 and 56 were prepared by performing the method similar to the preparation method of Example 12.

<Example 28> Preparation of ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate

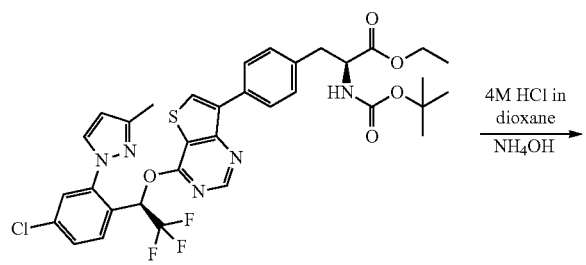

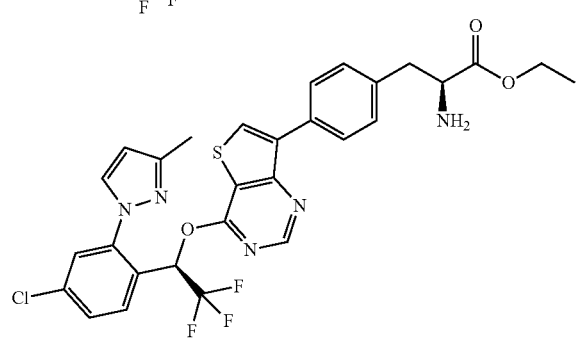

A solution of 4.0 M HCl in 1,4 dioxane (10 ㎖) was added to a solution containing ethyl (S)-2-((tert-butoxycarbonyl)amino)-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate (1.2 g, 1.676 mmol) in 20 ㎖ of ethyl acetate. The mixture was then stirred for 12 hours. Upon completion of the reaction, the mixture was concentrated, and the concentrate was dissolved in water. The pH of the dissolved concentrate was adjusted to 8 with ammonia water, followed by extracting with ethyl acetate. The organic layer of the extract was dried over anhydrous sodium sulfate and concentrated in vacuo. The concentrate was purified by silica gel column chromatography. As a result, ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate (910 mg, 88%) was obtained as a white solid.

The compounds of Examples 57 and 70 were prepared by performing the method similar to the preparation method of Example 28.

<Example 29> Preparation of ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate hippurate

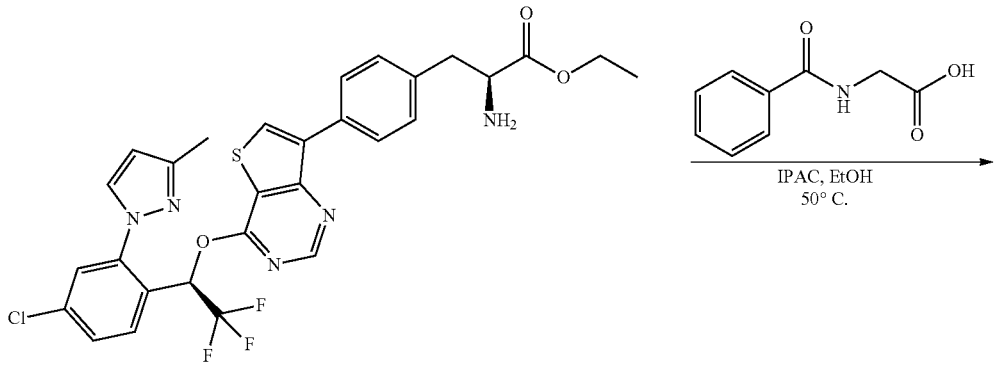

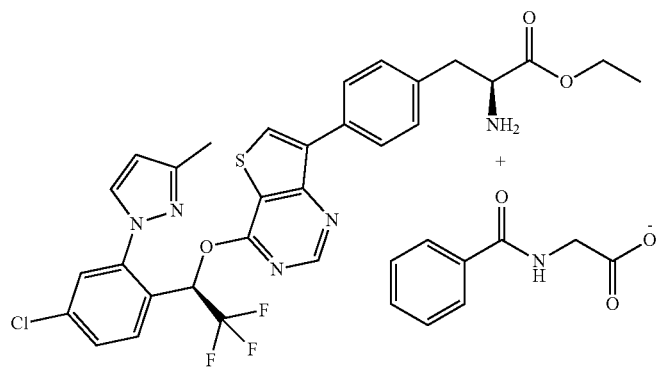

A solution containing hippuric acid thin slurry (95.98 mg, 0.536 mmol) in 5 ml of IPAc and 1 ml of EtOH were added to ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate (330 mg, 0.536 mmol), followed by stirring at 60° C. for 12 hours. Upon completion of the reaction, the resulting suspension was slowly cooled to room temperature, followed by stirring at room temperature for 12 hours. The solid generated from the suspension was filtered, washed with IPAc and dried. As a result, ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoate hippurate was obtained as a solid.

The compound of Example 120 was prepared by performing the method similar to the preparation method of Example 29.

<Example 31> Preparation of (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride Step 1:

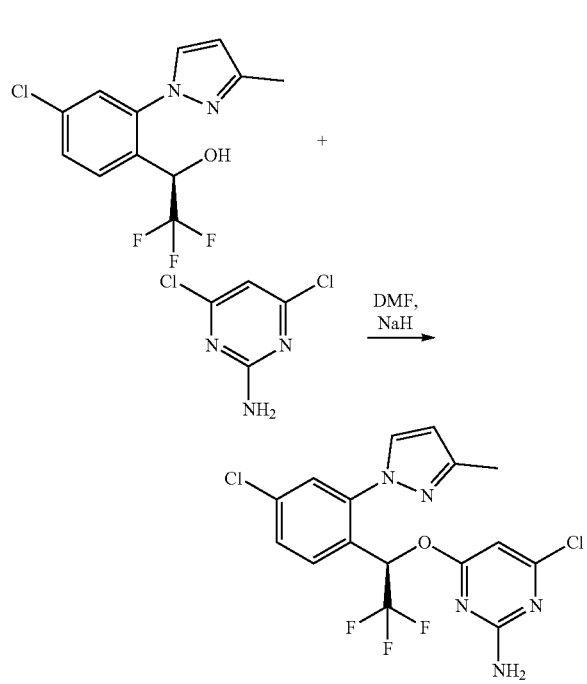

(R)-1-(4-chloro-2-(3-methyl-1H-pyrazole-1-yl)phenyl)-2,2,2-trifluoroethane-1-ol (1.8 g, 6.193 mmol) was dissolved in 4 ml of N,N-dimethylformamide, which was cooled to 0° C. Oil containing 60% (v/v) sodium hydroxide (297.2 mg, 7.43 mmol) was added to the mixture, followed by stirring for 60 minutes. Upon completion of the reaction, 4,6-dichloropyrimidine-2-amine (1.026 g, 3.25 mmol) was added to the mixture, followed by warming to room temperature, which was stirred for 12 hours. Then, the mixture was cooled rapidly with aqueous ammonium chloride and extracted twice with ethyl acetate. The organic layer of the extract was washed with water and brine, dried over anhydrous sodium sulfate, and then concentrated under reduced pressure. The concentrate was purified by column chromatography. As a result, (R)-4-chloro-6-(1-(4-chloro-2-(3-methyl-1H-pyrazole-1-yl)phenyl)-2,2,2-trifluoroethoxy)pyrimidine-2-amine (2.1 g, 81%) was obtained.

Step 2:

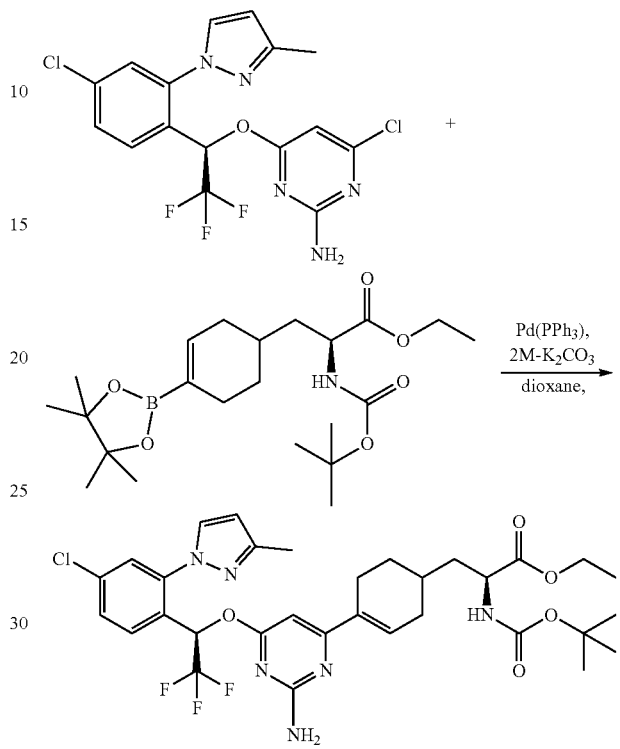

(R)-4-chloro-6-(1-(4-chloro-2-(3-methyl-1H-pyrazole-1-yl)phenyl)-2,2,2-trifluoroethoxy)pyrimidine-2-amine (1.5 g, 2.978 mmol) was added to 25 ml of 1,4 dioxane. Then, ethyl (2S)-2-((tert-butoxycarbonyl)amino)-3-(4-(4,4,5,5-tetramethyl-1,3,2-dioxaborolan-2-yl)cyclohex-3-ene-1-yl)propanoate (1.67 g, 3.945 mmol), tetrakis (triphenylphosphine) palladium (207.24 mg, 0.179 mmol), potassium carbonate (991.43 mg, 7.174 mmol) and water (8 ml) were added sequentially to the mixture with stirring. The mixture was heated to 90° C., followed by stirring at 90° C. for 3 hours. After the reaction was terminated using brine, the mixture was extracted twice with ethyl acetate. The organic layer collected from the extract was dried over anhydrous sodium sulfate, and then concentrated. The concentrate was purified by column chromatography. As a result, (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propanoate (2 g, 82%) was obtained.

Step 3:

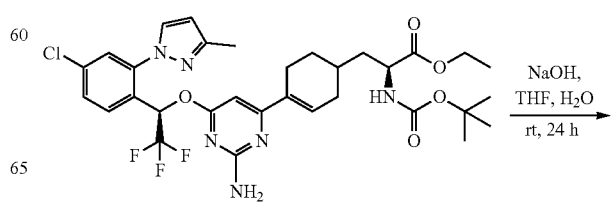

-continued

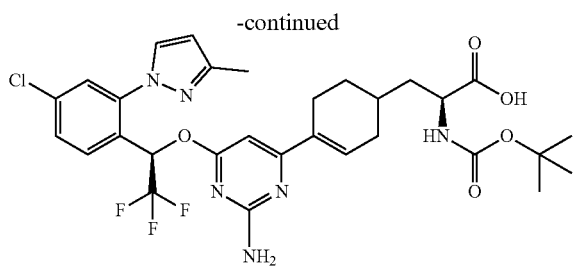

NaOH (441.74 mg, 11.04 mmol) was added to a solution of ethyl (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propanoate (1.5 g, 2.209 mmol) in 150 ml of THF/water (3:1). The mixture was stirred at ambient temperature for 24 hours. Upon completion of the reaction, THF was removed from the mixture in vacuo. The mixture was acidified to pH 4 with 1 N hydrochloric acid. 100 ml of water was additionally added to the mixture, which was extracted three times with EtOAc (50 ml). The mixed organic layer of the extract was washed with brine, dried over sodium sulfate and concentrated. The concentrate was purified by column chromatography. As a result, ((2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionic acid (1.2 g, 83%) acid was obtained.

Step 4:

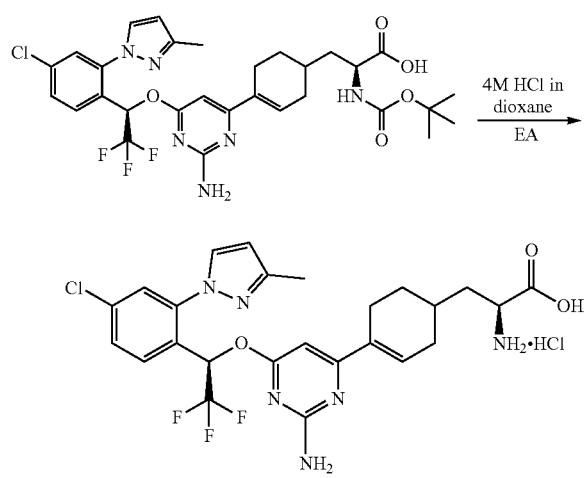

A solution of 4.0 M HCl in 1,4 dioxane (10 ml) was added to a solution containing (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionic acid (1.2 g, 1.843 mmol) in 20 ml of ethyl acetate. The mixture was then stirred for 12 hours. Upon completion of the reaction, the mixture was concentrated to the minimum volume and the concentrate was collected by filtration. As a result, (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride (950 mg, 87%) was obtained as a white solid.

The compounds of Examples 32, 34, 47-49, 54, 60-66, 71, 74-77, 82, 85, 86, 90 and 97-102 were prepared by performing the method similar to the preparation method of Example 31.

The compounds of Examples 53, 59, 86 and 96 were prepared by performing steps 1 and 2 in the preparation method of Example 31, and the preparation method of Example 28, followed by performing the preparation method of Example 29.

The compound of Example 44 was prepared by performing the method similar to the preparation method of Example 31, without performing step 4.

<Example 36> Preparation of ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propanoate

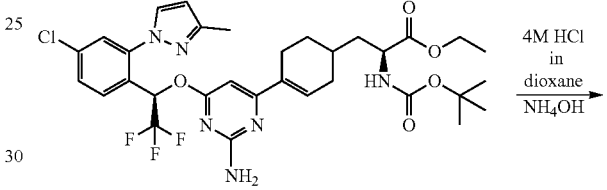

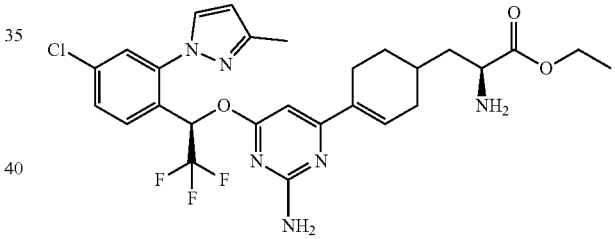

A solution of 4.0 M HCl in 1,4 dioxane (10 ml) was added to a solution containing ethyl (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propanoate (400 mg, 0.598 mmol) in 20 ml of ethyl acetate. The mixture was then stirred for 12 hours. Upon completion of the reaction, the mixture was concentrated, and the concentrate was dissolved in water. The pH of the dissolved concentrate was adjusted to 8 with ammonia water, followed by extracting with ethyl acetate. The organic layer of the extract was dried over anhydrous sodium sulfate and concentrated in vacuo. The concentrate was purified by silica gel column chromatography. As a result, ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propanoate (295 mg, 86%) was obtained as a white solid.

The compounds of Examples 45, 55, 58, 67, 68, 85 and 92 were prepared by performing the method similar to the preparation method of Example 36.

<Example 79> Preparation of 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride

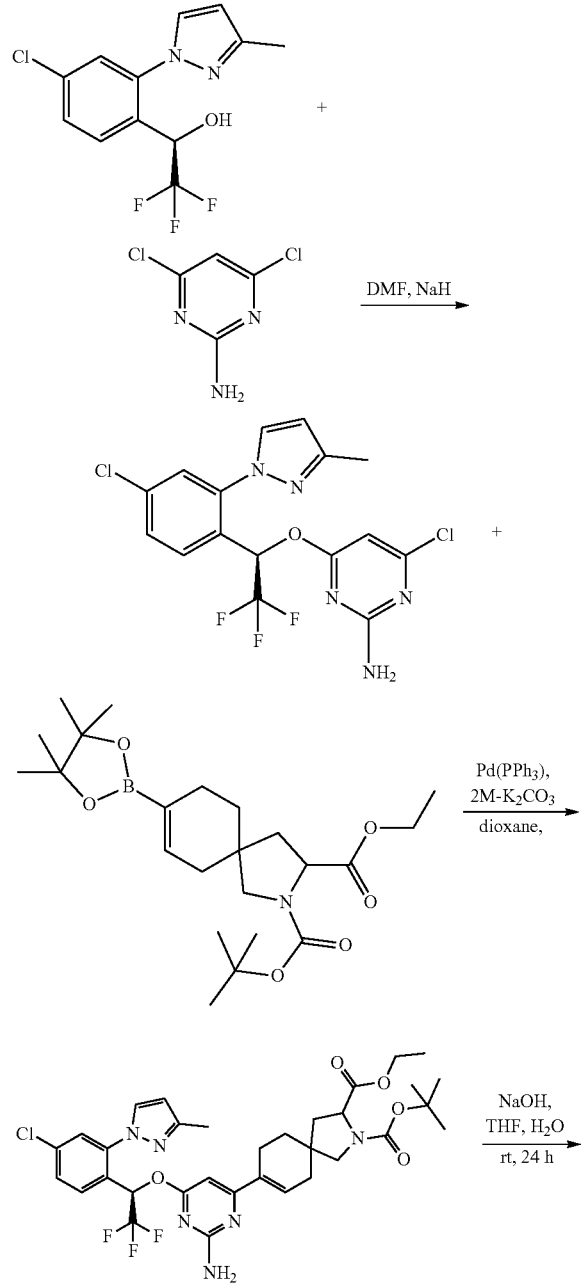

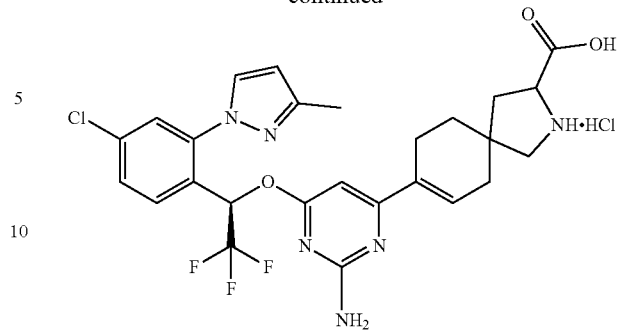

Step 1:
(R)-1-(4-chloro-2-(3-methyl-1H-pyrazole-1-yl)phenyl)-2,2,2-trifluoroethane-1-ol (1.8 g, 6.193 mmol) was dissolved in 4 ml of N,N-dimethylformamide, which was cooled to 0° C. Oil containing 60% sodium hydride (297.2 mg, 7.43 mmol) was added to the mixture, which was stirred for 60 minutes. Then, 4,6-dichloropyrimidine-2-amine (1.026 g, 3.25 mmol) was added to the mixture, followed by warming to room temperature, which was stirred for 12 hours. The reaction mixture was quenched with aqueous ammonium chloride solution and extracted twice with ethyl acetate. The organic layer was washed with water and brine, dried over anhydrous sodium sulfate, and then concentrated under reduced pressure. The concentrate was purified by column chromatography. As a result, the target compound (R)-4-chloro-6-(1-(4-chloro-2-(3-methyl-1H-pyrazole-1-yl)phenyl)-2,2,2-trifluoroethoxy)pyrimidine-2-amine (2.1 g, 81%) was obtained.

Step 2:
8-(2-Amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride was obtained as a white solid by performing the method similar to steps 2 to 4 of Example 8.

The compounds of Examples 83, 84, 87, 88, 93, 94 and 107-117 were prepared by performing the method similar to the preparation method of Example 79.

The compounds of Examples 118 and 119 were prepared by performing steps 1 to 3 in the preparation method of Example 79, and the preparation method of Example 28, followed by performing the preparation method of Example 29.

<Example 80> Preparation of 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid

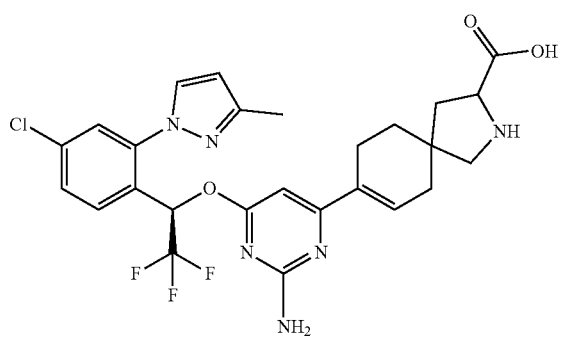

The pH of 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride (30 mg, 0.05 mmol) in water (2 mL) was adjusted to 7 with ammonia water. The reaction mixture was stirred at room temperature overnight. The resulting solid was filtered, washed with water and dried. As a result, 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid (20 mg, 71%) was obtained.

The compounds of Examples 89 and 95 were prepared by performing the method similar to the preparation method of Example 80.

<Example 91> Preparation of (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride

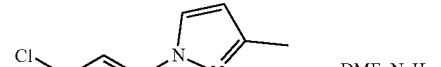
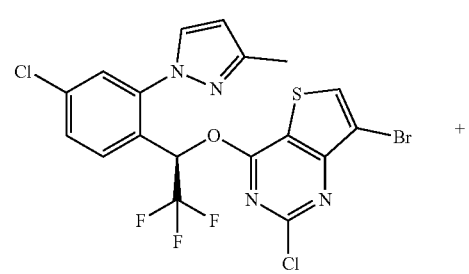
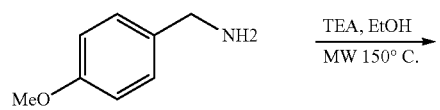
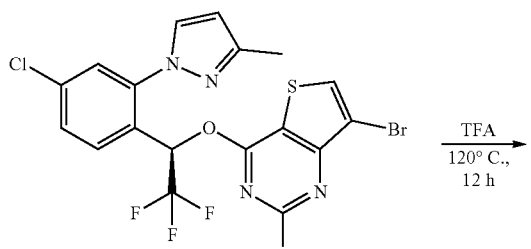
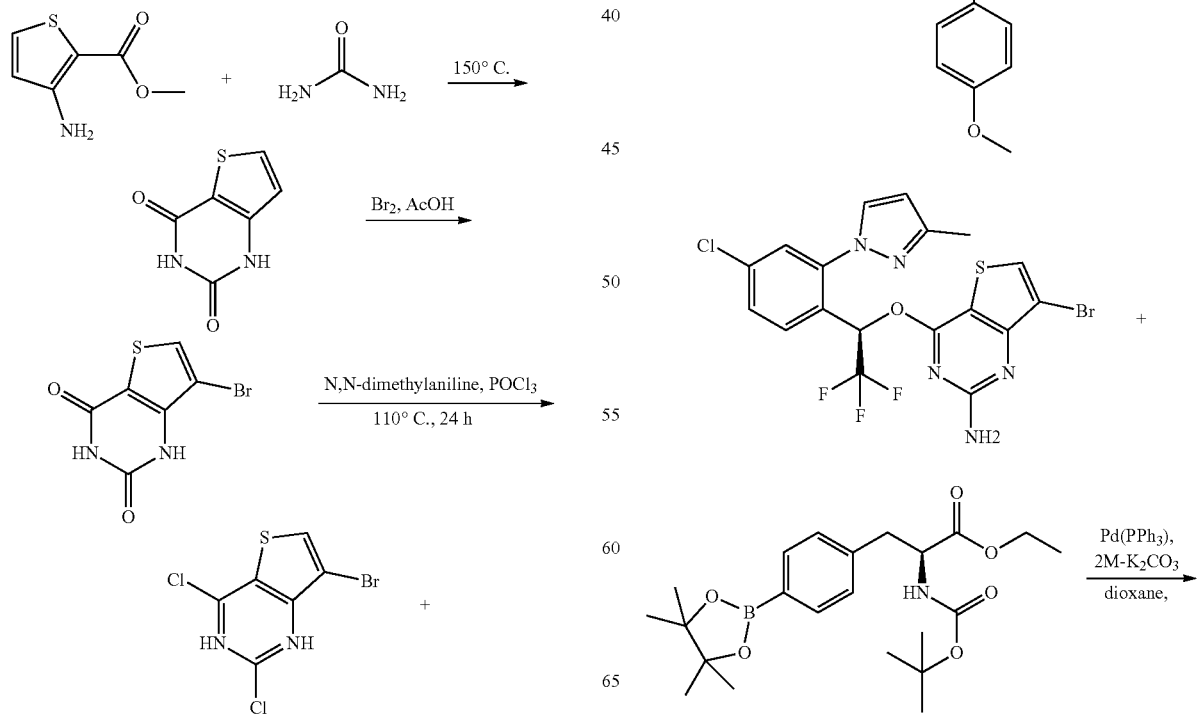

-continued

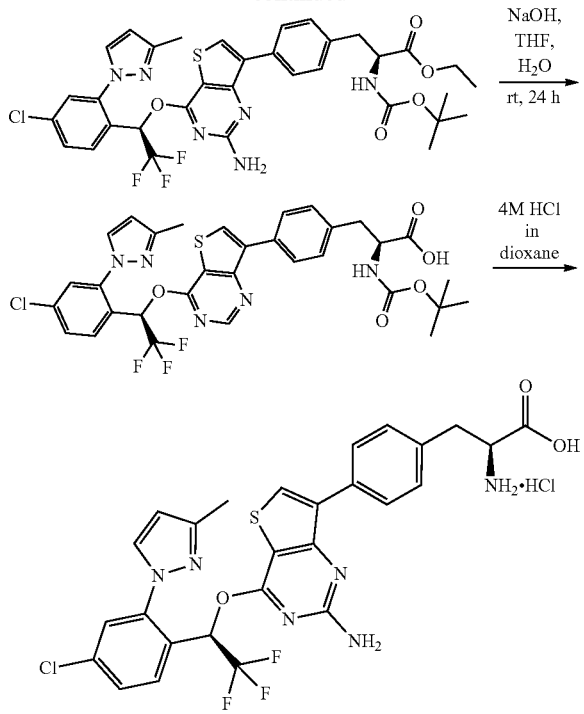

Step 1:
Methyl 3-amino-2-thiophene carboxylate (2 g, 12.73 mmol) and urea (4.6 g, 76.34 mmol) were heated at 190° C. for 4 hours in a sealed tube. The heated reaction mixture was poured into sodium hydroxide solution and the insoluble materials were removed by filtration. The mixture was acidified with hydrochloric acid (HCl, 2N) and the resulting cream-colored precipitate was combined by filtration and dried with air. As a result, 1H-thieno[3,2-d]pyrimidine-2,4-dione (1.1 g, 51%) was obtained.

$^1$H NMR 400 MHz, d$_6$-DMSO) 6.90 (1H, d, J=5.2 Hz), 8.10 (1H, d, J=5.2 Hz), 11.60-11.10 (2H, br s).

Step 2:
Bromine (1.1 mL) was added dropwise to a solution of thieno[3,2-d]pyrimidine-2,4(1H,3H)-dione (1 g, 5.946 mmol) in acetic acid (20 mL). The reaction mixture was stirred at 90° C. for 12 hours, followed by cooling to room temperature, which was slowly added to ice water (200 mL). The white precipitate was collected and washed several times with water. The resulting solid (1.2 g, 81%) was air-dried and used in the next step without further purification.

$^1$H NMR (400 MHz, DMSO-d$_6$) δ 11.54 (s, 1H), 11.42 (s, 1H), 8.24 (s, 1H), MS m/z: 247.34, 249.32 [M+1].

Step 3:
Phosphoryl chloride (3.4 mL, 36.43 mmol) was added to 7-bromothieno [3,2-d] pyrimidine-2,4(1H, 3H)-dione (900 mg, 3.643 mmol), to which N,N-diethylaniline (1.85 mL, 14.57 mmol) was added slowly. The reaction mixture was stirred at 110° C. for 24 hours. The mixture was cooled to room temperature, which was slowly added to ice water (100 mL). The resulting solid was filtered, washed with water and dried. As a result, 7-bromo-2,4-dichlorothieno[3,2-d]pyrimidine (900 mg, 87%) was obtained.

$^1$H NMR (400 MHz, DMSO-d$_6$) δ 8.40 (s, 1H), MS m/z: 282.96, 284.96, 286.96 [M+1].

Step 4:
(R)-7-bromo-2-chloro-4-(1-(4-chloro-2-(3-methyl-1H-pyrazole-1-yl)phenyl)-2,2,2-trifluoroethoxy)thieno[3,2-d]pyrimidine (257 mg, 46%) was obtained by performing the method similar to step 1 of Example 8.

Step 5:
Triethylamine (94 mg, 0.929 mmol) and (4-methoxyphenyl) methanamine (95.59 mg, 0.697 mmol) were added to (R)-7-bromo-2-chloro-4-(1-(4-chloro-2-(3-methyl-1H-pyrazole-1-yl)phenyl)-2,2,2-trifluoroethoxy)thieno[3,2-d]pyrimidine (250 mg, 0.465 mmol) in ethanol (10 mL). The reaction mixture was reacted at 150° C. 1 hour in a single-mode microwave instrument (Biotage Initiator 2.5). The reaction mixture was evaporated and the concentrate was purified by silica gel column chromatography. As a result, (R)-7-bromo-4-(1-(4-chloro-2-(3-methyl-1H-pyrazole-1-yl)phenyl)-2,2,2-trifluoroethoxy)-N-(4-methoxybenzyl)thieno[3,2-d]pyrimidine-2-amine (290 mg, 98%) was obtained.

Step 6:
A mixture of (R)-7-bromo-4-(1-(4-chloro-2-(3-methyl-1H-pyrazole-1-yl)phenyl)-2,2,2-trifluoroethoxy)-N-(4-methoxybenzyl)thieno[3,2-d]pyrimidine-2-amine (290 mg, 0.454 mmol) and trifluoroacetic acid (TFA) (20 mL) was stirred at 120° C. for 24 hours in a sealed tube. The reaction mixture was evaporated and the concentrate was purified by silica gel column chromatography. As a result, ((R)-7-bromo-4-(1-(4-chloro-2-(3-methyl-1H-pyrazole-1-yl)phenyl)-2,2,2-trifluoroethoxy)thieno[3,2-d]pyrimidine-2-amine (230 mg, 97%) was obtained.

Step 7:
Ethyl (S)-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)-2-((tert-butoxycarbonyl)amino) propanoate (280 mg, 86%) was obtained by performing the method similar to step 2 of Example 8.

Step 8:
(S)-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)-2-((tert-butoxycarbonyl)amino) propionic acid was obtained by performing the method similar to step 3 of Example 8.

Step 9:
A solution of 4.0 M HCl in 1,4 dioxane (10 mL) was added to (S)-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)-2-((tert-butoxycarbonyl)amino) propionic acid in ethyl acetate (10 mL). The mixture was then stirred for 12 hours. The mixture was concentrated, to which ethyl acetate/hexane (1:5) was added. The concentrate was collected by filtration. As a result, (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propanoic acid hydrochloride (195 mg, 80%, two-step yield) was obtained as a cream-colored solid.

The compounds of Examples 105 and 106 were prepared by performing the method similar to the preparation method of Example 91.

The compounds of Examples 37-39 were prepared by performing the method similar to the preparation method of reaction formula 3.

The compounds of Examples 40-43 were prepared by performing the method similar to the preparation method of reaction formula 4.

The structures and names of the compounds of Examples 1 to 120 prepared by performing the methods similar to the preparation methods of Examples 8, 12, 28, 29, 31, 36, 79, 80 and 91 are shown in tables 1 and 2 below.

Table 1 shows the chemical structures and names of the compounds of Examples 1 to 43.

TABLE 1

| Example | Chemical Formula | Compound Name |
|---|---|---|
| 1 | | (S)-2-amino-3-(4-((7-((5-fluoro-[1,1'-biphenyl]-2-yl)methyl)-7H-pyrrolo[2,3-d]pyrimidine-4-yl)oxy)phenyl)propionic acid hydrochloride |
| 2 | | (S)-2-amino-3-(4-((7-(3-bromobenzyl)-7H-pyrrolo[2,3-d]pyrimidine-4-yl)oxy)phenyl)propionic acid hydrochloride |
| 3 | | (S)-2-amino-3-(4-((2-amino-7-(2-bromo-4-fluorobenzyl)-7H-pyrrolo[2,3-d]pyrimidine-4-yl)oxy)phenyl)propionic acid hydrochloride |
| 4 | | (S)-2-amino-3-(4-((2-amino-7-((5-fluoro-3'-methoxy-[1,1'-biphenyl]-2-yl)methyl)-7H-pyrrolo[2,3-d]pyrimidine-4-yl)oxy)phenyl)propionic acid hydrochloride |
| 5 | | (S)-2-amino-3-(4-((2-amino-7-((5-fluoro-4'-(hydroxymethyl)-[1,1'-biphenyl]-2-yl)methyl)-7H-pyrrolo[2,3-d]pyrimidine-4-yl)oxy)phenyl)propionic acid hydrochloride |

TABLE 1-continued

| Example | Chemical Formula | Compound Name |
|---|---|---|
| 6 | | (S)-2-amino-3-(4-((2-amino-7-(2-chloro-4-fluorobenzyl)-7H-pyrrolo[2,3-d]pyrimidine-4-yl)oxy)phenyl)propionic acid hydrochloride |
| 7 | | (S)-2-amino-3-(4-((7-((3'-methoxy-[1,1'-biphenyl]-3-yl)methyl)-7H-pyrrolo[2,3-d]pyrimidine-4-yl)oxy)phenyl)propionic acid hydrochloride |
| 8 | | (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride |
| 9 | | (2S)-2-amino-3-(4-(4-(2,2,2-trifluoro-1-(3'-fluoro-[1,1'-biphenyl]-4-yl)ethoxy)thieno[3,2-d]pyrimidine-7-yl)phenyl)propionic acid hydrochloride |

TABLE 1-continued

| Example | Chemical Formula | Compound Name |
|---|---|---|
| 10 | | (2S)-2-amino-3-(4-(4-(2,2,2-trifluoro-1-(3'-methoxy-[1,1'-biphenyl]-4-yl)ethoxy)thieno[3,2-d]pyrimidine-7-yl)phenyl)propionic acid hydrochloride |
| 11 | | (S)-2-amino-3-(4-(2-amino-7-(4-bromobenzyl)-7H-pyrrolo[2,3-d]pyrimidine-4-yl)phenyl)propionic acid hydrochloride |
| 12 | | (S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride |
| 13 | | (S)-2-amino-3-(4-(4-((5-chloro-3'-methoxy-[1,1'-biphenyl]-2-yl)methoxy)thieno[3,2-d]pyrimidine-7-yl)phenyl)propionic acid hydrochloride |

TABLE 1-continued

| Example | Chemical Formula | Compound Name |
|---|---|---|
| 14 | 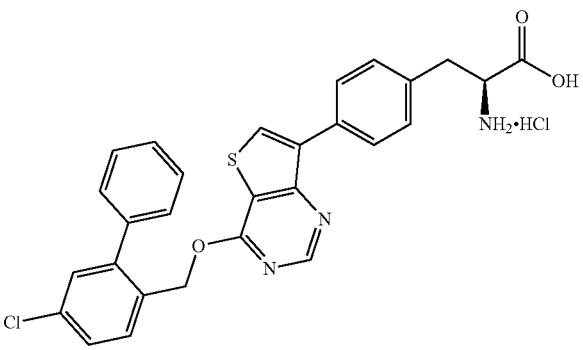 | (S)-2-amino-3-(4-(4-((5-chloro-[1,1'-biphenyl]-2-yl)methoxy)thieno[3,2-d]pyrimidine-7-yl)phenyl)propionic acid hydrochloride |
| 15 | 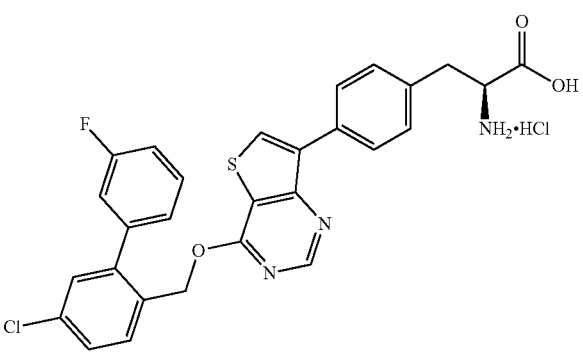 | (S)-2-amino-3-(4-(4-((5-chloro-3'-fluoro-[1,1'-biphenyl]-2-yl)methoxy)thieno[3,2-d]pyrimidine-7-yl)phenyl)propionic acid hydrochloride |
| 16 | 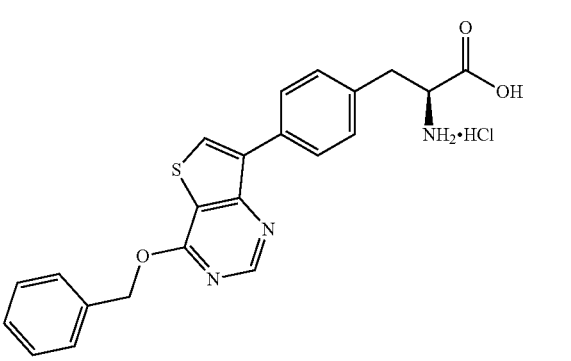 | (S)-2-amino-3-(4-(4-(benzyloxy)thieno[3,2-d]pyrimidine-7-yl)phenyl)propionic acid hydrochloride |
| 17 | 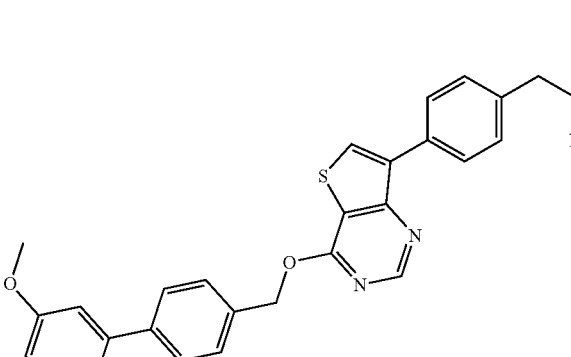 | (S)-2-amino-3-(4-(4-((3'-methoxy-[1,1'-biphenyl]-4-yl)methoxy)thieno[3,2-d]pyrimidine-7-yl)phenyl)propionic acid hydrochloride |

TABLE 1-continued

| Example | Chemical Formula | Compound Name |
|---|---|---|
| 18 | 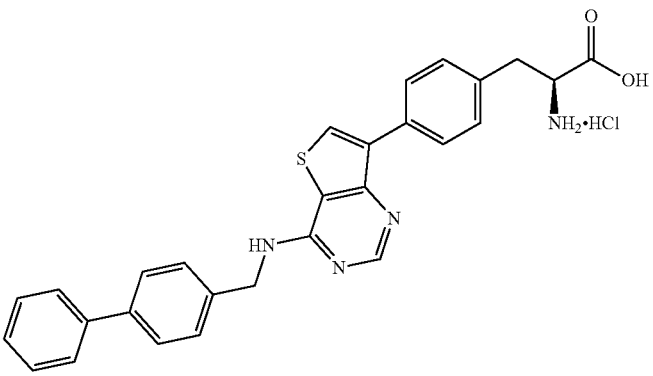 | (S)-3-(4-(4-(([1,1'-biphenyl]-4-ylmethyl)amino)thieno[3,2-d]pyrimidine-7-yl)phenyl)-2-aminopropionic acid hydrochloride |
| 19 | 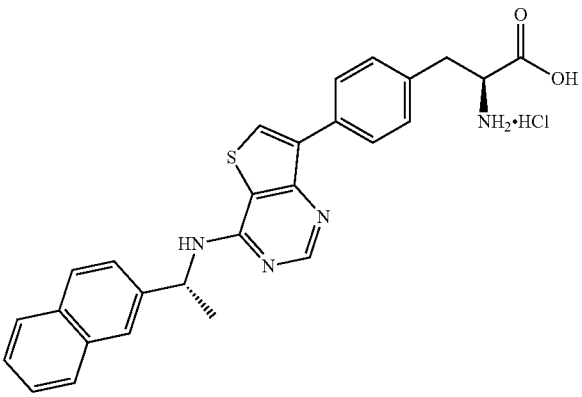 | (S)-2-amino-3-(4-(4-(((R)-1-(naphthalene-2-yl)ethyl)amino)thieno[3,2-d]pyrimidine-7-yl)phenyl)propionic acid hydrochloride |
| 20 | 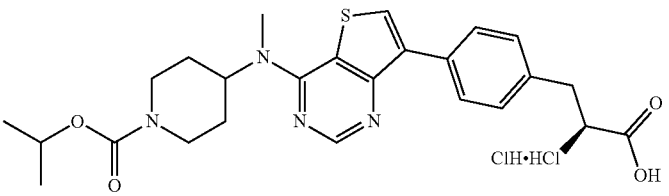 | (S)-2-amino-3-(4-(4-((1-(isopropoxycarbonyl)piperidine-4-yl)(methyl)amino)thieno[3,2-d]pyrimidine-7-yl)phenyl)propionic acid hydrochloride |
| 21 | 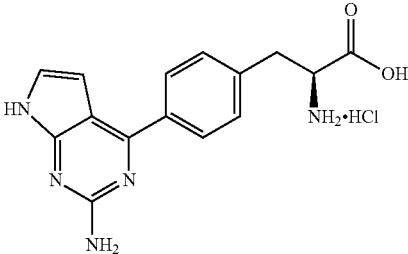 | (S)-2-amino-3-(4-(2-amino-7H-pyrrolo[2,3-d]pyrimidine-4-yl)phenyl)propionic acid |
| 22 | 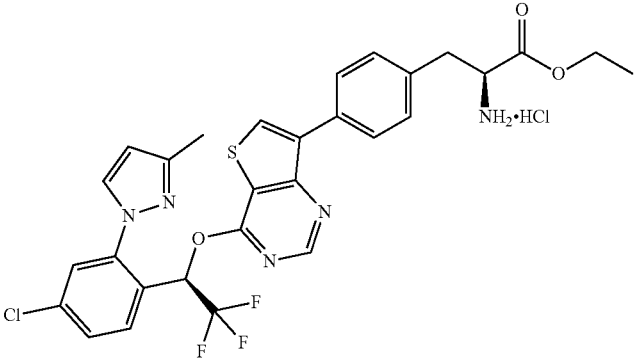 | ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hydrochloride |

TABLE 1-continued

| Example | Chemical Formula | Compound Name |
|---|---|---|
| 23 | | (S)-2-amino-3-(4-(7-((3'-methoxy-[1,1'-biphenyl]-4-yl)methyl)-7H-pyrrolo[2,3-d]pyrimidine-4-yl)phenyl)propionic acid hydrochloride |
| 24 | | (S)-2-amino-3-(4-(4-((R)-1-(5-chloro-3'-fluoro-[1,1'-biphenyl]-2-yl)-2,2,2-trifluoroethoxy)thieno[3,2-d]pyrimidine-7-yl)phenyl)propionic acid hydrochloride |
| 25 | | (2S)-2-amino-3-(4-(4-(1-(5-chloro-3'-methoxy-[1,1'-biphenyl]-2-yl)-2,2,2-trifluoroethoxy)thieno[3,2-d]pyrimidine-7-yl)phenyl)propionic acid hydrochloride |
| 26 | | (2S)-2-amino-3-(4-(4-(1-(5-chloro-[1,1'-biphenyl]-2-yl)-2,2,2-trifluoroethoxy)thieno[3,2-d]pyrimidine-7-yl)phenyl)propionic acid hydrochloride |

TABLE 1-continued

| Example | Chemical Formula | Compound Name |
|---|---|---|
| 27 | | (S)-2-amino-3-(4-(4-((R)-2,2,2-trifluoro-1-(3'-methoxy-[1,1'-biphenyl]-4-yl)ethoxy)thieno[3,2-d]pyrimidine-7-yl)phenyl)propionic acid hydrochloride |
| 28 | | ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate |
| 29 | | ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate |
| 30 | | (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid hydrochloride |

TABLE 1-continued

| Example | Chemical Formula | Compound Name |
|---|---|---|
| 31 | 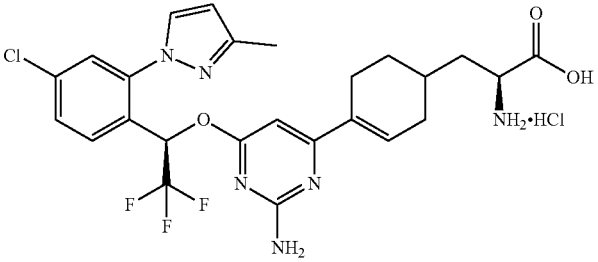 | (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride |
| 32 | 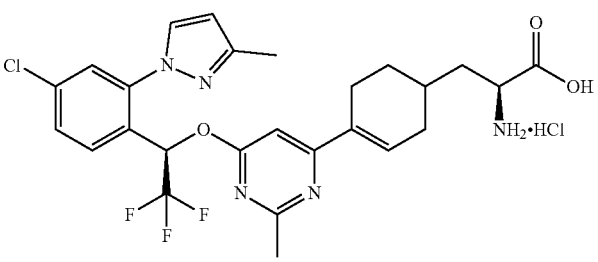 | (2S)-2-amino-3-(4-(6-((R)-1-(4-chloro-2-(3-methyl-1H-pyrazole-1-yl)phenyl)-2,2,2-trifluoroethoxy)-2-methylpyrimidine-4-yl)cyclohex-3-ene-1-yl)propionic acid hydrochloride |
| 33 | 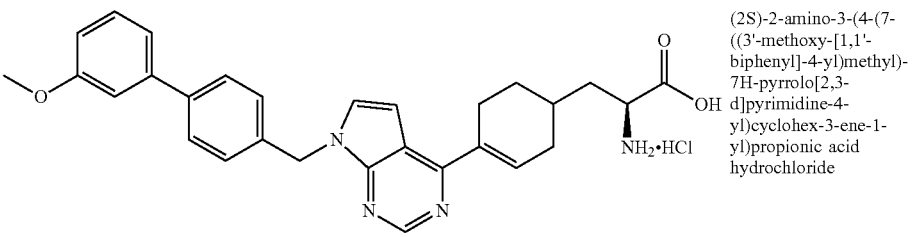 | (2S)-2-amino-3-(4-(7-((3'-methoxy-[1,1'-biphenyl]-4-yl)methyl)-7H-pyrrolo[2,3-d]pyrimidine-4-yl)cyclohex-3-ene-1-yl)propionic acid hydrochloride |
| 34 | 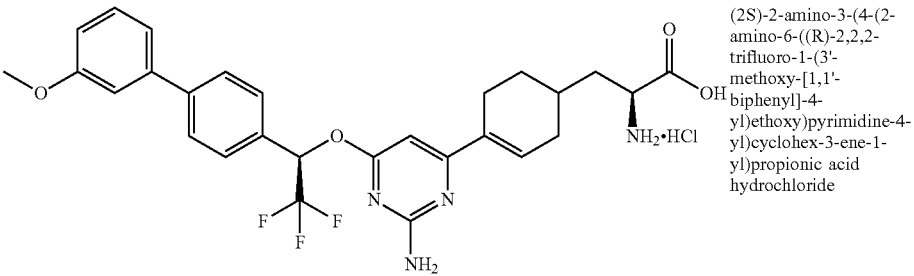 | (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid hydrochloride |
| 35 | 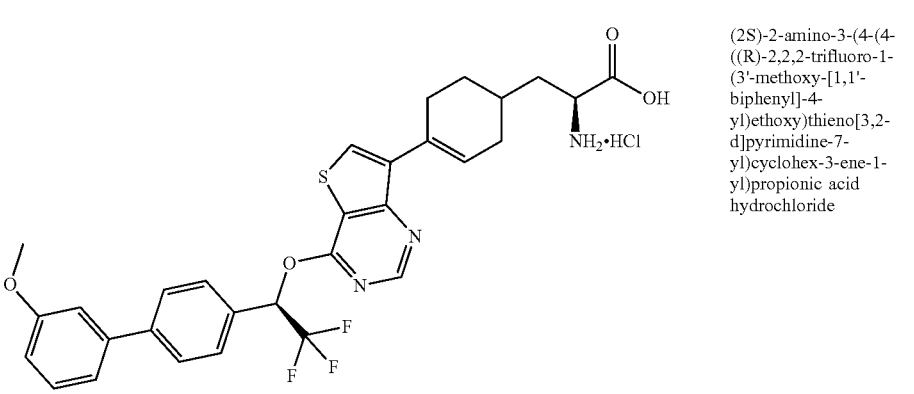 | (2S)-2-amino-3-(4-(4-((R)-2,2,2-trifluoro-1-(3'-methoxy-[1,1'-biphenyl]-4-yl)ethoxy)thieno[3,2-d]pyrimidine-7-yl)cyclohex-3-ene-1-yl)propionic acid hydrochloride |

TABLE 1-continued

| Example | Chemical Formula | Compound Name |
|---|---|---|
| 36 | | ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate |
| 37 | | (S)-2-amino-3-(4-(5-(4-methoxyphenyl)-1,2,4-oxadiazole-3-yl)phenyl)propionic acid hydrochloride |
| 38 | | (S)-2-amino-3-(4-(5-phenyl-1,2,4-oxadiazole-3-yl)phenyl)propionic acid hydrochloride |
| 39 | | (S)-2-amino-3-(4-(5-(4-fluorophenyl)-1,2,4-oxadiazole-3-yl)phenyl)propionic acid hydrochloride |
| 40 | | (S)-2-amino-3-(4-(5-(4-bromophenyl)-1,3,4-oxadiazole-2-yl)phenyl)propionic acid hydrochloride |
| 41 | | (S)-2-amino-3-(4-(5-phenyl-1,3,4-oxadiazole-2-yl)phenyl)propionic acid hydrochloride |
| 42 | | (S)-3-(4-(5-([1,1'-biphenyl]-4-yl)-1,3,4-oxadiazole-2-yl)phenyl)-2-aminopropionic acid hydrochloride |

TABLE 1-continued

| Example | Chemical Formula | Compound Name |
|---------|------------------|---------------|
| 43 | | (S)-2-amino-3-(4-(5-(4'-hydroxy-[1,1'-biphenyl]-4-yl)-1,3,4-oxadiazole-2-yl)phenyl)propionic acid hydrochloride |

Table 2 shows the chemical structures and names of the compounds of Examples 44 to 120.

TABLE 2

| Example | Chemical Formula | Compound Name |
|---------|------------------|---------------|
| 44 | | (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionic acid |
| 45 | | (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid |
| 46 | | (2S)-2-amino-3-(4-(4-(1-(5-chloro-4'-fluoro-[1,1'-biphenyl]-2-yl)-2,2,2-trifluoroethoxy)thieno[3,2-d]pyrimidine-7-yl)phenyl)propionic acid hydrochloride |

TABLE 2-continued

| Example | Chemical Formula | Compound Name |
|---|---|---|
| 47 | | (2S)-2-amino-3-(4-(2-amino-6-(1-(5-chloro-4'-fluoro-[1,1'-biphenyl]-2-yl)-2,2,2-trifluoroethoxy)pyrimidine-4-yl)cyclohex-3-ene-1-yl)propionic acid hydrochloride |
| 48 | | (2S)-2-amino-3-(4-(2-amino-6-(1-(5-chloro-[1,1'-biphenyl]-2-yl)-2,2,2-trifluoroethoxy)pyrimidine-4-yl)cyclohex-3-ene-1-yl)propionic acid hydrochloride |
| 49 | | (2S)-2-amino-3-(4-(1-((3'-methoxy-[1,1'-biphenyl]-4-yl)methyl)-1H-pyrazole-4-yl)cyclohex-3-ene-1-yl)propionic acid hydrochloride |
| 50 | | (2S)-2-amino-3-(4-(4-(1-(5-chloro-4'-fluoro-[1,1'-biphenyl]-2-yl)-2,2,2-trifluoroethoxy)thieno[3,2-d]pyrimidine-7-yl)cyclohex-3-ene-1-yl)propionic acid hydrochloride |
| 51 | | (2S)-2-amino-3-(4-(4-(1-(5-chloro-[1,1'-biphenyl]-2-yl)-2,2,2-trifluoroethoxy)thieno[3,2-d]pyrimidine-7-yl)cyclohex-3-ene-1-yl)propionic acid hydrochloride |

TABLE 2-continued

| Example | Chemical Formula | Compound Name |
|---|---|---|
| 52 | 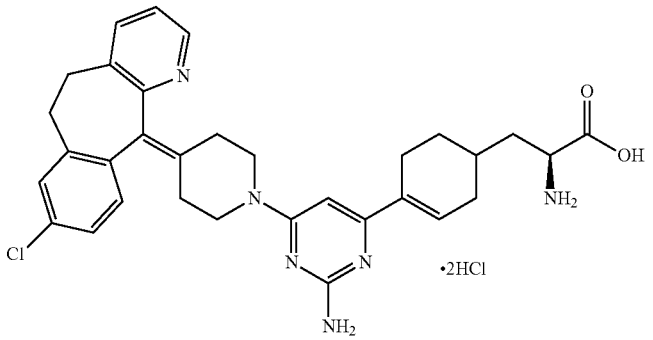 [SMILES: Nc1nc(C2=CCC(C[C@H](N)C(=O)O)CC2)cc(N2CCC(=C3c4ccc(Cl)cc4CCc4cccnc43)CC2)n1] | (2S)-2-amino-3-(4-(2-amino-6-(4-(8-chloro-5,6-dihydro-11H-benzo[5,6]cyclohepta[1,2-b]pyridine-11-ylidene)piperidine-1-yl)pyrimidine-4-yl)cyclohex-3-ene-1-yl)propionic acid dihydrochloride |
| 53 | 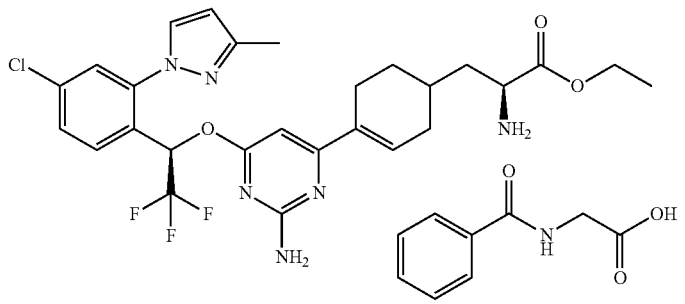 | ethyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate |
| 54 | 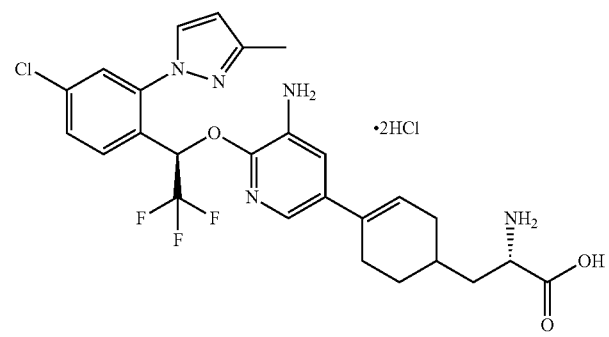 [SMILES: Cc1ccn(-c2cc(Cl)ccc2[C@@H](Oc2ncc(C3=CCC(C[C@H](N)C(=O)O)CC3)cc2N)C(F)(F)F)n1] | (2S)-2-amino-3-(4-(5-amino-6-((R)-1-(4-chloro-2-(3-methyl-1H-pyrazole-1-yl)phenyl)-2,2,2-trifluoroethoxy)pyridine-3-yl)cyclohex-3-ene-1-yl)propionic acid dihydrochloride |
| 55 | 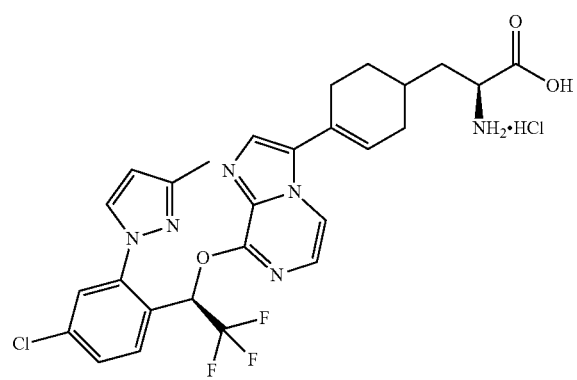 | (2S)-2-amino-3-(4-(8-((R)-1-(4-chloro-2-(3-methyl-1H-pyrazole-1-yl)phenyl)-2,2,2-trifluoroethoxy)imidazo[1,2-a]pyrazine-3-yl)cyclohex-3-ene-1-yl)propionic acid hydrochloride |

TABLE 2-continued

| Example | Chemical Formula | Compound Name |
| --- | --- | --- |
| 56 | 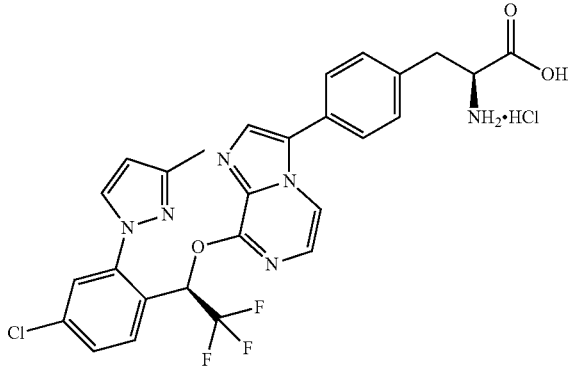 | (S)-2-amino-3-(4-(8-((R)-1-(4-chloro-2-(3-methyl-1H-pyrazole-1-yl)phenyl)-2,2,2-trifluoroethoxy)imidazo[1,2-a]pyrazine-3-yl)phenyl)propionic acid hydrochloride |
| 57 | 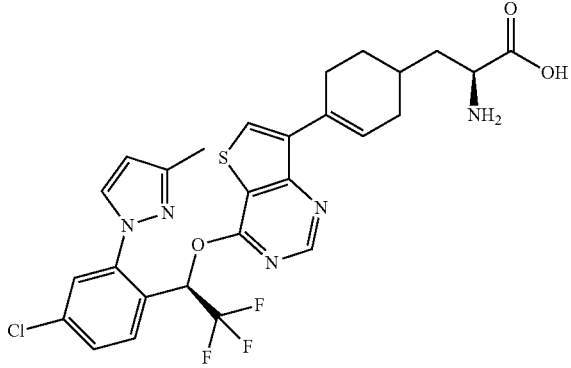 [SMILES: Cc1ccn(-c2cc(Cl)ccc2[C@@H](Oc2ncnc3c(C4=CCC(C[C@H](N)C(=O)O)CC4)csc23)C(F)(F)F)n1] | (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid |
| 58 | 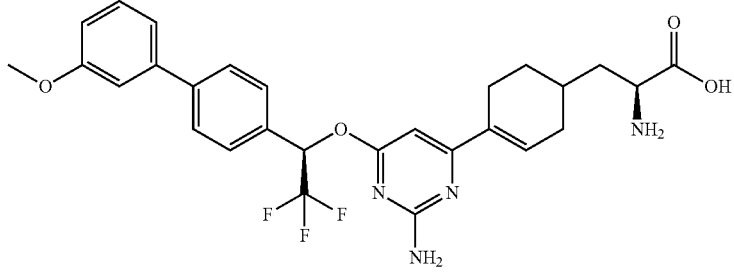 [SMILES: COc1cccc(-c2ccc([C@@H](Oc3cc(C4=CCC(C[C@H](N)C(=O)O)CC4)nc(N)n3)C(F)(F)F)cc2)c1] | (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid |
| 59 | 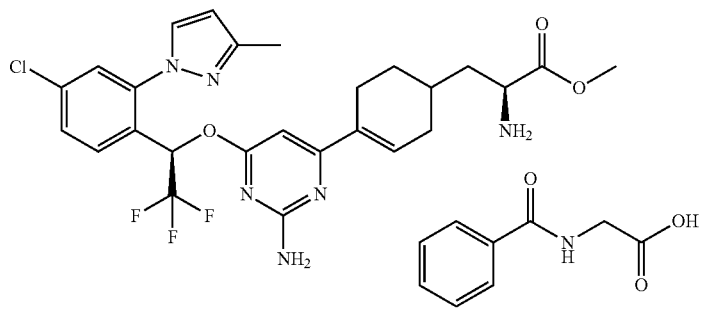 | methyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate |

TABLE 2-continued

| Example | Chemical Formula | Compound Name |
| --- | --- | --- |
| 60 | 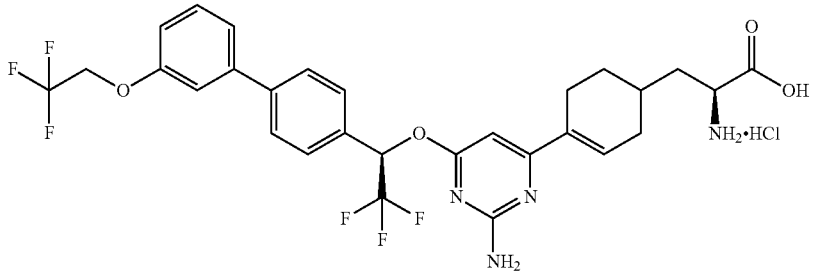 | (2S)-2-amino-3-(4-(2-amino-6-((R)-2,2,2-trifluoro-1-(3'-(2,2,2-trifluoroethoxy)-[1,1'-biphenyl]-4-yl)ethoxy)pyrimidine-4-yl)cyclohex-3-ene-1-yl)propionic acid hydrochloride |
| 61 | 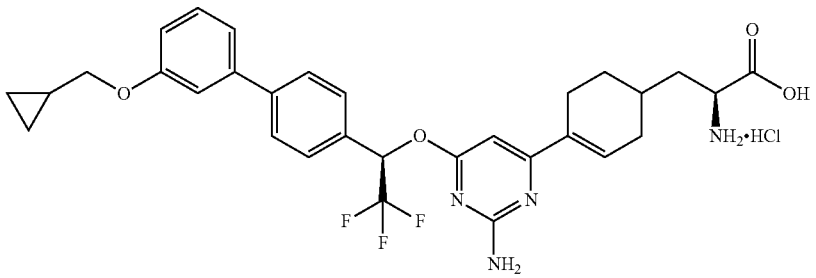 | (2S)-2-amino-3-(4-(2-amino-6-((R)-1-(3'-(cyclopropylmethoxy)-[1,1'-biphenyl]-4-yl)-2,2,2-trifluoroethoxy)pyrimidine-4-yl)cyclohex-3-ene-1-yl)propionic acid hydrochloride |
| 62 | 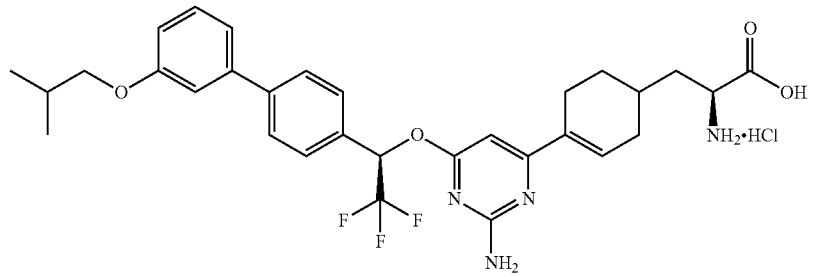 | (2S)-2-amino-3-(4-(2-amino-6-((R)-2,2,2-trifluoro-1-(3'-isobutoxy-[1,1'-biphenyl]-4-yl)ethoxy)pyrimidine-4-yl)cyclohex-3-ene-1-yl)propionic acid hydrochloride |
| 63 | 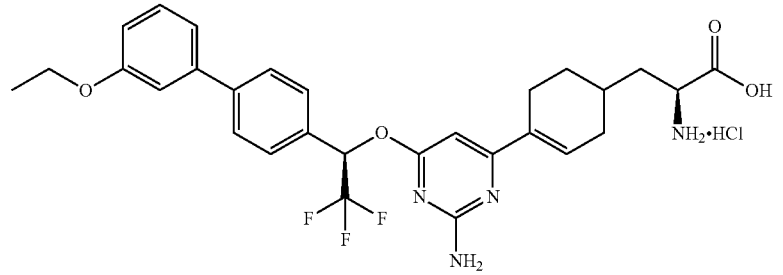 | (2S)-2-amino-3-(4-(2-amino-6-((R)-1-(3'-ethoxy-[1,1'-biphenyl]-4-yl)-2,2,2-trifluoroethoxy)pyrimidine-4-yl)cyclohex-3-ene-1-yl)propionic acid hydrochloride |
| 64 | 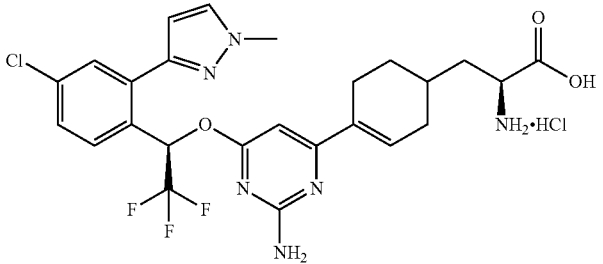 | (2S)-2-amino-3-(4-(2-amino-6-((R)-1-(4-chloro-2-(1-methyl-1H-pyrazole-3-yl)phenyl)-2,2,2-trifluoroethoxy)pyrimidine-4-yl)cyclohex-3-ene-1-yl)propionic acid hydrochloride |

TABLE 2-continued

| Example | Chemical Formula | Compound Name |
|---|---|---|
| 65 | | ethyl (2S)-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)-2-((tert-butoxycarbonyl)amino)propionate |
| 66 | | (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride |
| 67 | | (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid |
| 68 | | (2S)-2-amino-3-(4-(2-amino-6-((R)-1-(4-chloro-2-(1-methyl-1H-pyrazole-3-yl)phenyl)-2,2,2-trifluoroethoxy)pyrimidine-4-yl)cyclohex-3-ene-1-yl)propionic acid |
| 69 | | (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid hydrochloride |

TABLE 2-continued

| Example | Chemical Formula | Compound Name |
| --- | --- | --- |
| 70 | | (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid |
| 71 | | (2S)-2-amino-3-(4-(2-amino-6-((R)-1-(2-(benzofuran-3-yl)-4-chlorophenyl)-2,2,2-trifluoroethoxy)pyrimidine-4-yl)cyclohex-3-ene-1-yl)propionic acid hydrochloride |
| 72 | | (S)-2-amino-3-(4-(4-((R)-1-(2-(benzofuran-3-yl)-4-chlorophenyl)-2,2,2-trifluoroethoxy)thieno[3,2-d]pyrimidine-7-yl)phenyl)propionic acid hydrochloride |
| 73 | | (S)-2-amino-3-(4-(4-((R)-1-(4-chloro-2-(furan-3-yl)phenyl)-2,2,2-trifluoroethoxy)thieno[3,2-d]pyrimidine-7-yl)phenyl)propionic acid hydrochloride |

TABLE 2-continued

| Example | Chemical Formula | Compound Name |
|---|---|---|
| 74 | | (2S)-2-amino-3-(4-(2-amino-6-((R)-1-(4-chloro-2-(furan-3-yl)phenyl)-2,2,2-trifluoroethoxy)pyrimidine-4-yl)cyclohex-3-ene-1-yl)propionic acid hydrochloride |
| 75 | | (2S)-2-amino-3-(4-(2-amino-6-((R)-1-(5-chloro-4',4'difluoro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride |
| 76 | | (2S)-2-amino-3-(4-(2-amino-6-((R)-1-(5-chloro-4'-methoxy-[1,1'-biphenyl]-2-yl)-2,2,2-trifluoroethoxy)pyrimidine-4-yl)cyclohex-3-ene-1-yl)propionic acid hydrochloride |
| 77 | | (2S)-2-amino-3-(4-(2-amino-6-((R)-1-(4-chloro-2-(2,2,6,6-tetramethyl-3,6-dihydro-2H-pyran-4-yl)phenyl)-2,2,2-trifluoroethoxy)pyrimidine-4-yl)cyclohex-3-ene-1-yl)propionic acid hydrochloride |
| 78 | | (S)-2-amino-3-(4-(4-((R)-1-(4-chloro-2-(2,2,6,6-tetramethyl-3,6-dihydro-2H-pyran-4-yl)phenyl)-2,2,2-trifluoroethoxy)thieno[3,2-d]pyrimidine-7-yl)phenyl)propionic acid hydrochloride |

TABLE 2-continued

| Example | Chemical Formula | Compound Name |
|---|---|---|
| 79 | | 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride |
| 80 | | 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid |
| 81 | | (S)-2-amino-3-(4-(4-((R)-1-(4-chloro-2-(3,6-dihydro-2H-pyran-4-yl)phenyl)-2,2,2-trifluoroethoxy)thieno[3,2-d]pyrimidine-7-yl)phenyl)propionic acid hydrochloride |
| 82 | | (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid hydrochloride |

TABLE 2-continued

| Example | Chemical Formula | Compound Name |
| --- | --- | --- |
| 83 | | 8-(2-amino-6-((R)-1-(4-chloro-2-(3,6-dihydro-2H-pyran-4-yl)phenyl)-2,2,2-trifluoroethoxy)pyrimidine-4-yl)-2-azaspiro[4.5]dec-7-ene-3-carboxylic acid hydrochloride |
| 84 | | 8-(4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride |
| 85 | | (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid |
| 86 | | ethyl (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionate hippurate |

TABLE 2-continued

| Example | Chemical Formula | Compound Name |
|---|---|---|
| 87 | | 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid hydrochloride |
| 88 | | 8-(2-amino-6-((R)-2,2,2-trifluoro-1-(3'-fluoro-[1,1'-biphenyl]4-yl)ethoxy)pyrimidine-4-yl)-2-azaspiro[4.5]dec-7-ene-3-carboxylic acid hydrochloride |
| 89 | | 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid |
| 90 | | (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid hydrochloride |

TABLE 2-continued

| Example | Chemical Formula | Compound Name |
|---|---|---|
| 91 | | (S)-2-amino-3-(4-(2-amino-4-((R)-1-(4-chloro-2-(3-methyl-1H-pyrazol-1-yl)phenyl)-2,2,2-trifluoroethoxy)thieno[3,2-d]pyrimidine-7-yl)phenyl)propionic acid hydrochloride |
| 92 | | (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid |
| 93 | | 8-(4-((R)-1-(4-chloro-2-(5,6-dihydro-2H-pyran-3-yl)phenyl)-2,2,2-trifluoroethoxy)thieno[3,2-d]pyrimidine-7-yl)-2-azaspiro[4.5]dec-7-ene-3-carboxylic acid hydrochloride |
| 94 | | 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride |

TABLE 2-continued

| Example | Chemical Formula | Compound Name |
|---|---|---|
| 95 | | 8-(2-amino-6-((R)-2,2,2-trifluoro-1-(3'-fluoro-[1,1'-biphenyl]-4-yl)ethoxy)pyrimidine-4-yl)-2-azaspiro[4.5]dec-7-ene-3-carboxylic acid |
| 96 | | neopentyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate |
| 97 | | (2S)-2-amino-3-(4-(2-amino-6-((R)-1-(4-chloro-2-(3,4-dihydro-2H-pyran-5-yl)phenyl)-2,2,2-trifluoroethoxy)pyrimidine-4-yl)cyclohex-3-ene-1-yl)propionic acid hydrochloride |
| 98 | | (2S)-2-amino-3-(4-(2-amino-6-((R)-1-(5-chloro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride |
| 99 | | (S)-2-amino-3-((R)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride |

TABLE 2-continued

| Example | Chemical Formula | Compound Name |
| --- | --- | --- |
| 100 |  | (S)-2-amino-3-((S)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride |
| 101 |  | (S)-2-amino-3-((R)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride |
| 102 |  | (S)-2-amino-3-((S)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride |
| 103 |  | (S)-2-amino-3-(4-(4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride |
| 104 |  | (S)-2-amino-3-(4-(4-((R)-1-(5-chloro-2',3',4',5'-tetrahydro-[1,1'-biphenyl]-2-yl)-2,2,2-trifluoroethoxy)thieno[3,2-d]pyrimidine-7-yl)phenyl)propionic acid hydrochloride |

TABLE 2-continued

| Example | Chemical Formula | Compound Name |
| --- | --- | --- |
| 105 | | (S)-2-amino-3-(4-(2-amino-4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid hydrochloride |
| 106 | | (S)-2-amino-3-(4-(2-amino-4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride |
| 107 | | 8-(2-amino-4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride |
| 108 | | 8-(2-amino-6-((R)-1-(4-chloro-2-(3,4-dihydro-2H-pyran-5-yl)phenyl)-2,2,2-trifluoroethoxy)pyrimidine-4-yl)-2-azaspiro[4.5]dec-7-ene-3-carboxylic acid hydrochloride |

TABLE 2-continued

| Example | Chemical Formula | Compound Name |
|---|---|---|
| 109 | | 8-(2-amino-6-((R)-1-(5-chloro-2',3',4',5'-tetrahydro-[1,1'-biphenyl]-2-yl)-2,2,2-trifluoroethoxy)pyrimidine-4-yl)-2-azaspiro[4.5]dec-7-ene-3-carboxylic acid hydrochloride |
| 110 | | (3S,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride |
| 111 | | (3S,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride |
| 112 | | (3R,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride |

TABLE 2-continued

| Example | Chemical Formula | Compound Name |
|---|---|---|
| 113 | | (3R,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride |
| 114 | | (3S,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride |
| 115 | | (3S,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride |
| 116 | | (3R,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride |

TABLE 2-continued

| Example | Chemical Formula | Compound Name |
| --- | --- | --- |
| 117 | | (3R,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride |
| 118 | | ethyl 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylate hippurate |
| 119 | | ethyl 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylate hippurate |
| 120 | | ethyl (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate |

<Experimental Example 1> Analysis of Compounds of Examples According to the Present Invention The compounds of Examples 1 to 120 according to the present invention were analyzed by nuclear magnetic resonance spectroscopy (NMR) or liquid chromatography-mass spectrometry (LC-MS). The NMR or LCMS values of the compounds of Examples 1 to 95 are shown in tables 3 and 4 below.

Table 3 shows the NMR or LCMS values of the compounds of Examples 1 to 43.

TABLE 3

| Example | LCMS or NMR |
|---|---|
| 1 | LCMS [M + H]483.18 |
| 2 | LCMS [M + H]467.06 |
| 3 | LCMS [M + H]500.07 |
| 4 | LCMS [M + H]528.2 |
| 5 | LCMS [M + H]528.2 |
| 6 | LCMS [M + H]556.12 |
| 7 | LCMS [M + H]495.2 |
| 8 | $^1$H NMR (400 MHz, DMSO-d$_6$): δ 13.83 (s, 1H), 8.70 (d, J = 1.22 Hz, 1H), 8.66 (d, J = 1.53 Hz, 1H), 8.37 (bs, 3H), 8.24 (s, 1H), 7.98 (d, J = 7.32 Hz, 2H), 7.88-7.77 (m, 1H), 7.72-7.68 (m, 1H), 7.56 (dt, J = 8.54, 1.22 Hz, 1H), 7.37 (d, J = 7.63 Hz, 2H), 6.43-6.39 (m, 1H), 4.24-4.15 (m, 1H), 3.14 (d, J = 6.10 Hz, 2H), 2.27 (s, 3H). |
| 9 | $^1$H NMR (400 MHz, DMSO-d$_6$): δ 8.90-8.80 (m, 1H), 8.75-8.66 (m, 1H), 8.44 (bs, 3H), 8.09-7.95 (m, 2H), 7.85-7.71 (m, 4H), 7.57-7.33 (m, 5H), 7.31-7.13 (m, 2H), 4.25-4.12 (m, 1H), 3.23-3.09 (m, 2H). |
| 10 | $^1$H NMR (400 MHz, DMSO-d$_6$): δ 8.90-8.86 (m, 1H), 8.76-8.72 (m, 1H), 8.47 (bs, 3H), 8.32 (s, 1H), 8.07-8.01 (m, 1H), 7.76-7.70 (m, 3H), 7.42-7.30 (m, 3H), 7.26-7.13 (m, 1H), 7.06-6.98 (m, 1H), 6.96-6.88 (m, 1H), 6.72-6.64 (m, 1H), 4.24-4.12 (m, 1H), 3.76 (s, 3H), 3.20-3.11 (m, 2H). |
| 11 | $^1$H NMR (400 MHz, DMSO-d$_6$): δ 8.54 (bs, 3H), 8.06 (d, J = 8.24 Hz, 2H), 7.67-7.51 (m, 7H), 7.25 (d, J = 8.24 Hz, 2H), 6.80 (d, J = 3.66 Hz, 1H), 5.31 (s, 2H), 4.34-4.24 (m, 1H), 3.26 (d, J = 6.18 Hz, 2H). |
| 12 | $^1$H NMR (400 MHz, DMSO-d$_6$): δ 8.52 (bs, 3H), 8.06 (d, J = 8.24 Hz, 2H), 7.70-7.63 (m, 3H), 7.59 (d, J = 8.24 Hz, 2H), 7.42-7.33 (m, 3H), 7.19 (d, J = 7.33 Hz, 1H), 7.16-7.13 (m, 1H), 6.93 (dd, J = 8.24, 2.29 Hz, 1H), 6.81 (d, J = 3.66 Hz, 1H), 5.38 (s, 2H), 4.34-4.23 (m, 1H), 3.80 (s, 3H), 3.27 (d, J = 6.41 Hz, 2H). |
| 13 | $^1$H NMR (400 MHz, DMSO-d$_6$): δ 8.32 (bs, 3H), 8.25 (s, 1H), 8.05 (d, J = 7.93 Hz, 1H), 7.93 (d, J = 7.93 Hz, 1H), 7.44-7.34 (m, 6H), 7.05 (d, J = 8.24 Hz, 1H), 7.01-6.95 (m, 2H), 6.71 (d, J = 8.24 Hz, 1H), 5.58 (s, 2H), 4.27-4.15 (m, 1H), 3.66 (s, 3H), 3.18 (d, J = 4.58 Hz, 2H). |
| 14 | $^1$H NMR (400 MHz, DMSO-d$_6$): δ 8.78 (s, 1H), 8.59 (s, 1H), 8.48 (bs, 3H), 8.39-8.35 (m, 1H), 8.24-8.19 (m, 1H), 8.00 (d, J = 8.24 Hz, 2H), 7.92-7.85 (m, 3H), 7.67 (d, J = 8.24 Hz, 1H), 7.54-7.28 (m, 4H), 5.52 (s, 2H), 4.23-4.11 (m, 1H), 3.14 (d, J = 5.95 Hz, 2H). |
| 15 | $^1$H NMR (400 MHz, DMSO-d$_6$): δ 8.47 (bs, 3H), 8.41 (s, 1H), 8.04 (d, J = 8.24 Hz, 2H), 7.93 (d, J = 8.24 Hz, 1H), 7.72 (d, J = 8.24 Hz, 2H), 7.56 (dd, J = 8.24, 2.29 Hz, 1H), 7.46-7.25 (m, 6H), 7.19 (dt, J = 8.24, 2.75 Hz, 1H), 5.59 (s, 2H), 4.27-4.16 (m, 1H), 3.22-3.15 (m, 2H). |
| 16 | $^1$H NMR (400 MHz, DMSO-d$_6$): δ 12.73 (s, 1H), 8.89 (d, J = 4.27 Hz, 1H), 8.57 (d, J = 3.36 Hz, 1H), 8.44 (bs, 3H), 8.06-8.00 (m, 2H), 7.53-7.47 (m, 2H), 7.43-7.31 (m, 5H), 5.65 (s, 2H), 4.24-4.12 (m, 1H), 3.16 (d, J = 6.10 Hz, 2H),. |
| 17 | $^1$H NMR (400 MHz, DMSO-d$_6$): δ 8.48 (bs, 3H), 8.41 (s, 1H), 8.25 (s, 1H), 7.93 (d, J = 8.24 Hz, 2H), 7.67-7.59 (m, 1H), 7.47-7.33 (m, 5H), 7.04 (d, J = 8.24 Hz, 2H), 6.71 (d, J = 8.24 Hz, 2H), 5.55 (s, 2H), 4.27-4.16 (m, 1H), 3.56 (s, 3H), 3.18 (d, J = 6.41 Hz, 2H). |
| 18 | $^1$H NMR (400 MHz, DMSO-d$_6$): δ 8.66 (d, J = 3.21 Hz, 1H), 8.52 (bs, 3H), 8.44 (d, J = 4.12 Hz, 1H), 7.82 (d, J = 7.33 Hz, 2H), 7.68-7.60 (m, 4H), 7.52-7.40 (m, 6H), 7.39-7.32 (m, 1H), 4.88 (s, 2H), 4.27-4.16 (m, 1H), 3.21 (d, J = 3.21 Hz, 2H). |
| 19 | $^1$H NMR (400 MHz, DMSO-d$_6$): δ 8.60 (s, 1H), 8.50 (bs, 3H), 8.44 (s, 1H), 7.96-7.85 (m, 4H), 7.80 (d, J = 7.33 Hz, 2H), 7.65 (d, J = 8.24 Hz, 1H), 7.53-7.44 (m, 3H), 7.41 (d, J = 7.79 Hz, 2H), 5.84-5.74 (m, 1H), 4.25-4.15 (m, 1H), 3.56 (s, 3H), 3.20 (d, J = 6.41 Hz, 2H). |
| 20 | $^1$H NMR (400 MHz, DMSO-d$_6$): δ 8.69-8.47 (m, 5H), 7.88-7.73 (m, 2H), 7.43 (d, J = 7.93 Hz, 2H), 5.07-4.94 (m, 1H), 4.84-4.73 (m, 1H), 4.26-4.08 (m, 3H), 3.40 (s, 3H), 3.27-3.18 (m, 2H), 3.03-2.81 (m, 2H), 1.88-1.68 (m, 4H), 1.20 (d, J = 3.36 Hz, 6H). |
| 21 | $^1$H NMR (400 MHz, DMSO-d$_6$): δ 12.39 (s, 1H), 8.55 (bs, 3H), 8.06 (d, J = 8.01 Hz, 2H), 7.95 (s, 2H), 7.60 (d, J = 8.01 Hz, 2H), 7.53 (s, 1H), 6.76-6.69 (m, 1H), 4.34-4.23 (m, 1H), 3.27 (d, J = 6.18 Hz, 2H). |
| 22 | $^1$H NMR (400 MHz, DMSO-d$_6$): δ 8.72 (d, J = 13.12 Hz, 2H), 8.57 (bs, 3H), 8.27 (d, J = 2.44 Hz, 1H), 8.03 (d, J = 8.24 Hz, 2H), 7.92-7.81 (m, 2H), 7.74 (d, J = 2.14 Hz, 1H), 7.60 (dd, J = 8.54, 2.14 Hz, 1H), 7.38 (d, J = 8.24 Hz, 2H), 6.44 (d, J = 2.44 Hz, 1H), 4.36-4.29 (m, 1H), 4.15 (q, J = 5.19 Hz, 2H), 3.26-3.10 (m, 2H), 2.31 (s, 3H), 1.13 (t, J = 7.02 Hz, 3H). |
| 23 | $^1$H NMR (400 MHz, DMSO-d$_6$): δ 9.03 (s, 1H), 8.54 (bs, 3H), 8.15 (d, J = 8.24 Hz, 2H), 8.03 (d, J = 2.75 Hz, 1H), 7.64 (d, J = 7.79 Hz, 2H), 7.56 (d, J = 6.87 Hz, 2H), 7.45-7.32 (m, 3H), 7.18 (d, J = 7.79 Hz, 1H), 7.15-7.10 (m, 1H), 7.09-7.03 (m, 1H), 6.92 (d, J = 8.24 Hz, 1H), 5.62 (s, 2H), 4.32-4.22 (m, 1H), 3.79 (s, 3H), 3.27 (d, J = 5.95 Hz, 2H). |
| 24 | $^1$H NMR (400 MHz, DMSO-d$_6$): δ 8.84 (d, J = 1.14 Hz, 1H), 8.71 (d, J = 0.92 Hz, 1H), 8.38 (bs, 3H), 8.02 (d, J = 8.01 Hz, 2H), 7.76 (d, J = 8.70 Hz, 1H), 7.67-7.58 (m, 2H), 7.52-7.33 (m, 6H), 6.92 (q, J = 6.41 Hz, 1H), 4.29-4.19 (m, 1H), 3.17 (d, J = 6.18 Hz, 2H). |
| 25 | $^1$H NMR (400 MHz, DMSO-d$_6$): δ 8.83 (d, J = 1.83 Hz, 1H), 8.74-8.70 (m, 1H), 8.42 (bs, 3H), 8.03 (d, J = 6.87 Hz, 2H), 7.75 (d, J = 8.70 Hz, 1H), 7.59 (d, J = 8.24 Hz, 1H), 7.51-7.38 (m, 4H), 7.21 (s, 1H), 7.12 (d, J = 6.87 Hz, 1H), 7.09-6.98 (m, 2H), 4.29-4.19 (m, 1H), 3.84 (s, 3H), 3.18 (d, J = 6.41 Hz, 2H). |
| 26 | $^1$H NMR (400 MHz, DMSO-d$_6$): δ 8.84 (d, J = 1.37 Hz, 1H), 8.71 (d, J = 0.94 Hz, 1H), 8.45 (bs, 3H), 8.02 (d, J = 8.01 Hz, 2H), 7.76 (d, J = 8.47 Hz, 1H), 7.65-7.49 (m, 6H), 7.46-7.37 (m, 3H), 6.93 (q, J = 6.41 Hz, 1H), 4.28-4.18 (m, 1H), 3.19 (d, J = 6.18 Hz, 2H). |
| 27 | $^1$H NMR (400 MHz, DMSO-d$_6$): δ 8.87 (d, J = 1.53 Hz, 1H), 8.72 (s, 1H), 8.43 (bs, 3H), 8.04 (d, J = 6.41 Hz, 2H), 7.81-7.72 (m, 4H), 7.46-7.34 (m, 3H), 7.29-7.16 (m, 3H), 6.95 (d, J = 8.24 Hz, 1H), 4.28-4.18 (m, 1H), 3.80 (s, 3H), 3.18 (d, J = 6.10 Hz, 2H), |
| 28 | $^1$H NMR (400 MHz, DMSO-d$_6$): δ 8.72 (d, J = 3.05 Hz, 1H), 8.64 (d, J = 3.05 Hz, 1H), 8.26 (d, J = 2.44 Hz, 1H), 7.94 (dd, J = 7.93, 2.44 Hz, 2H), 7.89-7.80 (m, 2H), 7.72 (t, J = 2.44 Hz, 1H), 7.59 (dt, J = 8.85, 2.44 Hz, 1H), 7.30 (dd, J = 8.24, 2.14 Hz, 2H), 6.44 (t, J = 2.44 Hz, 1H), 4.04 (q, J = 7.02 Hz, 2H), 3.62-3.55 (m, 1H), 2.96-2.78 (m, 2H), 2.30 (s, 3H), 1.12 (t, J = 7.02 Hz, 3H), |
| 29 | $^1$H NMR (400 MHz, DMSO-d$_6$): δ 8.77 (t, J = 5.49 Hz, 1H), 8.72 (s, 1H), 8.65 (s, 1H), 8.27 (d, J = 2.44 Hz, 1H), 7.95 (d, J = 7.93 Hz, 2H), 7.89-7.80 (m, 5H), 7.72 (d, J = 2.14 Hz, 1H), 7.59 (dd, J = 8.54, 2.14 Hz, 1H), 7.57-7.44 (m, 4H), 7.31 (d, J = 8.24 Hz, 2H), 6.44 (d, J = 2.14 Hz, 1H), 4.05 (q, J = 7.02 Hz, 2H), 3.90 (d, J = 5.80 Hz, 2H), 3.66-3.58 (m, 1H), 2.96-2.80 (m, 2H), 2.31 (s, 3H), 1.09 (t, J = 7.02 Hz, 3H). |

TABLE 3-continued

| Example | LCMS or NMR |
|---|---|
| 30 | ¹H NMR (400 MHz, DMSO-$d_6$): δ 8.69-8.65 (m, 1H), 8.36 (bs, 3H), 8.24 (d, J = 16.03 Hz, 2H), 7.89-7.82 (m, 1H), 7.79 (d, J = 8.24 Hz, 1H), 7.75-7.70 (m, 1H), 7.58 (d, J = 8.24 Hz, 1H), 7.17 (s, 1H), 6.43 (t, J = 1.83 Hz, 1H), 4.03-3.91 (m, 1H), 2.30 (s, 3H), 1.99-1.61 (m, 8H), 1.48-1.30 (m, 1H). |
| 31 | ¹H NMR (400 MHz, DMSO-$d_6$): δ 8.38 (bs, 3H), 8.20 (d, J = 2.14 Hz, 1H), 7.79-7.59 (m, 5H), 7.51-7.39 (m, 1H), 7.14-7.00 (m, 1H), 6.68-6.54 (m, 1H), 6.44-6.39 (m, 1H), 4.01-3.90 (m, 1H), 2.29 (s, 3H), 2.00-1.62 (m, 8H), 1.39-1.19 (m, 1H). |
| 32 | ¹H NMR (400 MHz, DMSO-$d_6$): δ 8.38 (bs, 3H), 8.22 (s, 1H), 7.74 (d, J = 8.54 Hz, 1H), 7.67 (s, 1H), 7.63-7.54 (m, 2H), 7.03-6.96 (m, 1H), 6.93 (s, 1H), 6.46-6.41 (m, 1H), 3.99-3.87 (m, 1H), 2.31 (s, 3H), 2.30 (s, 3H), 1.99-1.62 (m, 8H), 1.40-1.19 (m, 1H). |
| 33 | ¹H NMR (400 MHz, DMSO-$d_6$): δ 8.64 (d, J = 1.22 Hz, 1H), 8.38 (bs, 3H), 7.77 (d, J = 1.53 Hz, 1H), 7.62 (d, J = 7.02 Hz, 2H), 7.44-7.31 (m, 3H), 7.17 (d, J = 7.63 Hz, 1H), 7.13 (s, 1H), 6.92 (d, J = 7.93 Hz, 1H), 5.82-5.75 (m, 1H), 5.50 (s, 2H), 4.02-3.91 (m, 1H), 3.79 (s, 3H), 2.45-2.28 (m, 2H), 1.98-1.72 (m, 6H), 1.52-1.30 (m, 1H). |
| 34 | ¹H NMR (400 MHz, DMSO-$d_6$): δ 8.38 (bs, 3H), 7.77 (d, J = 8.70 Hz, 2H), 7.64 (d, J = 8.24 Hz, 2H), 7.39 (t, J = 7.79 Hz, 1H), 7.24 (d, J = 7.79 Hz, 1H), 7.20 (t, J = 1.83 Hz, 1H), 7.05 (s, 1H), 6.97 (dd, J = 8.24, 2.29 Hz, 1H), 6.77 (q, J = 6.87 Hz, 1H), 6.59 (s, 1H), 3.99-3.89 (m, 1H), 3.78 (s, 3H), 2.44-2.22 (m, 2H), 1.98-1.67 (m, 6H), 1.36-1.16 (m, 1H). |
| 35 | ¹H NMR (400 MHz, DMSO-$d_6$): δ 8.78 (t, J = 1.83 Hz, 1H), 8.31 (bs, 3H), 8.21 (t, J = 3.05 Hz, 1H), 7.75-7.66 (m, 4H), 7.33 (dt, J = 7.93, 1.83 Hz, 1H), 7.23-7.11 (m, 4H), 6.91 (d, J = 8.24 Hz, 1H), 4.00-3.89 (m, 1H), 3.77 (s, 3H), 2.65-2.27 (m, 2H), 1.98-1.68 (m, 6H), 1.46-1.27 (m, 1H). |
| 36 | ¹H NMR (400 MHz, CDCl₃): δ 7.70-7.62 (m, 3H), 7.41 (d, J = 1.98 Hz, 1H), 7.36 (dd, J = 8.54, 2.14 Hz, 1H), 6.78-6.70 (m, 1H), 6.66 (d, J = 6.71 Hz, 1H), 6.32 (d, J = 2.44 Hz, 1H), 6.14 (d, J = 1.53 Hz, 1H), 5.28 (s, 1H), 5.19 (d, J = 6.10 Hz, 2H), 4.43-4.29 (m, 1H), 4.11 (q, J = 7.02 Hz, 2H), 2.48-2.39 (m, 1H), 2.39 (s, 3H), 2.3-2.19 (m, 1H), 2.09-1.50 (m, 7H), 1.24 (t, J = 7.02 Hz, 3H). |
| 37 | ¹H NMR (400 MHz, DMSO-$d_6$) δ 8.41 (s, br, 1H), 8.13 (d, J = 8.0 Hz, 2H), 8.04 (d, J = 8.0 Hz, 2H), 7.50 (d, J = 8.4 Hz, 2H), 7.20 (d, J = 8.4 Hz, 2H), 4.21-4.28 (m, 2H), 3.88 (s, 3H), 3.17-3.26 (m, 2H) |
| 38 | ¹H NMR (400 MHz, DMSO-$d_6$) δ 13.95 (s, br, 1H), 8.46 (s, br, 2H), 8.19 (d, J = 8.0 Hz, 2H), 8.06 (d, J = 8.0 Hz, 2H), 7.71-7.78 (m, 1H), 7.64-7.71 (m, 2H), 7.52 (d, J = 8.0 Hz, 2H), 4.21-4.28 (m, 1H), 3.18-3.28 (m, 2H) |
| 39 | ¹H NMR (400 MHz, DMSO-$d_6$) δ 8.47 (s, br, 2H), 8.23-8.30 (m, 2H), 8.05 (d, J = 8.4 Hz, 2H), 7.52 (d, J = 8.4 Hz, 2H), 4.21-4.29 (m, 1H), 3.19-3.29 (m, 1H) |
| 40 | ¹H NMR (400 MHz, DMSO-$d_6$) δ 8.45 (s, br, 2H), 8.06-8.13 (m, 4H), 7.86 (d, J = 8.4 Hz, 2H), 7.55 (d, J = 8.4 Hz, 2H), 4.22-4.30 (m, 1H), 3.20-3.27 (m, 2H) |
| 41 | ¹H NMR (400 MHz, DMSO-$d_6$) δ 8.47 (s, br, 2H), 8.08-8.19 (m, 5H), 7.60-7.72 (m, 2H), 7.55 (d, J = 8.4 Hz, 2H), 4.22-4.31 (m, 1H), 3.20-3.27 (m, 2H) |
| 42 | ¹H NMR (400 MHz, DMSO-$d_6$) δ 8.42 (s, br, 2H), 8.23 (d, J = 7.6 Hz, 2H), 8.13 (d, J = 7.6 Hz, 2H), 7.96 (d, J = 7.6 Hz, 2H), 7.79 (d, J = 7.6 Hz, 2H), 7.50-7.58 (m, 4H), 7.42-7.48 (m, 1H), 4.25-4.31 (m, 1H), 3.21-3.27 (m, 2H) |
| 43 | ¹H NMR (400 MHz, DMSO-$d_6$) δ 13.93 (s, br, 1H), 9.77 (s, br, 1H), 8.44 (s, br, 2H), 8.14 (dd, J = 14.8, 8.8 Hz, 4H), 7.86 (d, J = 8.4 Hz, 2H), 7.63 (d, J = 8.4 Hz, 2H), 7.55 (d, J = 8.4 Hz, 2H), 4.23-4.32 (m, 1H), 3.20-3.28 (m, 2H) |

Table 4 shows the NMR or LCMS values of the compounds of Examples 44 to 120.

TABLE 4

| Example | LCMS or NMR |
|---|---|
| 44 | ¹H NMR (400 MHz, DMSO-$d_6$): δ 8.70 (t, J = 5.49 Hz, 1H), 8.20 (d, J = 2.14 Hz, 1H), 7.79-7.58 (m, 5H), 7.51-7.38 (m, 1H), 7.08 (s, 1H), 6.63 (s, 1H), 6.42 (d, J = 2.44 Hz, 1H), 4.06-3.90 (m, 1H), 2.30 (s, 3H), 2.01-1.63 (m, 9H), 1.42 (s, 9H). |
| 45 | ¹H NMR (400 MHz, DMSO-$d_6$): δ 13.05 (s, 1H), 8.46 (s, 2H), 8.20 (d, J = 2.14 Hz, 1H), 7.79 (m, 5H), 7.51-7.38 (m, 1H), 7.08 (s, 1H), 6.63 (s, 1H), 6.42 (d, J = 2.44 Hz, 1H), 4.06-3.90 (m, 1H), 2.30 (s, 3H), 2.01-1.63 (m, 9H). |
| 46 | ¹H NMR (400 MHz, DMSO-$d_6$): δ 8.85 (s, 1H), 8.70 (s, 1H), 8.43 (bs, 3H), 8.02 (d, J = 7.93 Hz, 2H), 7.75 (d, J = 8.54 Hz, 1H), 7.67-7.56 (m, 2H), 7.64-7.30 (m, 6H), 6.87 (q, J = 7.02 Hz, 1H), 4.28-4.18 (m, 1H), 3.18 (d, J = 6.10 Hz, 2H). |
| 47 | ¹H NMR (400 MHz, DMSO-$d_6$): δ 13.87 (s, 1H), 8.39 (bs, 3H), 7.72-7.60 (m, 2H), 7.60-7.50 (m, 1H), 7.48-7.32 (m, 4H), 7.06 (s, 1H), 6.71 (q, J = 6.71 Hz, 1H), 6.57 (s, 1H), 4.14-3.88 (m, 1H), 2.61-2.13 (m, 3H), 2.11-1.67 (m, 6H). |
| 48 | ¹H NMR (400 MHz, DMSO-$d_6$): δ 8.42 (bs, 3H), 7.73-7.45 (m, 7H), 7.41 (d, J = 2.14 Hz, 1H), 7.15-7.05 (m, 1H), 6.76 (q, J = 6.41 Hz, 1H), 6.66-6.56 (m, 1H), 4.04-3.88 (m, 1H), 2.58-2.14 (m, 2H), 2.07-1.59 (m, 6H), 1.47-1.20 (m, 1H). |
| 49 | ¹H NMR (400 MHz, DMSO-$d_6$): δ 8.54-8.30 (m, 4H), 7.87 (s, 1H), 7.66-7.56 (m, 2H), 7.36 (t, J = 8.24 Hz, 1H), 7.28 (d, J = 7.93 Hz, 2H), 7.19 (d, J = 7.93 Hz, 1H), 7.15 (s, 1H), 6.92 (d, J = 8.24 Hz, 1H), 5.94 (s, 1H), 5.31 (s, 2H), 3.98-3.86 (m, 1H), 3.80 (s, 3H), 2.45-2.11 (m, 4H), 2.07-1.65 (m, 3H), 1.45-1.21 (m, 2H). |
| 50 | ¹H NMR (400 MHz, DMSO-$d_6$): δ 8.79 (d, J = 0.92 Hz, 1H), 8.36 (bs, 3H), 8.23 (d, J = 2.44 Hz, 1H), 7.71 (d, J = 8.54 Hz, 1H), 7.66-7.54 (m, 3H), 7.46-7.37 (m, 3H), 7.23-7.14 (m, 1H), 6.84 (q, J = 6.41 Hz, 1H), 4.03-3.92 (m, 1H), 2.63-2.29 (m, 3H), 2.01-1.71 (m, 5H), 1.49-1.31 (m, 1H). |
| 51 | ¹H NMR (400 MHz, DMSO-$d_6$): δ 13.85 (s, 1H), 8.78 (s, 1H), 8.36 (bs, 3H), 8.27-8.19 (m, 1H), 7.72 (d, J = 7.93 Hz, 1H), 7.64-7.47 (m, 6H), 7.45-7.35 (m, 1H), 7.18 (s, 1H), 6.90 (s, 1H), 4.03-3.89 (m, 1H), 2.69-2.29 (m, 2H), 2.03-1.69 (m, 5H), 1.54-1.14 (m, 2H). |
| 52 | ¹H NMR (400 MHz, DMSO-$d_6$): δ 12.52 (s, 1H), 8.60 (s, 1H), 8.44 (bs, 3H), 8.33-8.17 (m, 1H), 7.85-7.69 (m, 1H), 7.43 (d, J = 3.05 Hz, 1H), 7.33 (t, J = 6.41 Hz, 1H), 7.18 (d, J = 8.24 Hz, 1H), 6.95 (s, 1H), 6.40 (s, 1H), 4.07-3.89 (m, 1H), 3.79-3.27 (m, 6H), 3.10-2.84 (m, 2H), 2.68-2.16 (m, 7H), 2.01-1.69 (m, 5H), 1.44-1.12 (m, 1H). |
| 53 | ¹H NMR (400 MHz, DMSO-$d_6$): δ 8.70 (t, J = 5.49 Hz, 1H), 8.15 (d, J = 2.14 Hz, 1H), 7.85-7.80 (m, 2H), 7.67 (d, J = 8.24 Hz, 1H), 7.60 (t, J = 1.83 Hz, 1H), 7.58-7.40 (m, 5H), 7.18 (q, J = 6.71 Hz, 1H), 6.76 (s, 1H), 6.39 |

TABLE 4-continued

| Example | LCMS or NMR |
|---|---|
| | (d, J = 2.14 Hz, 1H), 6.25 (s, 1H), 4.04 (q, J = 7.02 Hz, 2H), 3.84 (d, J = 5.80 Hz, 2H), 3.43-3.34 (m, 1H), 2.55-2.09 (m, 3H), 2.27 (s, 3H), 1.87-1.59 (m, 3H), 1.57-1.33 (m, 2H), 1.28-1.18 (m, 1H), 1.14 (t, J = 7.02 Hz, 3H). |
| 54 | $^1$H NMR (400 MHz, DMSO-$d_6$): δ 8.41 (s, 3H), 8.18 (d, J = 2.44 Hz, 1H), 8.00 (d, J = 8.54 Hz, 1H), 7.60 (d, J = 2.14 Hz, 1H), 7.56 (dd, J = 8.54, 2.14 Hz, 1H), 7.40 (q, J = 6.71 Hz, 1H), 7.35 (s, 1H), 7.24-7.14 (m, 1H), 6.39 (d, J = 2.44 Hz, 1H), 5.96 (s, 1H), 4.16-3.78 (m, 1H), 2.39-2.21 (m, 3H), 2.29 (s, 3H), 1.89-1.71 (m, 5H), 1.42-1.19 (m, 1H). |
| 55 | $^1$H NMR (400 MHz, DMSO-$d_6$): δ 8.44 (bs, 3H), 8.28-8.21 (m, 2H), 7.84 (d, J = 8.54 Hz, 1H), 7.81 (d, J = 2.75 Hz, 1H), 7.75-7.65 (m, 2H), 7.59 (dd, J = 8.54, 1.83 Hz, 1H), 7.30 (d, J = 4.58 Hz, 1H), 6.42 (d, J= 2.44 Hz, 1H), 6.17 (s, 1H), 4.01-3.88 (m, 1H), 2.56-2.36 (m, 2H), 2.30 (s, 3H), 2.04-1.72 (m, 6H), 1.52-1.28 (m, 1H). |
| 56 | $^1$H NMR (400 MHz, DMSO-$d_6$): δ 8.48 (s, 3H), 8.24 (d, J = 2.14 Hz, 1H), 8.17 (d, J = 4.58 Hz, 1H), 7.96 (s, 1H), 7.85 (d, J = 8.54 Hz, 1H), 7.76-7.69 (m, 2H), 7.65 (d, J = 7.93 Hz, 2H), 7.61 (d, J = 8.54 Hz, 1H), 7.49 (d, J = 7.93 Hz, 2H), 7.32 (d, J = 4.58 Hz, 1H), 6.43 (d, J = 2.14 Hz, 1H), 4.31-4.19 (m, 1H), 3.27-3.18 (m, 2H), 2.31 (s, 3H). |
| 57 | $^1$H NMR (400 MHz, DMSO-$d_6$): δ 8.68 (t, J = 2.29 Hz, 1H), 8.37 (s, 2H), 8.24 (d, J = 16.03 Hz, 2H), 7.90-7.82 (m, 1H), 7.80 (d, J = 8.24 Hz, 1H), 7.73 (t, J = 1.83 Hz, 1H), 7.58 (d, J = 8.24 Hz, 1H), 7.18 (s, 1H), 6.43 (t, J = 1.83 Hz, 1H), 4.03-3.93 (m, 1H), 2.30 (s, 3H), 1.52-1.12 (m, 2H). |
| 58 | $^1$H NMR (400 MHz, DMSO-$d_6$): δ 8.38 (s, 2H), 7.77 (d, J = 8.70 Hz, 2H), 7.64 (d, J = 8.24 Hz, 2H), 7.39 (t, J = 7.79 Hz, 1H), 7.24 (d, J = 7.79 Hz, 1H), 7.20 (s, 1H), 7.06 (s, 1H), 6.97 (dd, J = 8.24, 2.29 Hz, 1H), 6.80 (q, J = 6.87 Hz, 1H), 6.62 (s, 1H), 4.02-3.92 (m, 1H), 3.81 (s, 3H), 2.57-2.26 (m, 3H), 2.00-1.69 (m, 5 H), 1.41-.17 (m, 1H). |
| 59 | $^1$H NMR (400 MHz, DMSO-$d_6$): δ 8.74 (t, J = 5.19 Hz, 1H), 8.18 (d, J = 2.44 Hz, 1H), 7.86 (d, J = 7.32 Hz, 3H), 7.70 (d, J = 8.54 Hz, 1H), 7.64 (d, J = 2.14 Hz, 1H), 7.62-7.44 (m, 5H), 7.22 (q, J = 6.71 Hz, 1H), 6.79 (s, 1H), 6.42 (d, J = 2.44 Hz, 1H), 6.28 (s, 1H), 3.89 (d, J = 5.80 Hz, 2H), 3.62 (s, 3H), 3.52-3.42 (m, 1H), 2.46-2.12 (m, 3H), 2.31 (s, 3H), 1.90-1.64 (m, 3H), 1.62-1.38 (m, 2H), 1.34-1.19 (m, 1H). |
| 60 | $^1$H NMR (400 MHz, DMSO-$d_6$): δ 13.83 (s, 1H), 8.39 (bs, 3H), 7.80 (d, J = 7.93 Hz, 2H), 7.64 (d, J = 8.24 Hz, 2H), 7.44 (t, J = 8.24 Hz, 1H), 7.39-7.31 (m, 2H), 7.08 (dd, J = 6.10, 2.14 Hz, 1H), 7.04-6.89 (m, 1H), 6.80 (q, J = 7.02 Hz, 1H), 6.61-6.43 (m, 1H), 4.85 (q, J = 8.85 Hz, 2H), 4.02-3.89 (m, 1H), 2.05-1.69 (m, 7H), 1.44-1.15 (m, 2H). |
| 61 | $^1$H NMR (400 MHz, DMSO-$d_6$): δ 13.85 (s, 1H), 8.40 (bs, 3H), 7.76 (d, J = 7.93 Hz, 2H), 7.63 (d, J = 7.93 Hz, 2H), 7.36 (t, J = 7.93 Hz, 1H), 7.27-7.16 (m, 2H), 7.07-6.97 (m, 1H), 6.95 (d, J = 8.54 Hz, 1H), 6.80 (q, J = 7.32 Hz, 1H), 6.63-6.45 (m, 1H), 4.01-3.92 (m, 1H), 3.88 (d, J = 7.02 Hz, 2H), 2.57-2.23 (m, 2H), 2.03-1.67 (m, 5H), 1.41-1.17 (m, 3H), 0.63-0.54 (m, 2H), 0.38-0.28 (m, 2H). |
| 62 | $^1$H NMR (400 MHz, DMSO-$d_6$): δ 13.85 (s, 1H), 8.42 (s, 3H), 7.77 (d, J = 8.24 Hz, 2H), 7.63 (d, J = 8.24 Hz, 2H), 7.37 (t, J = 7.93 Hz, 1H), 7.22 (d, J = 7.93 Hz, 1H), 7.19 (s, 1H), 7.11-6.99 (m, 1H), 6.95 (dd, J = 8.09, 1.83 Hz, 1H), 6.80 (q, J = 6.71 Hz, 1H), 6.67- |
| | 6.53 (m, 1H), 4.01-3.90 (m, 1H), 3.81 (d, J = 6.41 Hz, 2H), 2.57-2.24 (m, 2H), 2.10-1.70 (m, 7H), 1.41-1.21 (m, 1H), 0.98 (d, J = 6.71 Hz, 6H). |
| 63 | $^1$H NMR (400 MHz, DMSO-$d_6$): δ 13.83 (s, 1H), 8.37 (s, 3H), 7.73 (d, J = 8.24 Hz, 2H), 7.60 (d, J = 8.24 Hz, 2H), 7.34 (t, J = 7.93 Hz, 1H), 7.18 (d, J = 7.93 Hz, 1H), 7.15 (s, 1H), 7.07-6.95 (m, 1H), 6.91 (dd, J = 8.09, 1.83 Hz, 1H), 6.77 (q, J = 6.71 Hz, 1H), 6.65-6.49 (m, 1H), 4.05 (q, J = 7.02 Hz, 2H), 3.97-3.88 (m, 1H), 2.54-2.19 (m, 4H), 1.98-1.66 (m, 5H), 1.30 (t, J = 7.02 Hz, 3H). |
| 64 | $^1$H NMR (400 MHz, DMSO-$d_6$): δ 13.78 (s, 1H), 8.37 (s, 3H), 7.98 (s, 1H), 7.66 (s, 1H), 7.58 (d, J = 8.54 Hz, 1H), 7.48 (d, J = 8.85 Hz, 1H), 7.40 (d, J = 1.83 Hz, 1H), 7.12-6.98 (m, 1H), 6.87 (q, J = 6.10 Hz, 1H), 7.60-6.48 (m, 1H), 3.97-3.87 (m, 1H), 3.90 (s, 3H), 2.53-2.21 (m, 4H), 1.98-1.66 (m, 4H), 1.37-1.17 (m, 1H). |
| 65 | $^1$H NMR (400 MHz, CDCl$_3$): δ 7.65 (d, J = 8.54 Hz, 1H), 7.63 (d, J = 2.44 Hz, 1H), 7.41 (d, J = 2.14 Hz, 1H), 7.38 (dd, J = 8.39, 2.14 Hz, 1H), 6.75 (s, 1H), 6.59 (q, J = 6.41 Hz, 1H), 6.32 (d, J = 2.44 Hz, 1H), 6.14 (d, J = 2.44 Hz, 1H), 4.43-4.28 (m, 1H), 4.18 (q, J = 7.02 Hz, 2H), 2.41 (s, 3H), 2.49-2.17 (m, 3H), 2.02-1.64 (m, 4H), 1.64-1.50 (m, 2H), 1.42 (s, 9H), 1.26 (t, J = 7.02 Hz, 3H). |
| 66 | $^1$H NMR (400 MHz, DMSO-$d_6$): δ 13.85 (s, 1H), 8.42 (bs, 3H), 7.63 (d, J = 8.54 Hz, 1H), 7.52 (dd, J = 8.54, 1.53 Hz, 1H), 7.43 (d, J = 1.83 Hz, 1H), 7.09 (q, J = 6.71 Hz, 1H), 7.01 (s, 1H), 6.48 (s, 1H), 5.93 (s, 1H), 4.32-4.06 (m, 2H), 4.0-3.74 (m, 1H), 2.61-2.13 (m, 5H), 2.11-1.69 (m, 5H), 1.43-1.13 (m, 1H). |
| 67 | $^1$H NMR (400 MHz, DMSO-$d_6$): δ 7.61 (d, J = 8.54 Hz, 1H), 7.48 (d, J = 7.93 Hz, 1H), 7.39 (s, 1H), 7.06 (q, J = 6.41 Hz, 1H), 6.81 (s, 1H), 6.39 (bs, 2H), 6.22 (s, 1H), 5.91 (s, 1H), 4.32-4.08 (m, 2H), 3.98-3.72 (m, 2H), 3.27-3.09 (m, 1H), 2.56-2.14 (m, 5H), 1.91-1.66 (m, 4H), 1.59-1.39 (m, 1H), 1.33-1.09 (m, 1H). |
| 68 | $^1$H NMR (400 MHz, DMSO-$d_6$): δ 13.84 (s, 1H), 8.41 (s, 2H), 8.01 (s, 1H), 7.70 (s, 1H), 7.61 (d, J = 8.54 Hz, 1H), 7.52 (d, J = 8.84 Hz, 1H), 7.44 (d, J = 1.83 Hz, 1H), 7.13-7.03 (m, 1H), 6.91 (q, J = 6.10 Hz, 1H), 6.63-6.53 (m, 1H), 4.0-3.90 (m, 1H), 3.94 (s, 3H), 2.56-2.24 (m, 4H), 2.00-1.71 (m, 5H), 1.39-1.20 (m, 1H). |
| 69 | $^1$H NMR (400 MHz, DMSO-$d_6$): δ 8.87-8.82 (m, 1H), 8.73-8.67 (m, 1H), 8.00 (d, J = 8.24 Hz, 2H), 7.69 (d, J = 8.24 Hz, 1H), 7.53-7.35 (m, 4H), 7.24 (q, J = 6.10 Hz, 1H), 6.03 (s, 1H), 4.49 (d, J = 15.87 Hz, 1H), 4.19 (d, J = 16.48 Hz, 1H), 4.10-4.02 (m, 1H), 3.92-3.79 (m, 2H), 3.25-3.08 (m, 2H), 2.37-2.27 (m, 2H). |
| 70 | $^1$H NMR (400 MHz, DMSO-$d_6$): δ 8.87-8.81 (m, 1H), 8.72-8.66 (m, 1H), 7.92 (d, J = 8.24 Hz, 2H), 7.66 (d, J = 8.24 Hz, 1H), 7.52-7.34 (m, 4H), 7.22 (q, J = 7.02 Hz, 1H), 6.02 (s, 1H), 4.48 (d, J = 15.87 Hz, 1H), 4.18 (d, J = 16.48 Hz, 1H), 3.98-3.80 (m, 2H), 3.58-3.15 (m, 2H), 2.85-2.70 (m, 1H), 2.40-2.27 (m, 2H). |
| 71 | $^1$H NMR (400 MHz, DMSO-$d_6$): δ 13.80 (s, 1H), 8.34 (bs, 3H), 8.30 (s, 1H), 7.77-7.65 (m, 3H), 7.59 (d, J = 2.14 Hz, 1H), 7.46-7.36 (m, 2H), 7.29 (t, J = 7.32 Hz, 1H), 7.03-6.87 (m, 1H), 6.92 (d, J = 6.41 Hz, 1H), 6.52-6.40 (m, 1H), 4.03-3.91 (m, 1H), 2.57-2.19 (m, 2H), 2.00-1.64 (m, 5H), 1.38-1.12 (m, 2H). |
| 72 | $^1$H NMR (400 MHz, DMSO-$d_6$): δ 8.67 (d, J = 14.95 Hz, 2H), 8.32 (s, 1H), 8.00 (d, J = 7.62 Hz, 2H), 7.83 (d, J = 8.54 Hz, 1H), 7.73 (d, J = |

| Example | LCMS or NMR |
|---|---|
|  | 8.24 Hz, 1H), 7.66 (dd, J = 8.54, 2.14 Hz, 1H), 7.61 (d, J = 2.14 Hz, 1H), 7.48-7.35 (m, 4H), 7.32 (t, J = 7.63 Hz, 1H), 7.07 (q, J = 6.41 Hz, 1H), 4.23-4.11 (m, 1H), 3.17 (d, J = 5.49 Hz, 2H). |
| 73 | $^1$H NMR (400 MHz, DMSO-$d_6$): δ 8.86 (d, J = 1.53 Hz, 1H), 8.71 (s, 1H), 8.08 (s, 1H), 8.01 (d, J = 7.93 Hz, 2H), 7.93 (d, J = 1.53 Hz, 1H), 7.74 (d, J = 8.24 Hz, 1H), 7.55 (dd, J = 8.54, 2.14 Hz, 1H), 7.51 (d, J = 2.14 Hz, 1H), 7.41 (d, J = 7.93 Hz, 2H), 7.18 (q, J = 6.41 Hz, 1H), 6.96 (s, 1H), 4.18-4.09 (m, 1H), 3.24-3.10 (m, 2H). |
| 74 | $^1$H NMR (400 MHz, DMSO-$d_6$): δ 13.83 (s, 1H), 8.46 (bs, 3H), 8.01 (s, 1H), 7.86 (s, 1H), 7.63 (d, J = 8.24 Hz, 1H), 7.55 (d, J = 8.54 Hz, 1H), 7.46 (d, J = 2.14 Hz, 1H), 7.04-6.94 (m, 1H), 6.91 (q, J = 6.41 Hz, 1H), 6.87 (s, 1H), 6.54-6.41 (m, 1H), 3.98-3.87 (m, 1H), 2.48-2.13 (m, 2H), 2.09-1.72 (m, 5H), 1.44-1.21 (m, 2H). |
| 75 | $^1$H NMR (400 MHz, DMSO-$d_6$): δ 13.85 (s, 1H), 8.33 (bs, 3H), 7.59 (d, J = 8.24 Hz, 1H), 7.50 (d, J = 8.54 Hz, 1H), 7.40 (d, J = 2.14 Hz, 1H), 6.98 (q, J = 6.10 Hz, 2H), 6.56-6.39 (m, 1H), 5.71 (s, 1H), 4.03-3.91 (m, 1H), 2.93-2.03 (m, 6H), 2.00-1.66 (m, 7H), 1.35-1.16 (m, 2H). |
| 76 | $^1$H NMR (400 MHz, DMSO-$d_6$): δ 13.84 (s, 1H), 8.39 (bs, 3H), 7.65 (d, J = 8.54 Hz, 1H), 7.57 (d, J = 8.54 Hz, 1H), 7.40 (d, J = 8.54 Hz, 2H), 7.36 (d, J = 2.14 Hz, 1H), 7.11 (d, J = 8.85 Hz, 2H), 7.10-6.98 (m, 1H), 6.80 (q, J = 6.41 Hz, 1H), 6.60-6.48 (m, 1H), 4.03-3.91 (m, 1H), 3.83 (s, 3H), 2.61-2.23 (m, 2H), 2.02-1.70 (m, 5H), 1.41-1.19 (m, 2H). |
| 77 | $^1$H NMR (400 MHz, DMSO-$d_6$): δ 13.83 (s, 1H), 8.39 (bs, 3H), 7.61 (d, J = 8.24 Hz, 1H), 7.51 (d, J = 8.24 Hz, 1H), 7.31 (d, J = 1.83 Hz, 1H), 7.05-6.87 (m, 1H), 6.92 (q, J = 6.41 Hz, 1H), 6.53-6.42 (m, 1H), 5.83 (s, 1H), 4.01-3.87 (m, 1H), 2.56-2.08 (m, 2H), 2.05-1.63 (m, 5H), 1.38-1.18 (m, 2H), 1.29 (s, 12H). |
| 78 | $^1$H NMR (400 MHz, DMSO-$d_6$): δ 8.87-8.81 (m, 1H), 8.74-8.65 (m, 1H), 8.01 (d, J = 8.24 Hz, 2H), 7.72 (d, J = 8.54 Hz, 1H), 7.51 (dd, J = 8.54, 2.14 Hz, 1H), 7.40 (d, J = 8.24 Hz, 2H), 7.35 (d, J = 2.14 Hz, 1H), 7.29 (q, J = 6.71 Hz, 1H), 5.94 (s, 1H), 4.13-4.01 (m, 1H), 3.26-3.05 (m, 2H), 2.19 (d, J = 16.78 Hz, 2H), 1.35 (s, 6H, 1.31 (s, 6H). |
| 79 | $^1$H NMR (400 MHz, DMSO-$d_6$): δ 9.90 (s, 1H), 8.91 (s, 1H), 8.16 (d, J = 2.14 Hz, 1H), 7.71-7.53 (m, 4H), 7.33-7.21 (m, 1H), 6.79 (s, 1H), 6.39 (d, J = 2.14 Hz, 2H), 4.11-4.05 (m, 1H), 3.73-3.56 (m, 2H), 2.40-2.06 (m, 4H), 2.27 (s, 3H), 1.90-1.53 (m, 2H), 1.38-1.14 (m, 2H). |
| 80 | $^1$H NMR (400 MHz, DMSO-$d_6$): δ 8.18 (s, 1H), 7.77-7.55 (m, 4H), 7.29-7.17 (m, 1H), 6.79-6.70 (m, 1H), 6.42 (s, 2H), 6.30 (s, 2H), 3.79-3.68 (m, 1H), 3.09-2.75 (m, 2H), 2.41-2.11 (m, 2H), 2.31 (s, 3H), 2.05-1.53 (m, 4H), 1.44-1.04 (m, 2H). |
| 81 | $^1$H NMR (400 MHz, DMSO-$d_6$): δ 8.84 (s, 1H), 8.70 (s, 1H), 8.01 (d, J = 8.24 Hz, 2H), 7.68 (d, J = 8.24 Hz, 1H), 7.52-7.45 (m, 2H), 7.40 (d, J = 8.24 Hz, 2H), 7.26 (q, J = 6.41 Hz, 1H), 5.97 (s, 1H), 4.35-4.25 (m, 2H), 4.17 (t, J = 6.10 Hz, 1H), 3.92 (t, J = 4.88 Hz, 2H), 3.17 (t, J = 5.49 Hz, 2H), 2.63-2.26 (m, 2H). |
| 82 | $^1$H NMR (400 MHz, DMSO-$d_6$): δ 8.44 (bs, 3H), 7.72-7.38 (m, 4H), 7.15-7.01 (m, 1H), 6.63-6.51 (m, 1H), 5.97-5.87 (m, 1H), 4.65-4.49 (m, 1H), 4.39-4.15 (m, 2H), 4.04-3.78 (m, 2H), 2.57-2.11 (m, 2H), 2.02-1.60 (m, 7H), 1.40-1.15 (m, 2H). |
| 83 | $^1$H NMR (400 MHz, DMSO-$d_6$): δ 10.33 (s, 1H), 8.99 (s, 1H), 7.62 (d, J = 4.88 Hz, 1H), 7.50 (dd, J = 8.54, 2.14 Hz, 1H), 7.42 (d, J = 2.29 Hz, 1H), 7.08 (q, J = 6.71 Hz, 1H), 7.00-6.88 (m, 1H), 6.54-6.44 (m, 1H), 5.90 (s, 1H), 4.53-4.41 (m, 1H), 4.36-4.17 (m, 2H), 3.90-3.81 (m, 2H), 3.17-2.93 (m, 2H), 2.48-2.11 (m, 5H), 2.00-1.62 (m, 5H). |
| 84 | $^1$H NMR (400 MHz, DMSO-$d_6$): δ 8.68 (d, J = 1.83 Hz, 1H), 8.29-8.21 (m, 2H), 7.90-7.76 (m, 2H), 7.72 (d, J = 1.83 Hz, 1H), 7.58 (d, J = 8.54 Hz, 1H), 7.18 (s, 1H), 6.43 (d, J = 2.14 Hz, 1H), 4.32-4.21 (m, 1H), 3.21-2.93 (m, 2H), 2.37-2.11 (m, 4H), 2.30 (s, 3H), 2.03-1.67 (m, 4H). |
| 85 | $^1$H NMR (400 MHz, DMSO-$d_6$): δ 7.58 (d, J = 7.93 Hz, 1H), 7.44 (d, J = 7.93 Hz, 1H), 7.38 (s, 1H), 7.06 (q, J = 6.41 Hz, 1H), 6.88-6.77 (m, 1H), 6.44 (s, 1H), 6.23 (s, 1H), 5.91 (s, 1H), 4.36-4.17 (m, 2H), 3.97-3.75 (m, 2H), 3.52-3.06 (m, 1H), 2.61-2.11 (m, 5H), 1.91-1.64 (m, 4H), 1.53-1.35 (m, 1H), 1.33-1.07 (m, 1H). |
| 86 | $^1$H NMR (400 MHz, DMSO-$d_6$): δ 8.76 (t, J = 5.49 Hz, 1H), 7.86 (d, J = 7.32 Hz, 2H), 7.65-7.37 (m, 5H), 7.07 (q, J = 7.02 Hz, 1H), 6.81 (s, 1H), 6.40 (bs, 1H), 6.23 (s, 1H), 5.91 (s, 1H), 4.31-4.02 (m, 1H), 3.89 (d, J = 5.80 Hz, 2H), 3.54-3.32 (m, 3H), 2.59-2.15 (m, 3H), 2.03-1.37 (m, 5H), 1.33-1.22 (m, 2H), 1.18 (t, J = 7.02 Hz, 3H). |
| 87 | $^1$H NMR (400 MHz, DMSO-$d_6$): δ 8.99 (s, 1H), 7.76 (d, J = 7.93 Hz, 2H), 7.63 (d, J = 7.63 Hz, 2H), 7.39 (t, J = 7.93 Hz, 1H), 7.23 (d, J = 7.93 Hz, 1H), 7.20 (s, 1H), 6.96 (d, J = 8.24 Hz, 1H), 6.94-6.87 (m, 1H), 6.80 (q, J = 7.02 Hz, 1H), 6.58-6.44 (m, 1H), 4.53-4.41 (m, 1H), 3.81 (s, 3H), 3.17-2.94 (m, 2H), 2.54-2.08 (m, 4H), 1.96-1.63 (m, 4H). |
| 88 | $^1$H NMR (400 MHz, DMSO-$d_6$): δ 9.00 (s, 1H), 7.86-7.77 (m, 2H), 7.65 (d, J = 6.41 Hz, 2H), 7.59-7.48 (m, 3H), 7.28-7.18 (m, 1H), 7.06-6.90 (m, 1H), 6.88-6.76 (m, 1H), 6.69-6.49 (m, 1H), 4.53-4.41 (m, 1H), 3.16-2.95 (m, 2H), 2.54-2.09 (m, 3H), 1.95-1.63 (m, 4H), 1.29-1.21 (m, 1H). |
| 89 | $^1$H NMR (400 MHz, DMSO-$d_6$): δ 13.09 (s, 1H), 10.38 (s, 1H), 8.99 (s, 1H), 7.76 (d, J = 8.24 Hz, 2H), 7.63 (d, J = 7.93 Hz, 2H), 7.39 (t, J = 7.93 Hz, 1H), 7.23 (d, J = 7.93 Hz, 1H), 7.20 (s, 1H), 6.98 (d, J = 8.24 Hz, 1H), 6.92 (s, 1H), 6.80 (q, J = 7.02 Hz, 1H), 6.51 (s, 1H), 4.53-4.41 (m, 1H), 3.81 (s, 3H), 3.17-2.94 (m, 2H), 2.48-2.11 (m, 4H), 1.96-1.64 (m, 4H). |
| 90 | $^1$H NMR (400 MHz, DMSO-$d_6$): δ 13.78 (s, 1H), 8.57 (s, 1H), 8.41 (s, 1H), 7.78 (d, J = 8.24 Hz, 2H), 7.63 (d, J = 8.24 Hz, 2H), 7.56-7.45 (m, 3H), 7.21 (t, J = 9.16 Hz, 1H), 7.11-6.97 (m, 1H), 6.78 (q, J = 6.71 Hz, 1H), 6.65-6.51 (m, 1H), 3.95-3.88 (m, 1H), 2.54-2.22 (m, 2H), 1.99-1.67 (m, 5H), 1.37-1.17 (m, 2H). |
| 91 | $^1$H NMR (400 MHz, DMSO-$d_6$): δ 8.50 (bs, 3H), 8.43 (s, 1H), 8.24 (d, J = 2.14 Hz, 1H), 8.00 (d, J = 7.32 Hz, 2H), 7.80 (d, J = 8.24 Hz, 1H), 7.69 (d, J = 2.14 Hz, 1H), 7.63 (d, J = 8.54 Hz, 1H), 7.56 (q, J = 6.41 Hz, 1H), 7.36 (d, J = 8.24 Hz, 2H), 6.45 (d, J = 2.14 Hz, 1H), 4.30-4.14 (m, 1H), 3.18 (d, J = 5.80 Hz, 2H), 2.32 (s, 3H). |
| 92 | $^1$H NMR (400 MHz, DMSO-$d_6$): δ 7.78 (d, J = 8.24 Hz, 2H), 7.64 (d, J = 7.93 Hz, 2H), 7.59-7.47 (m, 3H), 7.28-7.18 (m, 1H), 6.88-6.74 (m, 2H), 6.55 (s, 2H), 6.29 (d, J = 2.44 Hz, 1H), 3.24-3.10 (m, 1H), 2.59-2.15 (m, 3H), 1.92-1.66 (m, 4H), 1.60-1.14 (m, 2H). |
| 93 | $^1$H NMR (400 MHz, DMSO-$d_6$): δ 8.79 (d, J = 1.83 Hz, 1H), 8.25 (s, 1H), 7.65 (d, J = 8.24 Hz, 1H), 7.52-7.44 (m, 2H), 7.26-7.15 (m, 2H), |

TABLE 4-continued

| Example | LCMS or NMR |
|---|---|
|  | 6.01 (s, 1H), 4.47 (d, J = 16.17 Hz, 1H), 4.38-4.27 (m, 1H), 4.17 (d, J = 16.17 Hz, 1H), 3.92-3.77 (m, 2H), 3.20-2.96 (m, 2H), 2.63-2.47 (m, 2H), 2.39-2.11 (m, 5H), 2.01-1.71 (m, 3H). |
| 94 | $^1$H NMR (400 MHz, DMSO-$d_6$): δ 10.33 (s, 1H), 8.97 (s, 1H), 7.63 (d, J = 8.54 Hz, 1H), 7.52 (dd, J = 9.46, 1.83 Hz, 1H), 7.43 (d, J = 2.14 Hz, 1H), 7.09 (q, J = 7.02 Hz, 1H), 6.91 (s, 1H), 6.44 (s, 1H), 5.92 (s, 1H), 4.52-4.40 (m, 1H), 4.25 (d, J = 15.87 Hz, 1H), 4.10 (d, J = 15.87 Hz, 1H), 3.93-3.74 (m, 2H), 3.15-2.94 (m, 2H), 2.47-2.09 (m, 6H), 2.00-1.62 (m, 4H). |
| 95 | $^1$H NMR (400 MHz, DMSO-$d_6$): δ 7.78 (d, J = 8.54 Hz, 2H), 7.63 (d, J = 7.93 Hz, 2H), 7.58-7.47 (m, 3H), 7.26-7.19 (m, 1H), 6.85-6.73 (m, 2H), 6.56 (s, 2H), 6.32 (s, 1H), 3.78-3.65 (m, 1H), 3.10-2.72 (m, 2H), 2.40-2.05 (m, 4H), 2.00-1.72 (m, 3H), 1.66-1.50 (m, 2H). |
| 96 | LCMS [M + H]621.25 |
| 97 | LCMS [M + H]553.18 |
| 98 | LCMS [M + H]551.19 |
| 99 | LCMS [M + H]551.17 |
| 100 | LCMS [M + H]551.17 |
| 101 | LCMS [M + H] 553.18 |
| 102 | LCMS [M + H] 553.18 |
| 103 | LCMS [M + H] 590.10 |
| 104 | LCMS [M + H] 588.13 |
| 105 | LCMS [M + H] 605.12 |
| 106 | LCMS [M + H] 605.12 |
| 107 | LCMS [M + H] 619.14 |
| 108 | LCMS [M + H] 565.18 |
| 109 | LCMS [M + H] 563.20 |
| 110 | LCMS [M + H] 563.17 |
| 111 | LCMS [M + H] 563.17 |
| 112 | LCMS [M + H] 563.17 |
| 113 | LCMS [M + H] 563.17 |
| 114 | LCMS [M + H] 565.18 |
| 115 | LCMS [M + H] 565.18 |
| 116 | LCMS [M + H] 565.18 |
| 117 | LCMS [M + H] 565.18 |
| 118 | LCMS [M + H] 593.21 |
| 119 | LCMS [M + H] 591.20 |
| 120 | LCMS [M + H] 631.14 |

<Experimental Example 2> Inhibition of Tryptophan Hydroxylase Activity by Compounds According to the Present Invention In order to confirm the inhibitory effect of the compound represented by formula 1 according to the present invention on the tryptophan hydroxylase activity, it was measured using a TPH1 (tryptophan hydroxylase 1) inhibitor screening assay kit (BPS Bioscience, Catalog #72053). The TPH1 inhibitor screening assay kit was used according to the manufacturer's manual. The results are shown in table below.

Particularly, the synthesized compound was dissolved in DMSO, which was added to a 96-well microplate (10 µℓ/well), to which TPH1 enzyme was added (40 µℓ/well). Then, TPH1 reaction solution was added to the microplate (50 µℓ/well) and the microplate was shaded with aluminum foil. The microplate was transferred to 4° C. environment, shaken carefully and incubated for 4 hours. After adding a quench solution to the microplate (10 µℓ/well), the TPH1 activity was measured by reading the degree of fluorescence color development with a Flexstation3 microplate reader. At this time, the excitation spectrum was 300 nm and the emission spectrum was 360 nm.

TABLE 5

| Example | IC$_{50}$ (µM) |
|---|---|
| 8 | 0.036 |
| 12 | 0.297 |
| 22 | 0.993 |
| 23 | 0.578 |
| 24 | 0.565 |
| 26 | 0.679 |
| 30 | 1.510 |
| 31 | 0.114 |
| 32 | 1.823 |
| 34 | 0.281 |
| 45 | 0.098 |
| 46 | 8.721 |
| 48 | 0.433 |
| 58 | 0.204 |
| 66 | 0.125 |
| 67 | 0.091 |
| 69 | 0.263 |
| 70 | 0.371 |
| 75 | 0.443 |
| 79 | 0.185 |
| 80 | 0.194 |
| 83 | 1.150 |
| 84 | 0.307 |
| 85 | 0.940 |
| 87 | 0.741 |
| 89 | 0.409 |
| 91 | 0.208 |
| 94 | 0.209 |

As shown in Table 5, the compounds of examples according to the present invention showed low IC$_{50}$ values of µM level, indicating that the inhibitory effect of the compounds on TPH1 was excellent even at low concentrations. Specifically, most of the example compounds exhibited IC$_{50}$ values of 1 µM or less, and in particular, the compounds of Examples 8, 45 and 67 showed IC$_{50}$ values of nM level (36 nM, 98 nM and 91 nM, respectively), indicating that the inhibitory effect of the compounds on TPH1 was excellent even at significantly low concentrations.

As described above, the compound represented by formula 1 according to the present invention had an excellent inhibitory effect on TPH1, so that the compound can be effectively used for the prevention or treatment of metabolic disorder, cancer, digestive or circulatory system disorders, which are the diseases related to TPH1 activity.

<Experimental Example 3> Evaluation of Efficacy in Inflammatory Bowel Disorder Animal Model In order to evaluate the therapeutic effect of the compound represented by formula 1 according to the present invention, the efficacy in the inflammatory bowel disorder animal model was evaluated. As a compound for evaluating the efficacy, the compound of Example 53 according to the present invention was used, and as a comparative example, LX1606 ((2S)-2-Amino-3-[4-[2-amino-6-[[(1R)-1-[4-chloro-2-(3-methylpyrazol-1-yl)phenyl]-2,2,2-trifluoro-ethyl]oxy]pyrimidin-4-yl]phenyl]propionic acid ethyl ester), well known as a THF inhibitor, was used. The specific experimental methods are as follows.

<Experimental Animal and Compound Preparation and Administration>

C57BL/6J (Jackson Lab) male mice weighing 25±2 g at 9 weeks of age were used, and all the mice were fed freely by providing standard experimental feed. The compound of Example 53 and LX1606 were dissolved in 0.25% methylcellulose (MC) solution, which was orally administered to mice at the dose of 100 and 300 mg/kg/time using a 1 mL syringe. The compound of Example 53 and LX1606 were administered for 7 days, starting one day prior to dextran sulfate sodium (DSS) administration. Before and after the administration, the samples of colon tissue were collected from each mouse treated with the compound of Example 53 or the control drug (LX1606) to confirm clinical symptoms. Data are expressed as mean±standard error of mean (SEM), and all statistical analyses were performed using GraphPad Prism (version 5.0, GraphPad Software, La Jolla, Calif.). Differences in mean between groups were statistically analyzed by two-way analysis of variance (ANOVA) and multiple comparison tests to reveal the differences between the experimental groups. P<0.05 was considered statistically significant. The compounds, administration methods, and number of mice administered are shown in table 6 below.

TABLE 6

| Compound | Administration | Number (mouse) |
| --- | --- | --- |
| Control | Water | 5 |
| Vehicle | methycellulose + 2.5% DSS | 7 |
| LX1606 | 100 mg/kg + 2.5% DSS | 7 |
| LX1606 | 300 mg/kg + 2.5% DSS | 7 |
| Compound of Example 53 | 100 mg/kg + 2.5% DSS | 7 |
| Compound of Example 53 | 300 mg/kg + 2.5% DSS | 7 |

Experimental Example 3-1. Dextran Sodium Sulfate: Induction and Evaluation of DSS Colitis Enteritis was induced in mice by freely drinking 2.5% DSS (molecular weight: 36,000-50,000 M.Wt; manufactured by MP Biomedicals, Canada) aqueous solution for 6 days, and the body weight, stiffness of the stool, and the presence or absence of bloody stool were observed daily from the start of the administration. For histological evaluation (H&E), colon permeability measurement and myeloperoxidase (MPO) activity measurement, colon tissues were collected and stored at −80° C. until immediately before use. In addition, the severity of colitis was evaluated by colon length and histological examination 6 days after the start of DSS administration and 5 days after recovery. FIG. 1 shows images of the collected colon tissues, and FIG. 2 shows a graph illustrating the colon length for each experimental group.

Figure 2:
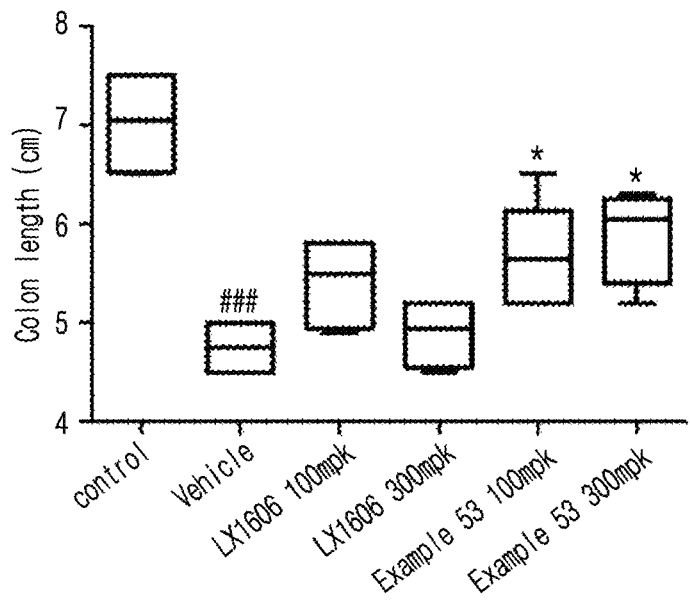
FIG. 2 is a graph showing the colon length for each experimental group. (#: P vs negative control, *: P vs positive control group) *mpk=mg/kg

As shown in FIGS. 1 and 2, it was confirmed that the colon length of the groups treated with the compound of Example 53 at the concentrations of 100 mg/kg and 300 mg/kg was longer than that of the group treated with vehicle. On the other hand, the colon length of the groups treated with LX1606 at the concentrations of 100 mg/kg and 300 mg/kg was not longer than that of the group treated with vehicle. In addition, when comparing the degree of colon loose, the colon of the group treated with vehicle was loose most, and the colon of the group treated with the compound of Example 53 was loose least, which was most similar to the normal colon.

1) Evaluation of Severity of Colitis (Disease Activity Index, DAI)

Figure 3:
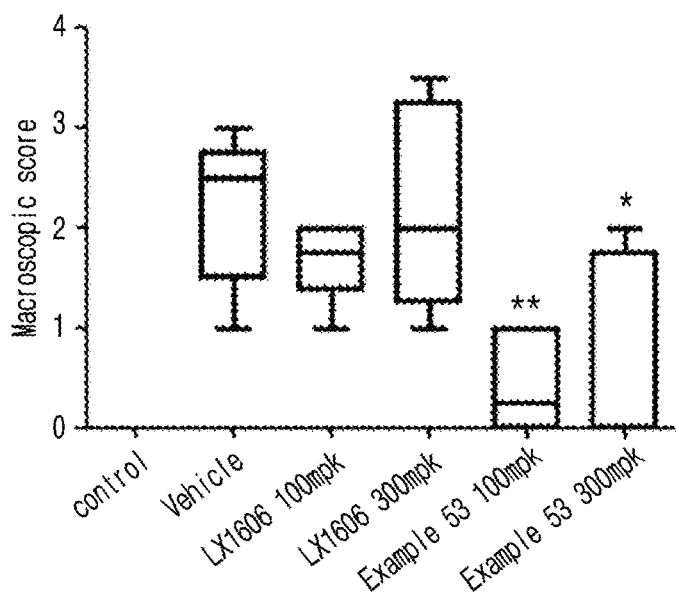
FIG. 3 is a graph showing the macroscopic score for each experimental group. (#: P vs negative control, *: P vs positive control group) *mpk=mg/kg

Disease activity index (DAI) is a composite score of weight loss, fecal consistency, and bloody excretion, which was evaluated using a previously published scoring system. Each score item is shown in table 7 below. The results are shown graphically in FIG. 3.

TABLE 7

| score | weight (%) | fecal consistency | bloody excretion |
| --- | --- | --- | --- |
| 0 | no loss | normal | no |
| 1 | 0-5 | | |
| 2 | 6-10 | loose | |
| 3 | 11-20 | | |
| 4 | >20 | diarrhea | yes |

DAI was measured for all 5 days of DSS treatment and 5 days of recovery. Visual scores were assessed using the scoring system described in the table for DSS colitis.

As shown in table 3, the macroscopic score considering rectal bleeding, hernia, intestinal bleeding and fecal consistency was reduced most significantly in the group treated with the compound of Example 53 at the concentration of 100 mg/kg.

2) Measurement of Colon Permeability

Colon permeability was measured to confirm if the compound of the present invention affected the amelioration of inflammatory bowel disorder. The intestinal epithelial layer acts as a barrier to pathogens and ingested toxins present in the intestinal lumen. The importance of the intestinal epithelial layer was measured by the changes in intercellular permeability and intimate junction function observed in inflammatory bowel disease (IBD) and colorectal cancer. FITC-dextran 4 kDa (10 mg/20 g) was administered 4 hours before sacrifice on the last day, serum was isolated from blood (300-800 mL) and the fluorescence value was measured at ex 485 and em 528. The results are shown in FIG. 4.

Figure 4:
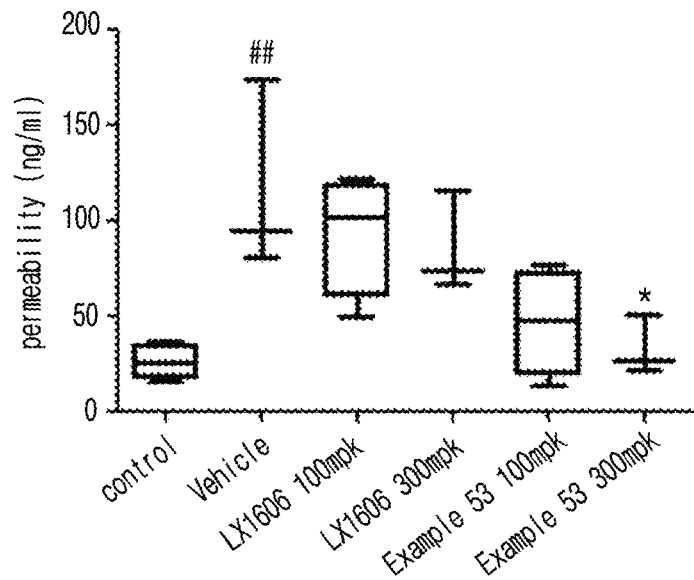
FIG. 4 is a graph showing the colon permeability measured in Experimental Example 3. *mpk=mg/kg
Figure 5A:
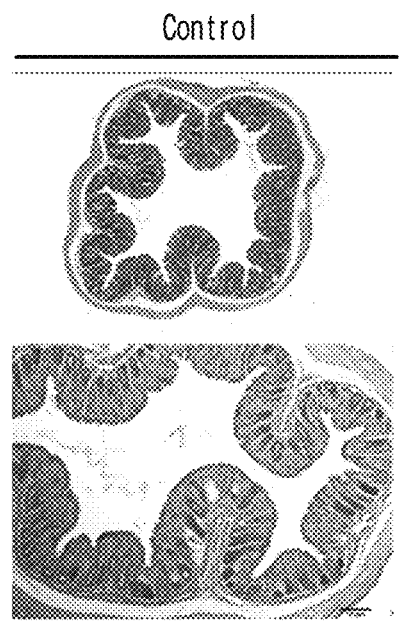
FIG. 5*a*: control group.
Figure 5B:
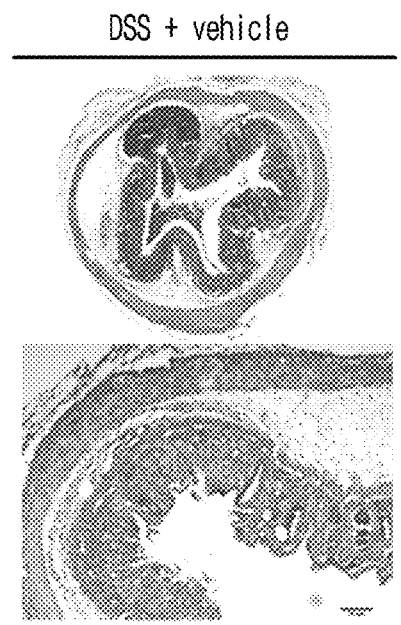
FIG. 5*b*: DSS+vehicle treated group.
Figure 5C:
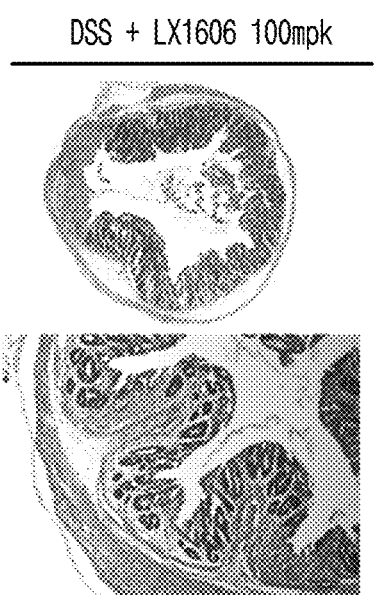
FIG. 5*c*: DSS+LX1606 100 mpk treated group.
Figure 5D:
FIG. 5*d*: DSS+Example 53 compound 100 mpk treated group, *mpk=mg/kg

As shown in FIG. 4, it was confirmed that the permeability was lowered in all the groups treated with the drugs compared to the vehicle treated group. However, lower permeability was observed on average in the group treated with the compound of Example 53 than in the group treated with LX1606.

3) Immunohistochemical Staining (H&E)

Formalin fixed colon sections were embedded in paraffin to evaluate the histological damage and 8-μm sections were stained with hematoxylin and eosin (H & E). After dissolving paraffin of the colon paraffin sample at 60° C., the sample was deparaffinized with xylene, rehydrated with 100/90/80/70% ethanol in that order, and soaked in hematoxylin. The remaining hematoxylin was washed with running water and then the sample was immersed in 0.25% hydrochloric acid/ethanol to completely remove the residual hematoxylin. The tissue sample was washed again with running water, immersed in Scott's tap water, and blued. The tissue sample was fixed in blue so that the purple of hematoxylin did not overlap with the red of eosin. The tissue sample was treated with 90% ethanol and stained with eosin, and soaked in running water and 70/80/90/100% ethanol for dehydration. Finally, xylene was treated for clearing, and then the slides were dried and mounted, followed by tissue microscopy to observe the changes of crypt architecture, cell infiltration, goblet cell depletion and crypt abscess. The results are shown in Table 5.

As shown in FIG. 5, severe epithelial cell damage and crypt damage were observed in the vehicle treated group, whereas, little or no epithelial cell damage and crypt damage were observed in the group treated with 100 mg/kg of the compound of Example 53.

4) Measurement of MPO (Myeloperoxidase) in Large Intestine

For MPO measurement, the colon tissue sample was homogenized in cold 50 mmoL/L potassium phosphate buffer containing 0.5% hexadecyl trimethyl ammonium bromide (pH=6.0) (Sigma). After the homogenate was centrifuged and the supernatant was removed, the absorbance was measured at 450 nm by the addition of a solution containing potassium phosphate buffer, 0-dianisidine and hydrogen peroxide. MPO activity was expressed in units per 1 milligram of the colon tissue. One unit was defined as the amount of enzyme capable of converting one mole of hydrogen peroxide per minute at room temperature. The results are shown in FIG. 6.

Figure 6:
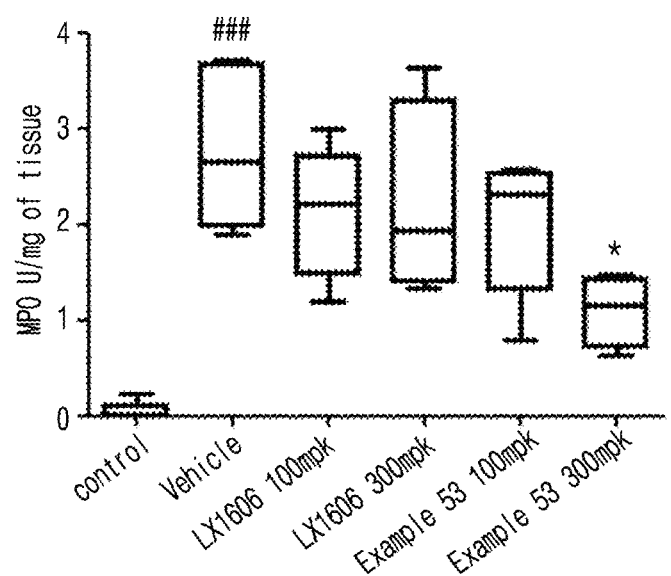
FIG. 6 is a graph showing the MPO activity. *mpk=mg/kg

As shown in FIG. 6, lower MPO activity was measured in the drug-treated group than in the vehicle-treated group. However, the group treated with the compound of Example 53 showed lower MPO activity on average than the group treated with LX1606, in particular, the MPO activity was significantly reduced in the group treated with 300 mg/kg of the compound of Example 53.

From the results of Experimental Example 3, the compound of Example 53 according to the present invention was confirmed to have an excellent therapeutic effect on inflammatory bowel disorder. Therefore, the compound represented by formula 1 according to the present invention can be effectively used for the treatment of inflammatory bowel disorder.

<Manufacturing Example 1> Preparation of Powders

Derivative represented by formula 1 2 g
Lactose 1 g

Powders were prepared by mixing all the above components, which were filled in airtight packs according to the conventional method for preparing powders.

<Manufacturing Example 2> Preparation of Tablets

| | |
|---|---|
| Derivative represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

<Manufacturing Example 3> Preparation of Capsules

| | |
|---|---|
| Derivative represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<Manufacturing Example 4> Preparation of Injectable Solutions

| | |
|---|---|
| Derivative represented by formula 1 | 100 mg |
| Mannitol | 180 mg |
| $Na_2HPO_4 \cdot 2H_2O$ | 26 mg |
| Distilled water | 2974 mg |

Injectable solutions were prepared by incorporating all the above components in the prescribed amounts according to the conventional method for preparing injectable solutions.

<Manufacturing Example 5> Preparation of Health Functional Food

| | |
|---|---|
| Derivative represented by formula 1 | 500 mg |
| Vitamin complex | proper amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health functional food. However, the composition rate can be adjusted. The constituents were mixed according to the conventional method for preparing health functional food and then the composition for health functional food was prepared according to the conventional method.

<Manufacturing Example 6> Preparation of Health Beverages

| | |
|---|---|
| Derivative represented by formula 1 | 500 mg |
| Citric acid | 1000 mg |
| Oligosaccharide | 100 g |
| Maesil (*Prunus mume*) extract | 2 g |
| Taurine | 1 g |
| Purified water | 900 ml |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

The novel tryptophan hydroxylase inhibitor of the present invention can be effectively used for the prevention or treatment of disorders, such as metabolic disorders, cancer, digestive or circulatory system disorders, related to TPH1 activity. In particular, the novel tryptophan hydroxylase inhibitor can be effectively used for the treatment of inflammatory bowel disorder.

What is claimed is:

1. A compound represented by Formula 1 below, an isomer thereof, a solvate thereof, a hydrate thereof or a pharmaceutically acceptable salt thereof:

[Formula 1]

$R^4-L^2-R^3-L^1-R^2-C(=O)-OR^1$ with $R^5$ and $HN-R^6$ substituents wherein,
$R^1$ is hydrogen or $C_{1-10}$ alkyl;
wherein, containing $R^2$ forms

[structures with $R^5$, $HN-R^6$]

[phenyl-CH$_2$-CH($HN-R^6$) structure]

[cyclohexenyl-CH$_2$-CH($HN-R^6$) structure] or

[spiro cyclohexene-pyrrolidine NH structure]

wherein $R^6$ is hydrogen or tert-butoxycarbonyl,
wherein $R^3$ is

[thieno[3,2-d]pyrimidine with $R^{7a}$], [pyrrolo[2,3-d]pyrimidine with $R^{7b}$],

[pyrimidine with $R^{7c}$], [imidazo[1,2-a]pyrazine],

[1,3,4-oxadiazole], [1,2,4-oxadiazole],

[pyrazole], or [pyridine with $R^{7d}$], wherein $R^{7a}$, $R^{7b}$, $R^{7c}$ and $R^{7d}$ are, independently, hydrogen, NH$_2$, or methyl, wherein, when

[$R^2$, $R^5$, $HN-R^6$ structure]

containing $R^2$ is

[phenyl-CH$_2$-CH($HN-R^6$) structure], $R^3$ is

[thieno[3,2-d]pyrimidine with $R^{7a}$], [pyrrolo[2,3-d]pyrimidine with $R^{7b}$] or

[imidazo[1,2-a]pyrazine], wherein, when

[$R^2$, $R^5$, $HN-R^6$ structure]

containing R² is

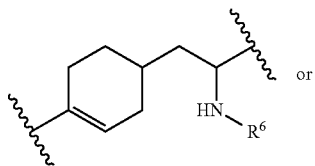 or ,

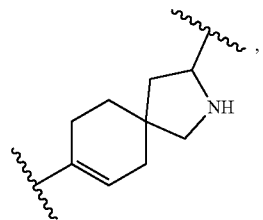

R³ is

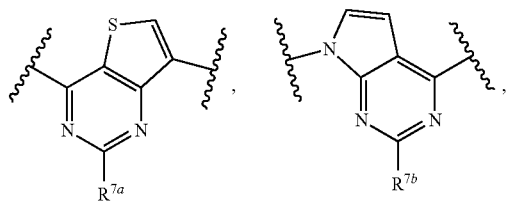

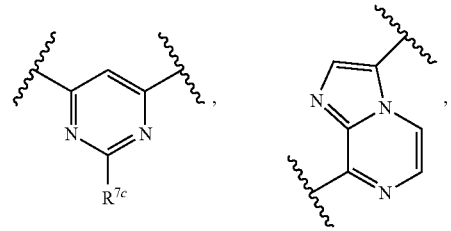

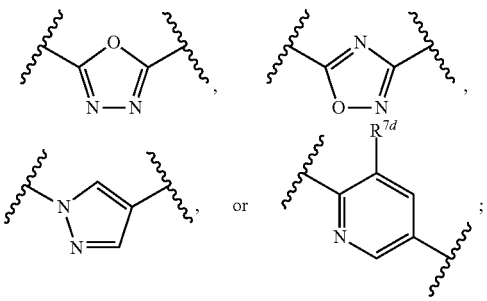 or 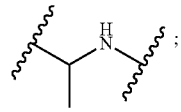 ;

wherein R⁴ is hydrogen, $C_{3-10}$ cycloalkyl, $C_{6-10}$ aryl or 3-10 membered heterocycloalkyl or 5-13 membered heteroaryl; and wherein L¹ and L² are, independently,
 (i) —(CH₂)x-, wherein x is an integer of 0 to 4,
 (ii) —(CH₂)y-O—, wherein y is an integer of 0 to 4,
 (iii) —(CH₂)z-N(Rₐ)—, wherein z is an integer of 0 to 4, and Rₐ is hydrogen or $C_{1-6}$ alkyl),
 (iv) —CH(C(R_b)₃)—O—, wherein R_b is hydrogen or halogen, (v)

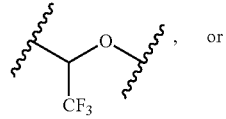 , or (vi)

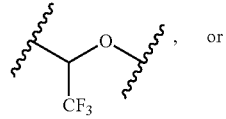 ;

wherein the said alkyl, aryl, cycloalkyl, heterocycloalkyl and heteroaryl are optionally, independently substituted with one or more substituents selected form the group consisting of halogen; NH₂; hydroxy; $C_{1-6}$ alkyl; $C_{1-6}$ alkoxy; $C_{6-10}$ aryl; hydroxyl $C_{1-6}$ alkyl; hydroxyl $C_{1-6}$ alkoxy; hydroxyl $C_{6-10}$ aryl; halo $C_{1-6}$ alkyl; halo $C_{1-6}$ alkyl; halo $C_{1-6}$ alkoxy; halo $C_{6-10}$ aryl; halo $C_{1-6}$ alkyl; halo $C_{1-6}$ alkoxy; halo $C_{6-10}$ aryl; $C_{1-6}$ alkyl $C_{6-10}$ aryl; $C_{1-6}$, alkoxy $C_{6-10}$ aryl; $C_{1-6}$ alkylcarbonyl; $C_{1-6}$ alkoxycarbonyl; halo $C_{3-10}$ cycloalkenyl; halo $C_{1-6}$ alkoxy $C_{6-10}$ aryl; $C_{3-10}$ cycloalkyl $C_{1-6}$ alkoxy $C_{6-10}$ aryl; hydroxyl $C_{1-6}$ alkyl $C_{6-10}$ aryl; 5-13 membered heteroaryl; fused rings containing halophenyl, pyridine and $C_{5-7}$ cycloalkyl; $C_{1-6}$ alkyl 5-13 membered heteroaryl; 3-10 membered heterpcycloalkenyl; and $C_{1-6}$ alkyl 3-10 membered heterocycloalkenyl, and wherein the optional one or more substituents is/are bound to said alkyl, aryl, cycloalkyl, heterocycloalkyl or heteroaryl by single bond(s) or double bond(s);

wherein, the said heteroaryl, heterocycloalkyl and heterocycloalkenyl independently include one or more hetero atoms selected from the group consisting of N, O and S; and wherein the said alkyl or alkoxy is a straight or branched form alkyl or alkoxy.

2. The compound, the isomer thereof, the solvate thereof, the hydrate thereof or the pharmaceutically acceptable salt thereof according to claim 1, wherein:

R¹ is hydrogen or $C_{1-6}$ alkyl;
R⁴ is hydrogen, $C_{6-10}$ aryl or 5-6 membered heterocycloalkyl or 5-6 membered heteroaryl; and
L¹ and L² are, independently,
 (i) —(CH₂)x-, wherein x is 0 or 1,
 (ii) —(CH₂)y-O—, wherein y is 0 or 1,
 (iii) —(CH₂)z-N(Rₐ)—, wherein z is 0 or 1, and Rₐ is hydrogen or $C_{1-6}$ alkyl,
 (iv) —CH(C(R_b)₃)—O—, wherein R_b is hydrogen or halogen, (v)

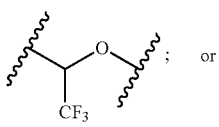 ; or (vi)

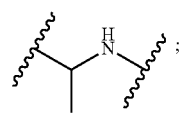 ;

wherein the said alkyl, aryl, arylene cycloalkenylene, heteroarylene, cycloalkyl, heterocycloalkyl and heteroaryl are optionally, independently substituted with one or more substituents selected form the group consisting of halogen; NH₂; hydroxy; $C_{1-4}$ alkyl; $C_{1-4}$ alkoxy; phenyl; hydroxyl $C_{1-4}$ alkyl; hydroxyl $C_{1-4}$ alkoxy; hydroxyphenyl; halo $C_{1-4}$ alkyl; halo $C_{1-4}$ alkoxy; halophenyl; $C_{1-4}$ alkylphenyl; $C_{1-4}$ alkoxyphenyl; $C_{1-4}$ alkylcarbonyl; $C_{1-4}$ alkoxycarbonyl; halo $C_{5-6}$ cycloalkenyl; halo $C_{1-4}$ alkoxyphenyl; $C_{3-6}$ cycloalkyl $C_{1-4}$ alkoxyphenyl; hydroxyl $C_{1-4}$ alkylphenyl; 5-9 membered heteroaryl; fused rings containing halophenyl, pyridine and cycloheptyl; $C_{1-4}$ alkyl 5-9 membered heteroaryl; 5-6 membered heterocycloalkenyl; and $C_{1-6}$ alkyl 5-9 membered heterocycloalkenyl, and the substituent can be bound to alkyl, aryl, arylene cycloalkenylene, heteroarylene, cycloalkyl, heterocycloalkyl or heteroaryl by single bonds or double bonds;

wherein the said heteroaryl, heterocycloalkyl, heterocycloalkenyl and heteroarylene independently include one or more hetero atoms selected from the group consisting of N, O and S; and wherein the said alkyl or alkoxy can have a straight or branched form alkyl or alkoxy.

3. The compound, the isomer thereof, the solvate thereof, the hydrate thereof or the pharmaceutically acceptable salt thereof according to claim 1, wherein:

$R^1$ is hydrogen or $C_{1-5}$ alkyl;

$R^3$ is

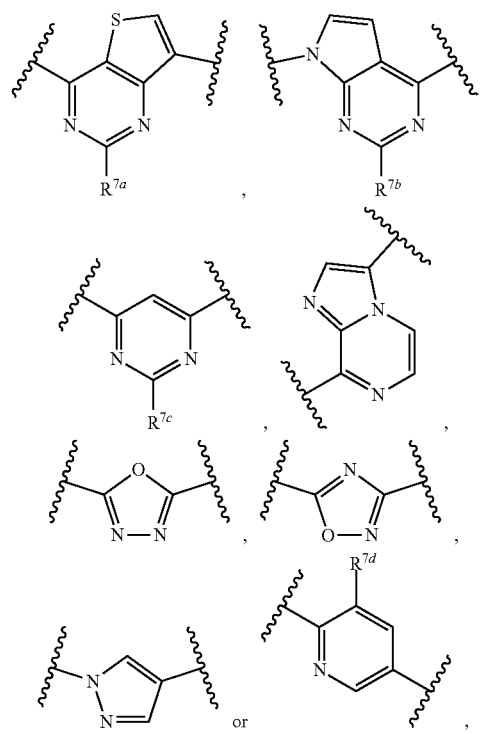

$R^{7a}$a, $R^{7b}$, $R^{7c}$ and $R^{7d}$ are independently hydrogen, $NH_2$ or methyl;

$R^4$ is hydrogen,

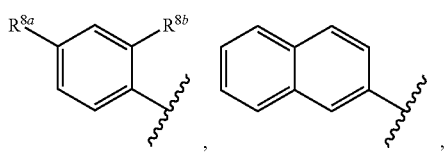

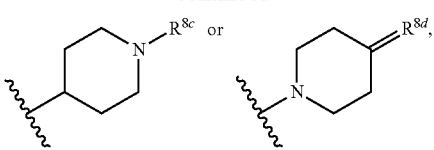

wherein $R^{8a}$ and $R^{8b}$ are, independently, hydrogen, halogen, $C_{1-4}$ alkoxy, phenyl, furan, benzofuran, methyl-substituted pyrazole, dihydropyran, tetramethyldihydropyran, cyclohexenyl, or difluorocyclohexenyl, and the phenyl is optionally substituted with a substituent selected from the group consisting of halogen, hydroxy, $C_{1-4}$ alkoxy, halo $C_{1-4}$ alkoxy, $C_{3-6}$ cycloalkyl $C_{1-4}$ alkoxy and hydroxyl $C_{1-4}$ alkyl, $R^{8c}$ is $C_{1-4}$alkoxycarbonyl, and $R^{8d}$ is

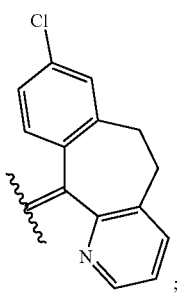

$L^1$ and $L^2$ are, independently, (i)

(ii)

(iii)

(iv)

(v)

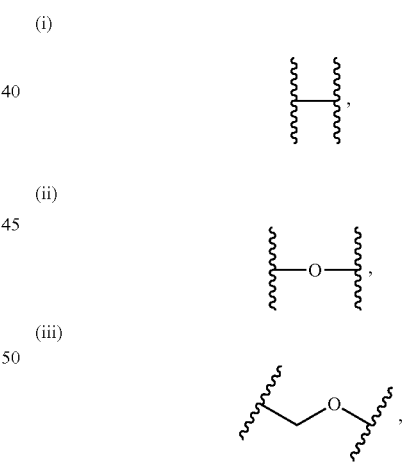

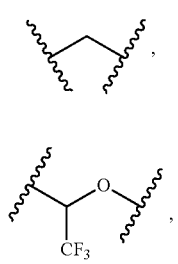

-continued (vi) 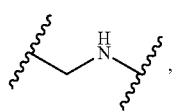, (vii) 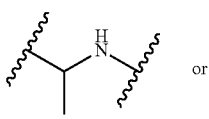 or (viii) 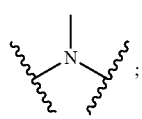;

and the said alkyl or alkoxy can have a straight or branched form alkyl or alkoxy.

4. The compound, the isomer thereof, the solvate thereof, the hydrate thereof or the pharmaceutically acceptable salt thereof according to claim 1, wherein $R^1$ is hydrogen, methyl, ethyl, n-butyl, t-butyl, i-butyl, n-pentyl, t-pentyl, i-pentyl or neo-pentyl.

5. The compound, the isomer thereof, the solvate thereof, the hydrate thereof or the pharmaceutically acceptable salt thereof according to claim 1, wherein, when

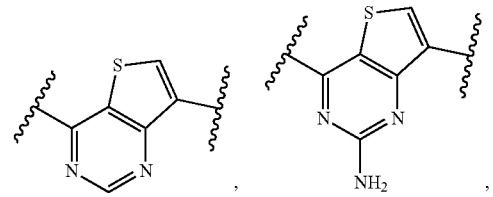

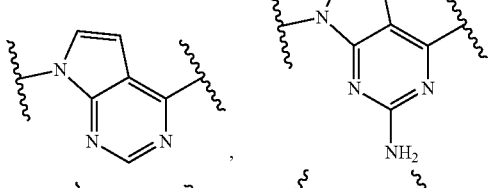

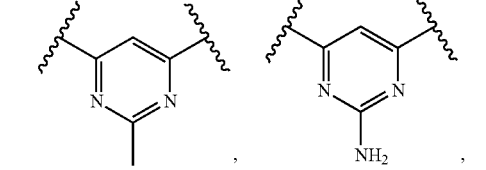

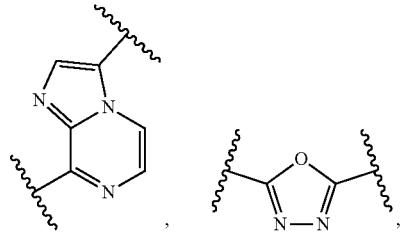

-continued

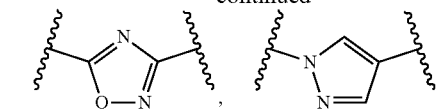

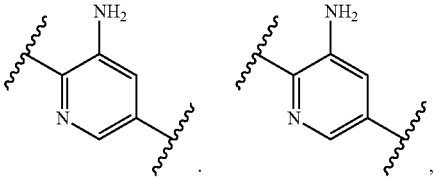, When

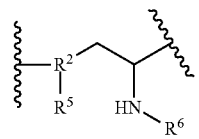 is

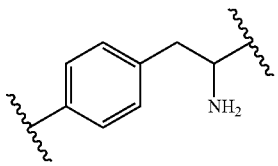, $R^3$ is

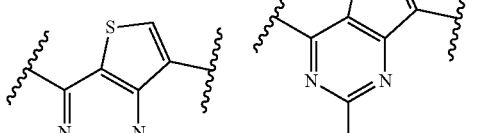,

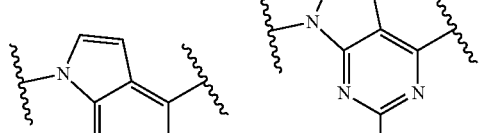,

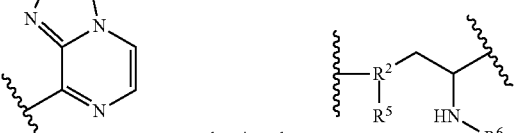, wherein, when is

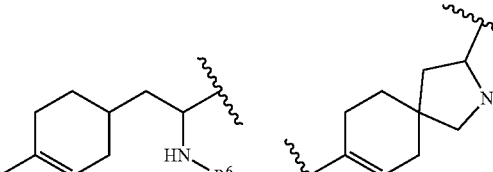

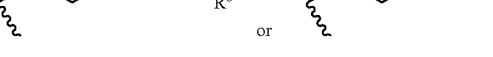

R³ is
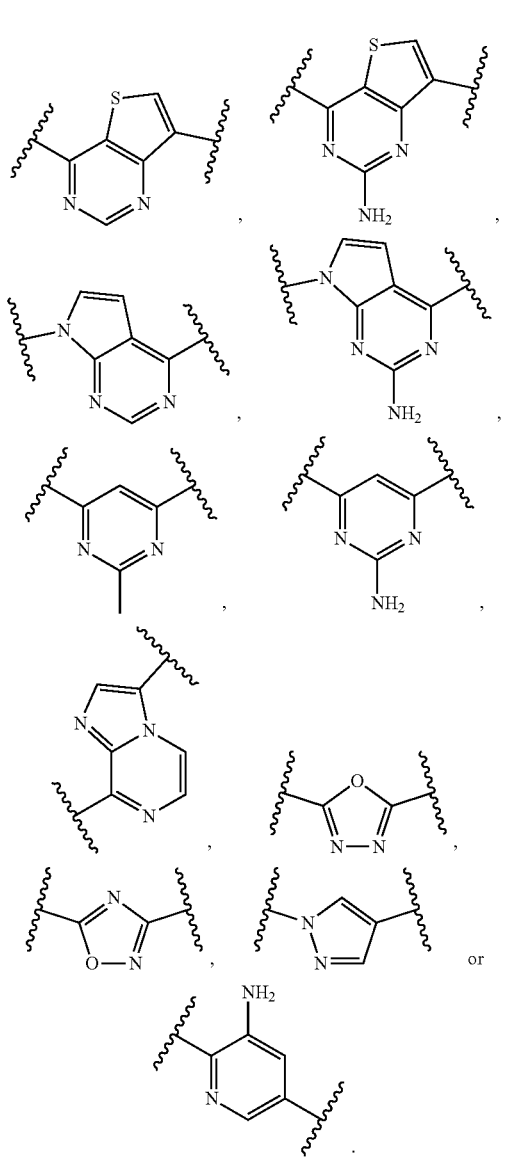
6. The compound, the isomer thereof, the solvate thereof, the hydrate thereof or the pharmaceutically acceptable salt thereof according to claim 1, wherein:
R⁴ is hydrogen,
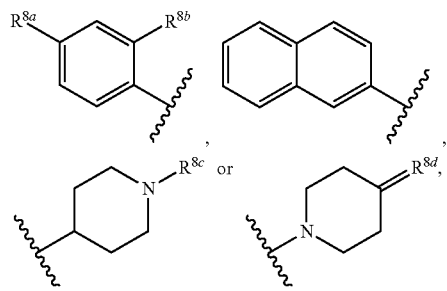
at this time, $R^{8a}$ is hydrogen, halogen, $C_{1-4}$ alkoxy,
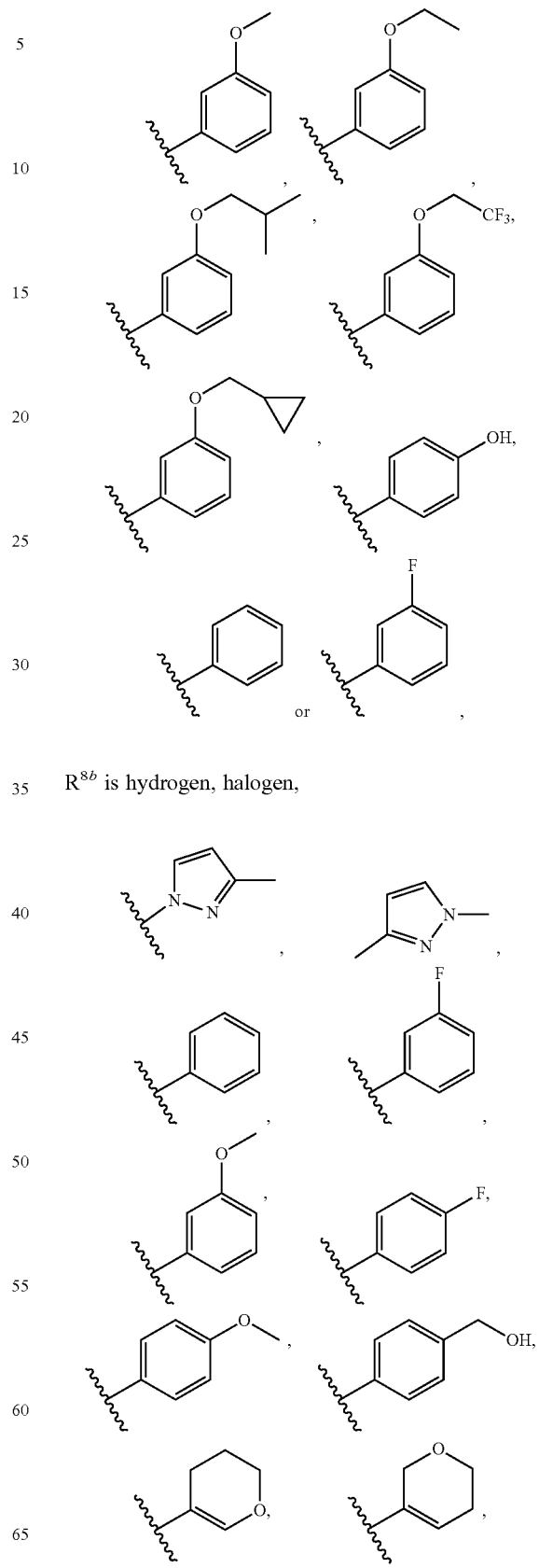
$R^{8b}$ is hydrogen, halogen, -continued

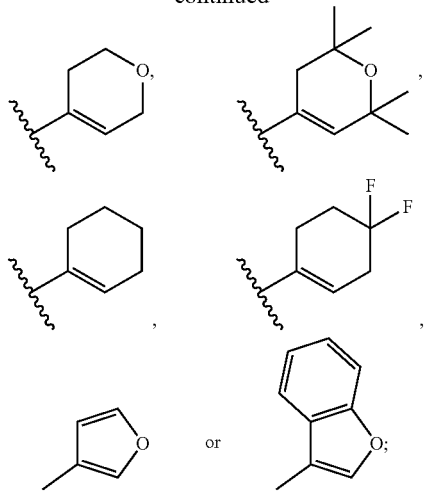

$R^{8c}$ is isopropoxycarbonyl, and
$R^{8d}$ is

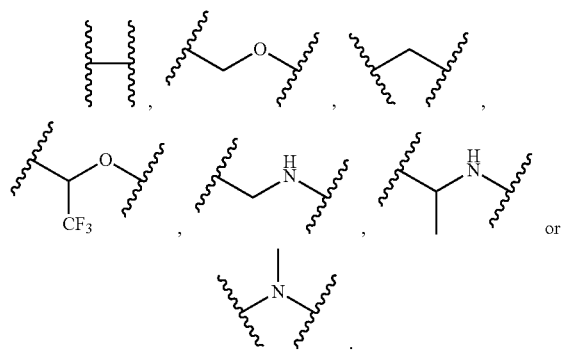

7. The compound, the isomer thereof, the solvate thereof, the hydrate thereof or the pharmaceutically acceptable salt thereof according to claim 1, wherein:
  $L^1$ is

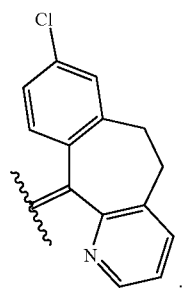 [SMILES: *=C1c2ccc(Cl)cc2CCc2cccnc21]

and
  $L^2$ is

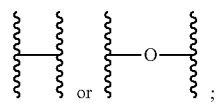

8. The compound, the isomer thereof, the solvate thereof, the hydrate thereof or the pharmaceutically acceptable salt thereof according to claim 1, wherein:
  $R^4$ is hydrogen,

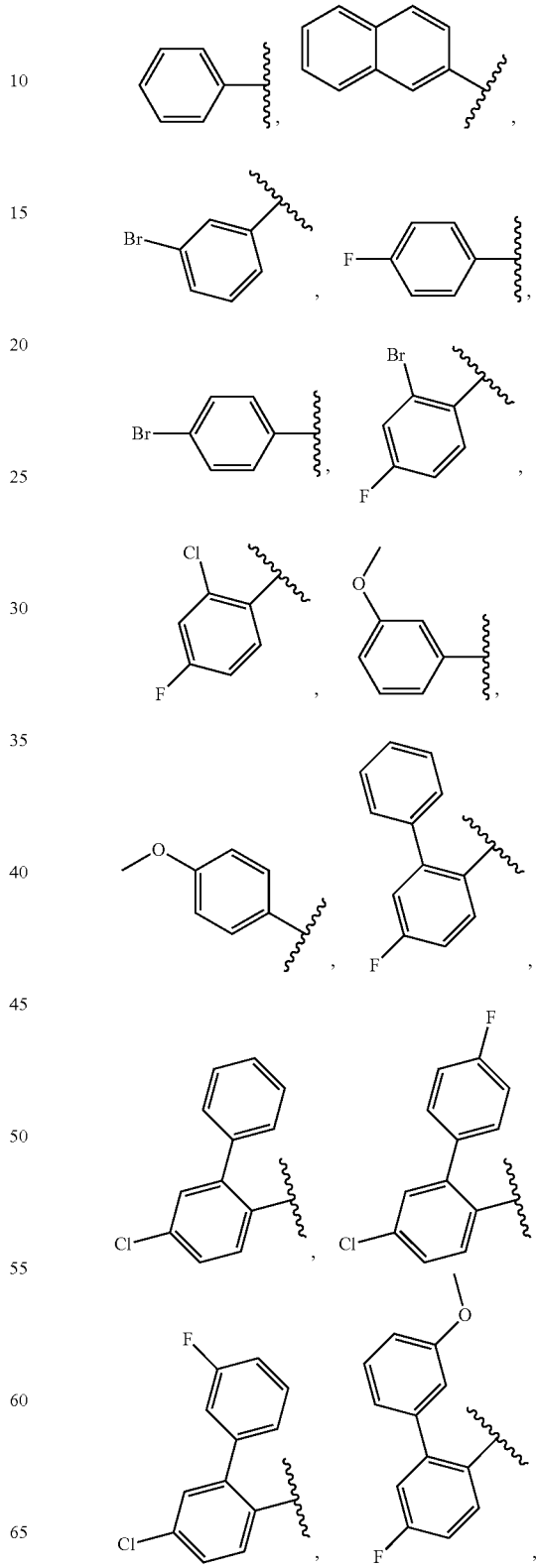

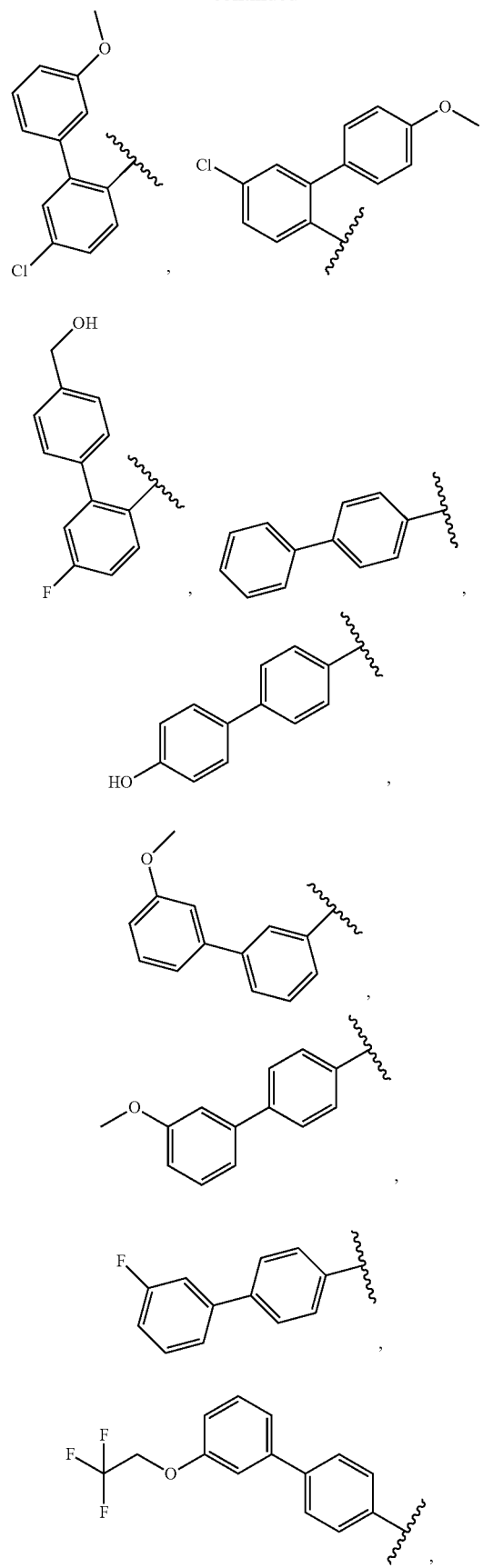
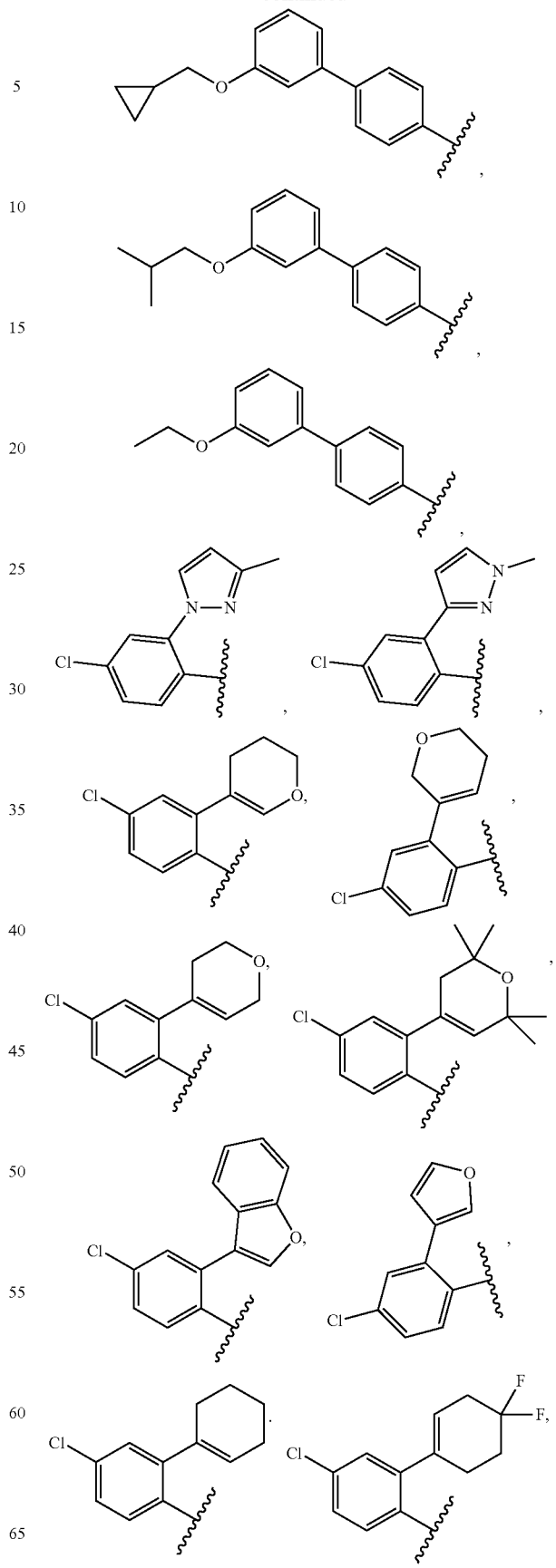

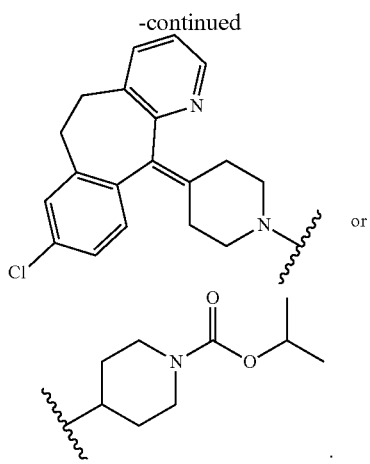

9. The compound, the isomer thereof, the solvate thereof, the hydrate thereof or the pharmaceutically acceptable salt thereof according to claim 1, wherein the compound represented by formula 1 is selected from the group consisting of the following compounds:

<1> (S)-2-amino-3-(4-((7-((5-fluoro-[1,1'-biphenyl]-2-yl)methyl)-7H-pyrrolo[2,3-d]pyrimidine-4-yl)oxy)phenyl)propionic acid hydrochloride;

<2> (S)-2-amino-3-(4-((7-3-bromobenzyl)-7H-pyrrolo[2,3-d]pyrimidine-4-yl)oxy)phenyl)propionic acid hydrochloride;

<3> (S)-2-amino-3-(4-((2-amino-7-(2-bromo-4-fluorobenzyl)-7H-pyrrolo[2,3-d]pyrimidine-4-yl)oxy)phenyl)propionic acid hydrochloride;

<4> (S)-2-amino-3-(4-((2-amino-7-((5-fluoro-3'-methoxy-[1,1'-biphenyl]-2-yl)methyl)-7H-pyrrolo[2,3-d]pyrimidine-4-yl)oxy)phenyl)propionic acid hydrochloride;

<5> (S)-2-amino-3-(4-((2-amino-7-((5-fluoro-4'-(hydroxymethyl)-[1,1'-biphenyl]-2-yl)methyl)-7H-pyrrolo[2,3-d]pyrimidine-4-yl)oxy)phenyl)propionic acid hydrochloride;

<6> (S)-2-amino-3-(4-((2-amino-7-(2-chloro-4-fluorobenzyl)-7H-pyrrolo[2,3-d]pyrimidine-4-yl)oxy)phenyl)propionic acid hydrochloride;

<7> (S)-2-amino-3-(4-((7-((3'-methoxy-[1,1'-biphenyl]-3-yl)methyl)-7H-pyrrolo[2,3-d]pyrimidine-4-yl)oxy)phenyl)propionic acid hydrochloride;

<8> (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride;

<9> (2S)-2-amino-3-(4-(4-(2,2,2-trifluoro-1-(3'-fluoro-[1,1'-biphenyl]-4-yl)ethoxy)thieno[3,2-d]pyrimidine-7-yl)phenyl)propionic acid hydrochloride;

<10> (2S)-2-amino-3-(4-(4-(2,2,2-trifluoro-1-(3'-methoxy-[1,1'-biphenyl]-4-yl)ethoxy)thieno[3,2-d]pyrimidine-7-yl)phenyl)propionic acid hydrochloride;

<11> (S)-2-amino-3-(4-(2-amino-7-(4-bromobenzyl)-7H-pyrrolo[2,3-d]pyrimidine-4-yl)phenyl)propionic acid hydrochloride;

<12> (S)-2-amino-3-(4-(2-amino-7-((3'-methoxy-[1,1'-biphenyl]-4-yl)methyl)-7H-pyrrolo[2,3-d]pyrimidine-4-yl)phenyl)propionic acid hydrochloride;

<13> (S)-2-amino-3-(4-(4-((5-chloro-3'-methoxy-[1,1'-biphenyl]-2-yl)methoxy)thieno[3,2-d]pyrimidine-7-yl)phenyl)propionic acid hydrochloride;

<14> (S)-2-amino-3-(4-(4-((5-chloro-[1,1'-biphenyl]-2-yl)methoxy)thieno[3,2-d]pyrimidine-7-yl)phenyl)propionic acid hydrochloride;

<15> (S)-2-amino-3-(4-(4-((5-chloro-3'-fluoro-[1,1'-biphenyl]-2-yl)methoxy)thieno[3,2-d]pyrimidine-7-yl)phenyl)propionic acid hydrochloride;

<16> (S)-2-amino-3-(4-(4-(benzyloxy)thieno[3,2-d]pyrimidine-7-yl)phenyl)propionic acid hydrochloride;

<17> (S)-2-amino-3-(4-(4-((3'-methoxy-[1,1'-biphenyl]-4-yl)methoxy)thieno[3,2-d]pyrimidine-7-yl)phenyl)propionic acid hydrochloride;

<18> (S)-3-(4-(4-(([1,1'-biphenyl]-4-ylmethyl)amino)thieno[3,2-d]pyrimidine-7-yl)phenyl)-2-aminopropionic acid hydrochloride;

<19> (S)-2-amino-3-(4-(4-(((R)-1-(naphthalene-2-yl)ethyl)amino)thieno[3,2-d]pyrimidine-7-yl)phenyl)propionic acid hydrochloride;

<20> (S)-2-amino-3-(4-(4-((1-(isopropoxycarbonyl)piperidine-4-yl)(methyl)amino)thieno[3,2-d]pyrimidine-7-yl)phenyl)propionic acid hydrochloride;

<21> (S)-2-amino-3-(4-(2-amino-7H-pyrrolo[2,3-d]pyrimidine-4-yl)phenyl)propionic acid;

<22> ethyl (S)-2-amino-3-(4-(4-((R)-1-(4-chloro-2-(3-methyl-1H-pyrazole-1-yl)phenyl)-2,2,2-trifluoroethoxy)thieno[3,2d]pyrimidine-7-yl)phenyl)propionate hydrochloride;

<23> (S)-2-amino-3-(4-(7-((3'-methoxy-[1,1'-biphenyl]-4-yl)methyl)-7H-pyrrolo[2,3-d]pyrimidine-4-yl)phenyl)propionic acid hydrochloride;

<24> (S)-2-amino-3-(4-(4-((R)-1-(5-chloro-3'-fluoro-[1,1'-biphenyl]-2-yl)-2,2,2-trifluoroethoxy)thieno[3,2-d]pyrimidine-7-yl)phenyl)propionic acid hydrochloride;

<25> (2S)-2-amino-3-(4-(4-(1-(5-chloro-3'-methoxy-[1,1'-biphenyl]-2-yl)-2,2,2-trifluoroethoxy)thieno[3,2-d]pyrimidine-7-yl)phenyl)propionic acid hydrochloride;

<26> (2S)-2-amino-3-(4-(4-(1-(5-chloro-[1,1'-biphenyl]-2-yl)-2,2,2-trifluoroethoxy)thieno[3,2-d]pyrimidine-7-yl)phenyl)propionic acid hydrochloride;

<27> (S)-2-amino-3-(4-(4-((R)-2,2,2-trifluoro-1-(3'-methoxy-[1,1'-biphenyl]-4-yl)ethoxy)thieno[3,2-d]pyrimidine-7-yl)phenyl)propionic acid hydrochloride;

<28> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate;

<29> ethyl (S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)phenyl)propionate hippurate;

<30> (2S)-2-amino-3-(4-(4-((R)-1-(4-chloro-2-(3-methyl-1H-pyrazole-1-yl)phenyl)-2,2,2-trifluoroethoxy)thieno[3,2-d]pyrimidine-7-yl)cyclohex-3-ene-1-yl)propionic acid hydrochloride;

<31> (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;

<32> (2S)-2-amino-3-(4-(6-((R)-1-(4-chloro-2-(3-methyl-1H-pyrazole-1-yl)phenyl)-2,2,2-trifluoroethoxy)-2-methylpyrimidine-4-yl)cyclohex-3-ene-1-yl)propionic acid hydrochloride;

<33> (2S)-2-amino-3-(4-(7-((3'-methoxy-[1,1'-biphenyl]-4-yl)methyl)-7H-pyrrolo[2,3-d]pyrimidine-4-yl)cyclohex-3-ene-1-yl)propionic acid hydrochloride;

<34> (2S)-2-amino-3-(4-(2-amino-6-((R)-2,2,2-trifluoro-1-(3'-methoxy-[1,1'-biphenyl]-4-yl)ethoxy)pyrimidine-4-yl)cyclohex-3-ene-1-yl)propionic acid hydrochloride;

<35> (2S)-2-amino-3-(4-(4-((R)-2,2,2-trifluoro-1-(3'-methoxy-[1,1'-biphenyl]-4-yl)ethoxy)thieno[3,2-d]pyrimidin-7-yl)cyclohex-3-en-1-yl)propionic acid hydrochloride;

<36> ethyl (2S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)propionate;

<37> (S)-2-amino-3-(4-(5-(4-methoxyphenyl)-1,2,4-oxadiazol-3-yl)phenyl)propionic acid hydrochloride;

<38> (S)-2-amino-3-(4-(5-phenyl-1,2,4-oxadiazol-3-yl)phenyl)propionic acid hydrochloride;

<39> (S)-2-amino-3-(4-(5-(4-fluorophenyl)-1,2,4-oxadiazol-3-yl)phenyl)propionic acid hydrochloride;

<40> (S)-2-amino-3-(4-(5-(4-bromophenyl)-1,3,4-oxadiazol-2-yl)phenyl)propionic acid hydrochloride;

<41> (S)-2-amino-3-(4-(5-phenyl-1,3,4-oxadiazol-2-yl)phenyl)propionic acid hydrochloride;

<42> (S)-3-(4-(5-([1,1'-biphenyl]-4-yl)-1,3,4-oxadiazol-2-yl)phenyl)-2-aminopropionic acid hydrochloride;

<43> (S)-2-amino-3-(4-(5-(4'-hydroxy-[1,1'-biphenyl]-4-yl)-1,3,4-oxadiazol-2-yl)phenyl)propionic acid hydrochloride;

<44> (2S)-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)-2-((tert-butoxycarbonyl)amino)propionic acid;

<45> (2S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)propionic acid;

<46> (2S)-2-amino-3-(4-(4-(1-(5-chloro-4'-fluoro-[1,1'-biphenyl]-2-yl)-2,2,2-trifluoroethoxy)thieno[3,2-d]pyrimidin-7-yl)phenyl)propionic acid hydrochloride;

<47> (2S)-2-amino-3-(4-(2-amino-6-(1-(5-chloro-4'-fluoro-[1,1'-biphenyl]-2-yl)-2,2,2-trifluoroethoxy)pyrimidin-4-yl)cyclohex-3-en-1-yl)propionic acid hydrochloride;

<48> (2S)-2-amino-3-(4-(2-amino-6-(1-(5-chloro-[1,1'-biphenyl]-2-yl)-2,2,2-trifluoroethoxy)pyrimidin-4-yl)cyclohex-3-en-1-yl)propionic acid hydrochloride;

<49> (2S)-2-amino-3-(4-(1-((3'-methoxy-[1,1'-biphenyl]-4-yl)methyl)-1H-pyrazol-4-yl)cyclohex-3-en-1-yl)propionic acid hydrochloride;

<50> (2S)-2-amino-3-(4-(4-(1-(5-chloro-4'-fluoro-[1,1'-biphenyl]-2-yl)-2,2,2-trifluoroethoxy)thieno[3,2-d]pyrimidin-7-yl)cyclohex-3-en-1-yl)propionic acid hydrochloride;

<51> (2S)-2-amino-3-(4-(4-(1-(5-chloro-[1,1'-biphenyl]-2-yl)-2,2,2-trifluoroethoxy)thieno[3,2-d]pyrimidin-7-yl)cyclohex-3-en-1-yl)propionic acid hydrochloride;

<52> (2S)-2-amino-3-(4-(2-amino-6-(4-(8-chloro-5,6-dihydro-11H-benzo[5,6]cyclohepta[1,2-b]pyridin-11-ylidene)piperidin-1-yl)pyrimidin-4-yl)cyclohex-3-en-1-yl)propionic acid dihydrochloride;

<53> ethyl (2S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)propionate hippurate;

<54> (2S)-2-amino-3-(4-(5-amino-6-((R)-1-(4-chloro-2-(3-methyl-1H-pyrazol-1-yl)phenyl)-2,2,2-trifluoroethoxy)pyridin-3-yl)cyclohex-3-en-1-yl)propionic acid dihydrochloride;

<55> (2S)-2-amino-3-(4-(8-((R)-1-(4-chloro-2-(3-methyl-1H-pyrazol-1-yl)phenyl)-2,2,2-trifluoroethoxy)imidazo[1,2-a]pyrazin-3-yl)cyclohex-3-en-1-yl)propionic acid hydrochloride;

<56> (S)-2-amino-3-(4-(8-((R)-1-(4-chloro-2-(3-methyl-1H-pyrazol-1-yl)phenyl)-2,2,2-trifluoroethoxy)imidazo[1,2-a]pyrazin-3-yl)phenyl)propionic acid hydrochloride;

<57> (2S)-2-amino-3-(4-(4-((R)-1-(4-chloro-2-(3-methyl-1H-pyrazol-1-yl)phenyl)-2,2,2-trifluoroethoxy)thieno[3,2-d]pyrimidin-7-yl)cyclohex-3-en-1-yl)propionic acid;

<58> (2S)-2-amino-3-(4-(2-amino-6-((R)-2,2,2-trifluoro-1-(3'-methoxy-[1,1'-biphenyl]-4-yl)ethoxy)pyrimidin-4-yl)cyclohex-3-en-1-yl)propionic acid;

<59> methyl (2S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)propionate hippurate;

<60> (2S)-2-amino-3-(4-(2-amino-6-((R)-2,2,2-trifluoro-1-(3'-(2,2,2-trifluoroethoxy)-[1,1'-biphenyl]-4-yl)ethoxy)pyrimidin-4-yl)cyclohex-3-en-1-yl)propionic acid hydrochloride;

<61> (2S)-2-amino-3-(4-(2-amino-6-((R)-1-(3'-(cyclopropylmethoxy)-[1,1'-biphenyl]-4-yl)-2,2,2-trifluoroethoxy)pyrimidin-4-yl)cyclohex-3-en-1-yl)propionic acid hydrochloride;

<62> (2S)-2-amino-3-(4-(2-amino-6-((R)-2,2,2-trifluoro-1-(3'-쇼butoxy-[1,1'-biphenyl]-4-yl)ethoxy)pyrimidin-4-yl)cyclohex-3-en-1-yl)propionic acid hydrochloride;

<63> (2S)-2-amino-3-(4-(2-amino-6-((R)-1-(3'-ethoxy-[1,1'-biphenyl]-4-yl)-2,2,2-trifluoroethoxy)pyrimidin-4-yl)cyclohex-3-en-1-yl)propionic acid hydrochloride;

<64> (2S)-2-amino-3-(4-(2-amino-6-((R)-1-(4-chloro-2-(1-methyl-1H-pyrazol-3-yl)phenyl)-2,2,2-trifluoroethoxy)pyrimidin-4-yl)cyclohex-3-en-1-yl)propionic acid hydrochloride;

<65> ethyl (2S)-3-(4-(2-amino-6-((R)-1-(4-chloro-2-(3-methyl-1H-pyrazol-1-yl)phenyl)-2,2,2-trifluoroethoxy)pyrimidin-4-yl)cyclohex-3-en-1-yl)-2-((tert-butoxycarbonyl)amino)propionate;

<66> (2S)-2-amino-3-(4-(2-amino-6-((R)-1-(4-chloro-2-(5,6-dihydro-2H-pyran-3-yl)phenyl)-2,2,2-trifluoroethoxy)pyrimidin-4-yl)cyclohex-3-en-1-yl)propionic acid hydrochloride;

<67> (2S)-2-amino-3-(4-(2-amino-6-((R)-1-(4-chloro-2-(5,6-dihydro-2H-pyran-3-yl)phenyl)-2,2,2-trifluoroethoxy)pyrimidin-4-yl)cyclohex-3-en-1-yl)propionic acid;

<68> (2S)-2-amino-3-(4-(2-amino-6-((R)-1-(4-chloro-2-(1-methyl-1H-pyrazol-3-yl)phenyl)-2,2,2-trifluoroethoxy)pyrimidin-4-yl)cyclohex-3-en-1-yl)propionic acid;

<69> (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidin-7-yl)phenyl)propionic acid hydrochloride;

<70> (S)-2-amino-3-(4-(4-((R)-1-(4-chloro-2-(5,6-dihydro-2H-pyran-3-yl)phenyl)-2,2,2-trifluoroethoxy)thieno[3,2-d]pyrimidin-7-yl)phenyl)propionic acid;

<71> (2S)-2-amino-3-(4-(2-amino-6-((R)-1-(2-(benzofuran-3-yl)-4-chlorophenyl)-2,2,2-trifluoroethoxy)pyrimidin-4-yl)cyclohex-3-en-1-yl)propionic acid hydrochloride;

<72> (S)-2-amino-3-(4-(4-((R)-1-(2-(benzofuran-3-yl)-4-chlorophenyl)-2,2,2-trifluoroethoxy)thieno[3,2-d]pyrimidin-7-yl)phenyl)propionic acid hydrochloride;

<73> (S)-2-amino-3-(4-(4-((R)-1-(4-chloro-2-(furan-3-yl)phenyl)-2,2,2-trifluoroethoxy)thieno[3,2-d]pyrimidine-7-yl)phenyl)propionic acid hydrochloride;
<74> (2S)-2-amino-3-(4-(2-amino-6-((R)-1-(4-chloro-2-(furan-3-yl)phenyl)-2,2,2-trifluoroethoxy)pyrimidine-4-yl)cyclohex-3-ene-1-yl)propionic acid hydrochloride;
<75> (2S)-2-amino-3-(4-(2-amino-6-((R)-1-(5-chloro-4',4'difluoro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride;
<76> (2S)-2-amino-3-(4-(2-amino-6-((R)-1-(5-chloro-4'-methoxy-[1,1'-biphenyl]-2-yl)-2,2,2-trifluoroethoxy)pyrimidine-4-yl)cyclohex-3-ene-1-yl)propionic acid hydrochloride;
<77> (2S)-2-amino-3-(4-(2-amino-6-((R)-1-(4-chloro-2-(2,2,6,6-tetramethyl-3,6-dihydro-2H-pyran-4-yl)phenyl)-2,2,2-trifluoroethoxy)pyrimidine-4-yl)cyclohex-3-ene-1-yl)propionic acid hydrochloride;
<78> (S)-2-amino-3-(4-(4-((R)-1-(4-chloro-2-(2,2,6,6-tetramethyl-3,6-dihydro-2H-pyran-4-yl)phenyl)-2,2,2-trifluoroethoxy)thieno[3,2-d]pyrimidine-7-yl)phenyl)propionic acid hydrochloride;
<79> 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;
<80> 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid;
<81> (S)-2-amino-3-(4-(4-((R)-1-(4-chloro-2-(3,6-dihydro-2H-pyran-4-yl)phenyl)-2,2,2-trifluoroethoxy)thieno[3,2-d]pyrimidine-7-yl)phenyl)propionic acid hydrochloride;
<82> (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid hydrochloride;
<83> 8-(2-amino-6-((R)-1-(4-chloro-2-(3,6-dihydro-2H-pyran-4-yl)phenyl)-2,2,2-trifluoroethoxy)pyrimidine-4-yl)-2-azaspiro[4.5]dec-7-ene-3-carboxylic acid hydrochloride;
<84> 8-(4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride;
<85> (2S)-2-amino-3-(4-(2-amino-6-((R)-1-(4-chloro-2-(3,6-dihydro-2H-pyran-4-yl)phenyl)-2,2,2-trifluoroethoxy)pyrimidine-4-yl)cyclohex-3-ene-1-yl)propionic acid;
<86> ethyl (2S)-2-amino-3-(4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl) propionate hippurate;
<87> 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid hydrochloride;
<88> 8-(2-amino-6-((R)-2,2,2-trifluoro-1-(3'-fluoro-[1,1'-biphenyl]-4-yl)ethoxy)pyrimidine-4-yl)-2-azaspiro[4.5]dec-7-ene-3-carboxylic acid hydrochloride;
<89> 8-(2-amino-6-((R)-2,2,2-trifluoro-1-(3'-methoxy-[1,1'-biphenyl]-4-yl)ethoxy)pyrimidine-4-yl)-2-azaspiro[4.5]dec-7-ene-3-carboxylic acid;
<90> (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid hydrochloride;
<91> (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl)propionic acid hydrochloride;
<92> (2S)-2-amino-3-(4-(2-amino-6-((R)-2,2,2-trifluoro-1-(3'-fluoro-[1,1'-biphenyl]-4-yl)ethoxy)pyrimidine-4-yl)cyclohex-3-ene-1-yl)propionic acid;
<93> 8-(4-((R)-1-(4-chloro-2-(5,6-dihydro-2H-pyran-3-yl)phenyl)-2,2,2-trifluoroethoxy)thieno[3,2-d]pyrimidine-7-yl)-2-azaspiro[4.5]dec-7-ene-3-carboxylic acid hydrochloride;
<94> 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;
<95> 8-(2-amino-6-((R)-2,2,2-trifluoro-1-(3'-fluoro-[1,1'-biphenyl]-4-yl)ethoxy)pyrimidine-4-yl)-2-azaspiro[4.5]dec-7-ene-3-carboxylic acid;
<96> neopentyl (2S)-2-amino-3-(4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionate hippurate;
<97> (2S)-2-amino-3-(4-(2-amino-6-((R)-1-(4-chloro-2-(3,4-dihydro-2H-pyran-5-yl)phenyl)-2,2,2-trifluoroethoxy)pyrimidine-4-yl)cyclohex-3-ene-1-yl)propionic acid hydrochloride;
<98> (2S)-2-amino-3-(4-(2-amino-6-((R)-1-(5-chloro-2',3',4',5'-tetrahydro-[1,1'-biphenyl]-2-yl)-2,2,2-trifluoroethoxy)pyrimidine-4-yl)cyclohex-3-ene-1-yl)propionic acid hydrochloride;
<99> (S)-2-amino-3-((R)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;
<100> (S)-2-amino-3-((S)-4-(2-amino-6-((R)-1-(4-chloro-2-(3-methyl-1H-pyrazole-1-yl)phenyl)-2,2,2-trifluoroethoxy)pyrimidine-4-yl)cyclohex-3-ene-1-yl)propionic acid hydrochloride;
<101> (S)-2-amino-3-((R)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride;
<102> (S)-2-amino-3-((S)-4-(2-amino-6-((R)-1-(4-chloro-2-(5,6-dihydro-2H-pyran-3-yl)phenyl)-2,2,2-trifluoroethoxy)pyrimidine-4-yl)cyclohex-3-ene-1-yl)propionic acid hydrochloride;
<103> (S)-2-amino-3-(4-(4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride;
<104> (S)-2-amino-3-(4-(4-((R)-1-(5-chloro-2',3',4',5'-tetrahydro-[1,1'-biphenyl]-2-yl)-2,2,2-trifluoroethoxy)thieno[3,2-d]pyrimidine-7-yl)phenyl)propionic acid hydrochloride;
<105> (S)-2-amino-3-(4-(2-amino-4-((R)-1-(4-chloro-2-(5,6-dihydro-2H-pyran-3-yl)phenyl)-2,2,2-trifluoroethoxy)thieno[3,2-d]pyrimidine-7-yl)phenyl)propionic acid hydrochloride;
<106> (S)-2-amino-3-(4-(2-amino-4-((R)-1-(4-chloro-2-(3,4-dihydro-2H-pyran-5-yl)phenyl)-2,2,2-trifluoroethoxy)thieno[3,2-d]pyrimidine-7-yl)phenyl)propionic acid hydrochloride;
<107> 8-(2-amino-4-((R)-1-(4-chloro-2-(3-methyl-1H-pyrazole-1-yl)phenyl)-2,2,2-trifluoroethoxy)thieno[3,2-d]pyrimidine-7-yl)-2-azaspiro[4.5]dec-7-ene-3-carboxylic acid hydrochloride;

<108> 8-(2-amino-6-((R)-1-(4-chloro-2-(3,4-dihydro-2H-pyran-5-yl)phenyl)-2,2,2-trifluoroethoxy)pyrimidine-4-yl)-2-azaspiro[4.5]dec-7-ene-3-carboxylic acid hydrochloride;

<109> 8-(2-amino-6-((R)-1-(5-chloro-2',3',4',5'-tetrahydro-[1,1'-biphenyl]-2-yl)-2,2,2-trifluoroethoxy)pyrimidine-4-yl)-2-azaspiro[4.5]dec-7-ene-3-carboxylic acid hydrochloride;

<110> (3 S,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<111> (3 S,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<112> (3R,5R)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<113> (3R,5S)-8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylic acid hydrochloride;

<114> (3 S,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;

<115> (3 S,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;

<116> (3R,5R)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;

<117> (3R,5S)-8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylic acid hydrochloride;

<118> ethyl 8-(2-amino-6-((R)-1-(4-chloro-2-(5,6-dihydro-2H-pyran-3-yl)phenyl)-2,2,2-trifluoroethoxy)pyrimidine-4-yl)-2-azaspiro[4.5]dec-7-ene-3-carboxylate hippurate;

<119> ethyl 8-(2-amino-6-((R)-1-(4-chloro-2-(3-methyl-1H-pyrazole-1-yl)phenyl)-2,2,2-trifluoroethoxy)pyrimidine-4-yl)-2-azaspiro[4.5]dec-7-ene-3-carboxylate hippurate;

<120> ethyl (S)-2-amino-3-(4-(2-amino-4-((R)-1-(4-chloro-2-(3-methyl-1H-pyrazole-1-yl)phenyl)-2,2,2-trifluoroethoxy)thieno[3,2-d]pyrimidine-7-yl)phenyl) propionate hippurate.

10. A pharmaceutical composition comprising a compound of claim 1, an isomer thereof, a solvate thereof, a hydrate thereof or a pharmaceutically acceptable salt thereof of claim 1 as an active ingredient, wherein the composition further includes a pharmaceutically acceptable carrier, an additive or an excipient.

11. A method of inhibiting tryptophan hydroxylase, comprising administering to a subject in need thereof the compound of claim 1.

12. A method of treating a metabolic disorder related to tryptophan hydroxylase 1 (TPH1) activity, the method comprising administering to a subject in need thereof the compound of claim 1, an isomer thereof, a solvate thereof, a hydrate thereof or a pharmaceutically acceptable salt thereof.

13. The method according to claim 12, wherein the metabolic disorder is any one selected from the group consisting of obesity, diabetes mellitus, hyperlipidemia, arteriosclerosis, fatty liver, (nonalcoholic) fatty liver cirrhosis, (nonalcoholic) steatohepatitis, liver cirrhosis, celiac disease and hypertension.

14. A method of treating a cancer related to tryptophan hydroxylase 1 (TPH1) activity, the method comprising administering to a subject in need thereof the compound of claim 1, an isomer thereof, a solvate thereof, a hydrate thereof or a pharmaceutically acceptable salt thereof.

15. The method according to claim 14, wherein the cancer is any one selected from the group consisting of colorectal cancer, breast cancer, ovarian cancer, carcinoid tumor and hepatocellular carcinoma.

16. A method of treating a digestive or circulatory system disorder related to tryptophan hydroxylase 1 (TPH1) activity, the method comprising administering to a subject in need thereof the compound of claim 1, an isomer thereof, a solvate thereof, a hydrate thereof or a pharmaceutically acceptable salt thereof.

17. The method according to claim 16, wherein the digestive or circulatory system disorder is any one selected from the group consisting of hepatitis, pulmonary syndrome, pulmonary hypertension and inflammatory bowel disorder selected from the group consisting of enteritis, colitis, ulcerative enteritis, Crohn's disease, pheochromocytoma, irritable bowel syndrome, gastrointestinal bleeding, peptic ulcer and gastritis.

18. The compound, the isomer thereof, the solvate thereof, the hydrate thereof or the pharmaceutically acceptable salt thereof according to claim 1, wherein the compound is represented by Formula 36:

[Formula 36]

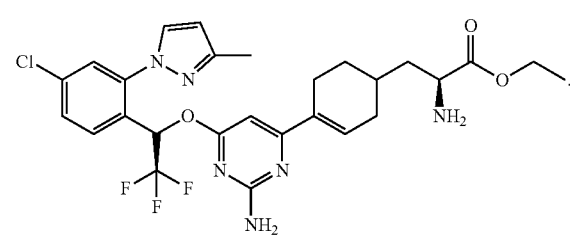

19. A pharmaceutically acceptable salt of the compound according to claim 18, further comprising hippuric acid

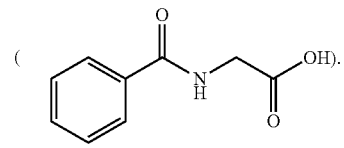

20. A composition, comprising a pharmaceutically acceptable salt according to Formula 53:

[Formula 53]

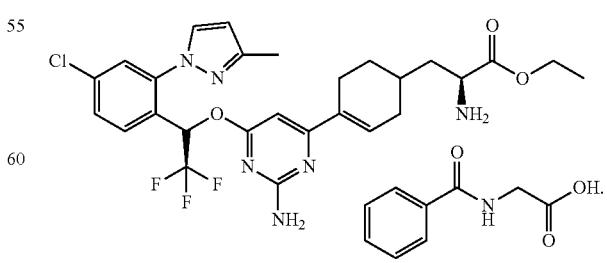

* * * * *